US009803012B2

(12) United States Patent
Herr et al.

(10) Patent No.: US 9,803,012 B2
(45) Date of Patent: Oct. 31, 2017

(54) COMPOSITIONS AND METHODS FOR REGULATING SAS1R

(75) Inventors: John C. Herr, Charlottesville, VA (US); Monika Sachdev, Charlottesville, VA (US); Arabinda Mandal, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 7 days.

(21) Appl. No.: 13/479,167

(22) Filed: May 23, 2012

(65) Prior Publication Data
US 2012/0252031 A1    Oct. 4, 2012

Related U.S. Application Data

(60) Division of application No. 12/613,947, filed on Nov. 6, 2009, now abandoned, which is a continuation-in-part of application No. 11/915,225, filed as application No. PCT/US2006/005970 on Feb. 21, 2006, now abandoned.

(60) Provisional application No. 60/655,562, filed on Feb. 23, 2005, provisional application No. 60/689,181, filed on Jun. 10, 2005, provisional application No. 61/111,903, filed on Nov. 6, 2008, provisional application No. 61/225,790, filed on Jul. 15, 2009, provisional application No. 61/243,411, filed on Sep. 17, 2009, provisional application No. 61/244,543, filed on Sep. 22, 2009.

(51) Int. Cl.
| C07K 16/28 | (2006.01) |
| A61K 38/17 | (2006.01) |
| A61K 38/48 | (2006.01) |
| A61K 39/00 | (2006.01) |

(52) U.S. Cl.
CPC ............ *C07K 16/28* (2013.01); *A61K 38/177* (2013.01); *A61K 38/1709* (2013.01); *A61K 38/4886* (2013.01); *A61K 39/0006* (2013.01); *C07K 2316/96* (2013.01); *C07K 2317/76* (2013.01); *G01N 2333/96486* (2013.01); *G01N 2500/04* (2013.01)

(58) Field of Classification Search
None
See application file for complete search history.

(56) References Cited

U.S. PATENT DOCUMENTS

| 6,461,850 | B2 | 10/2002 | Beasley et al. |
| 7,125,550 | B2 | 10/2006 | Herr et al. |
| 7,250,255 | B2 | 7/2007 | Yamanaka |
| 2002/0072106 | A1 | 6/2002 | Beasley et al. |
| 2008/0031926 | A1 | 2/2008 | Barbato et al. |
| 2008/0152664 | A1 | 6/2008 | White et al. |
| 2010/0183617 | A1 | 7/2010 | Herr et al. |

FOREIGN PATENT DOCUMENTS

| GB | WO2004056983 | * | 7/2004 | ............... C12N 9/00 |
| WO | WO-0153487 A1 | | 7/2001 | |
| WO | WO-02097090 A1 | | 12/2002 | |
| WO | WO-03089644 A1 | | 10/2003 | |
| WO | WO-2004064740 A2 | | 8/2004 | |
| WO | WO-2006091535 A2 | | 8/2006 | |
| WO | WO-2010054187 A2 | | 5/2010 | |
| WO | WO-2010054187 A3 | | 5/2010 | |

OTHER PUBLICATIONS

Sachdev et al., Developmental Biology, 2010: 363: 40-51.*
English machine translation of Hayashizaki et al. (WO2003089644, published Oct. 30, 2003); 108 pages total.*
Mandal et al., Biology of Reproduction 2008; 78: 69, Abstract #72.*
Frank, Journal of Immunological Methods, 2002; 267: 13-26.*
"U.S. Appl. No. 12/613,947, Non Final Office Action dated Mar. 22, 2012", 30 pgs.
"U.S. Appl. No. 12/613,947, Response dated Jan. 13, 2012 to Restriction Requirement dated Dec. 9, 2011", 13 pgs.
"U.S. Appl. No. 12/613,947, Restriction Requirement dated Dec. 9, 2011", 13 pgs.
"The Status, Quality, and Expansion of the NIH Full-Length cDNA Project: The Mammalian Gene Collection (MGC)", Genome Res 14(10b), (Oct. 2004), 2121-2127.
Carninci, P, "Normalization and Substration of ca-trapper-selected cDNAs to prepare full length cDNA libraries for rapid discovery of new genes", Genom Res. vol. 10, No. 10, (2000), 1617-1630.
Cohen, et al., "Association of egg zone pellucida glycoprotein mZP3 with sperm protein sp56 during fertilization in mice", Int. J. Dev. Biol. 45, (569-576), 2001.
Herrero, et al., "Mouse SLLP1, a sperm lysozyme-like protein involved in sperm-egg binding and fertilization", Developmental Biology 284, (2005), 126-142.
Johnson, Martin H, et al., "", Essential Reproduction: Fifth Edition, Blackwell Science, Ltd., (2000), 70.
Kurth, B. E, et al., "Immunogenicity of a multi-component recombinant human aerosomal protein vaccine in female Macaca fascicularis", J. Reproductive Immunol ogy., vol. 77, (2008), 126-141.

(Continued)

*Primary Examiner* — Christina Borgeest
(74) *Attorney, Agent, or Firm* — Buchanan Ingersoll & Rooney PC

(57) ABSTRACT

The present invention provides compositions and methods useful for regulating fertilization and for use as a contraceptive based on the discovery herein of an oocyte specific protein, SAS1R (Sperm Acrosomal SLLP1 Receptor), which is a sperm protein receptor. Six SAS1R variants, including the full length SAS1R, were identified. mSLLP1 and SAS1R co-localized to oocytes and to acrosomes of acrosome-reacted sperm. Interactions between mSLLP1 and SAS1R were demonstrated by far-western analysis, in a yeast two-hybrid system under stringent selection conditions, and by immunoprecipitation of SAS1R by anti-mSLLP1 as well as the converse. Purified recombinant SAS1R was found to have protease activity, to inhibit fertilization in-vitro, and to induce an immune response in females. Together, the results suggest SAS1R is a proteolytically active, oocyte and early embryo specific oolemmal metalloprotease receptor for the sperm intra-acrosomal ligand SLLP1 and is a target for regulating fertilization and as a contraceptive.

4 Claims, 18 Drawing Sheets

(56) References Cited

OTHER PUBLICATIONS

Mandal, A., et al., "SLLP1, A Unique, Intra-acrosomal, Non-bacteriolytic, c lysozyme-like Protein of Human Spermatozoa", Biology of Reproduction 68, XP009022809, (2003), 1525-1537.

Mendoza-Rodriguez, et al., "Mechanism of Cell Death Initiation in the Rat Uterine Epithelia During Proestrus-Estrus Transition", Biology of Reproduction 78, (May 2008), 69.

Mitsui, K, "The Homeoprotein Nanog is Required for Maitenance of Pluripotency in Mouse Epiblast and ES Cells", Cell vol. 113, No. 5, (2003), 631-342.

Phillips, A J, "The challenge of gene therapy and DNA delivery.", Journal of Pharmacy & Pharmacology, 53(9), (Sep. 2001), 1169-74.

Quesada, V., et al., "Identification and characterization of human and mouse ovastacin—A novel metalloproteinase similar to hatching enzymes from arthropods, birds, amphibians, and fish", Journal of Biological Chemistry, vol. 279, No. 25, (Jun. 2004), 26627-26634.

Tokuriki, et al., "Stability effects of mutations and protein evolvability", Current Opinion in Structural Biology 19, (2009), 596-604.

Wells, J A, "Additivity of mutational effects in proteins", Biochemistry 29, (8509-17), 1990.

"International Application Serial No. PCT/US2009/063540, International Preliminary Report on Patentability dated May 19, 2011", 7 pgs.

"International Application Serial No. PCT/US2009/063540, International Search Report dated Aug. 13, 2010", 5 pgs.

"International Application Serial No. PCT/US2009/063540, Written Opinion dated Aug. 13, 2010", 5 pgs.

\* cited by examiner

```
          E2                    E3        ▼                                             50
SAS1R-V1  MGIMGSLWPW  ILTMLSLLGL  SMGAPSASRC  SGVCSTSVPE  GFTPEGSPVF
SAS1R-V2  ..........  ..........  .MGAPSASRC  SGVCSTSVPE  GFTPEGSPVF
SAS1R-V3  ..........  ..........  .MGAPSASRC  SGVCSTSVPE  GFTPEGSPVF
SAS1R-V4  MGIMGSLWPW  ILTMLSLLGL  SMGAPSASRC  SGVCSTSVPE  GFTPEGSPVF
SAS1R-V5  ..........  ..........  .MGAPSASRC  SGVCSTSVPE  GFTPEGSPVF
SAS1R-V6  MGIMGSLWPW  ILTMLSLLGL  SMGAPSASRC  SGVCSTSVPE  GFTPEGSPVF
          51                      E4                      E5          100
SAS1R-V1  QDKDIPAINQ  GLISEETPES  SFLVEGDIIR  PSPFRLLSVT  NNKWPKGVGG
SAS1R-V2  QDKDIPAINQ  GLISEETPES  SFLVEGDIIR  PSPFRLLSVT  NNKWPKGVGG
SAS1R-V3  QDKDIPAINQ  GLISEETPES  S.........  ..........  ..........
SAS1R-V4  QDKDIPAINQ  GLISEETPES  S.........  ..........  ..........
SAS1R-V5  QDKDIPAINQ  GLISEETPES  SFLVEGDIIR  PGVSHGVSFP  D.........
SAS1R-V6  QDKDIPAINQ  GLISEETPES  SFLVEGDIIR  PGVSHGVSFP  N.........
          101                     E6                                  150
SAS1R-V1  FVEIPFLLSR  KYDELSRRVI  MDAFAEFERF  TCIRFVAYHG  QRDFVSILPM
SAS1R-V2  FVEIPFLLSR  KYDELSRRVI  MDAFAEFERF  TCIRFVAYHG  QRDFVSILPM
SAS1R-V3  .....FLLSR  KYDELSRRVI  MDAFAEFERF  TCIRFVAYHG  QRDFVSILPM
SAS1R-V4  .....FLLSR  KYDELSRRVI  MDAFAEFERF  TCIRFVAYHG  QRDFVSILPM
SAS1R-V5  ..........  ...ELSRRVI  MDAFAEFERF  TCIRFVAYHG  QRDFVSILPM
SAS1R-V6  ..........  ...ELSRRVI  MDAFAEFERF  TCIRFVAYHG  QRDFVSILPM
          E7                                  ▼                       200
SAS1R-V1  AGCFSGVGRS  GGMQVVSLAP  TCLRKGRGIV  LHELMHVLGF  WHEHSRADRD
SAS1R-V2  AGCFSGVGRS  GGMQVVSLAP  TCLRKGRGIV  LHELMHVLGF  WHEHSRADRD
SAS1R-V3  AGCFSGVGRS  GGMQVVSLAP  TCLRKGRGIV  LHELMHVLGF  WHEHSRADRD
SAS1R-V4  AGCFSGVGRS  GGMQVVSLAP  TCLRKGRGIV  LHELMHVLGF  WHEHSRADRD
SAS1R-V5  AGCFSGVGRS  GGMQVVSLAP  TCLRKGRGIV  LHELMHVLGF  WHEHSRADRD
SAS1R-V6  AGCFSGVGRS  GGMQVVSLAP  TCLRKGRGIV  LHELMHVLGF  WHEHSRADRD
          201                     E8                      E9          250
SAS1R-V1  RYIQVNWNEI  LPGFEINFIK  SRSTNMLVPY  DYSSVMHYGR  FAFSWRGQPT
SAS1R-V2  RYIQVNWNEI  LPGFEINFIK  SRSTNMLVPY  DYSSVMHYGR  FAFSWRGQPT
SAS1R-V3  RYIQVNWNEI  LPGFEINFIK  SRSTNMLVPY  DYSSVMHYGR  FAFSWRGQPT
SAS1R-V4  RYIQVNWNEI  LPGFEINFIK  SRSTNMLVPY  DYSSVMHYGR  FAFSWRGQPT
SAS1R-V5  RYIQVNWNEI  LPGFEINFIK  SRSTNMLVPY  DYSSVMHYGR  FAFSWRGQPT
SAS1R-V6  RYIQVNWNEI  LPGFEINFIK  SRSTNMLVPY  DYSSVMHYGR  FAFSWRGQPT

251                                             E10         300
SAS1R-V1  IIPLWTSSVH  IGQRWNLSTS  DITRVCRLYN  CSRSVPDSHG  RGFEAQSDGS
SAS1R-V2  IIPLWTSSVH  IGQRWNLSTS  DITRVCRLYN  CSRSVPDSHG  RGFEAQSDGS
SAS1R-V3  IIPLWTSSVH  IGQRWNLSTS  DITRVCRLYN  CSRSVPDSHG  RGFEAQSDGS
SAS1R-V4  IIPLWTSSVH  IGQRWNLSTS  DITRVCRLYN  CSRSVPDSHG  RGFEAQSDGS
SAS1R-V5  IIPLWTSSVH  IGQRWNLSTS  DITRVCRLYN  CSRSVPDSHG  RGFEAQSDGS
SAS1R-V6  IIPLWTSSVH  IGQRWNLSTS  DITRVCRLYN  CSRSVPDSHG  RGFEAQSDGS
          301                                                         350
SAS1R-V1  SLTPASISRL  QRLLEALSEE  SGSSAPSGSR  TGGQSIAGLG  NSQQGWEHPP
SAS1R-V2  SLTPASISRL  QRLLEALSEE  SGSSAPSGSR  TGGQSIAGLG  NSQQGWEHPP
SAS1R-V3  SLTPASISRL  QRLLEALSEE  SGSSAPSGSR  TGGQSIAGLG  NSQQGWEHPP
SAS1R-V4  SLTPASISRL  QRLLEALSEE  SGSSAPSGSR  TGGQSIAGLG  NSQQGWEHPP
SAS1R-V5  SLTPASISRL  QRLLEALSEE  SGSSAPSGSR  TGGQSIAGLG  NSQQGWEHPP
SAS1R-V6  SLTPASISRL  QRLLEALSEE  SGSSAPSGSR  TGGQSIAGLG  NSQQGWEHPP
          351                                                         400
SAS1R-V1  QSTFSVGALA  RPPQMLADAS  KSGPGAGADS  LSLEQFQLAQ  APTVPLALFP
SAS1R-V2  QSTFSVGALA  RPPQMLADAS  KSGPGAGADS  LSLEQFQLAQ  APTVPLALFP
SAS1R-V3  QSTFSVGALA  RPPQMLADAS  KSGPGAGADS  LSLEQFQLAQ  APTVPLALFP
SAS1R-V4  QSTFSVGALA  RPPQMLADAS  KSGPGAGADS  LSLEQFQLAQ  APTVPLALFP
SAS1R-V5  QSTFSVGALA  RPPQMLADAS  KSGPGAGADS  LSLEQFQLAQ  APTVPLALFP
SAS1R-V6  QSTFSVGALA  RPPQMLADAS  KSGPGAGADS  LSLEQFQLAQ  APTVPLALFP
          401                     435
SAS1R-V1  EARDKPAPIQ  DAFERLAPLP  GGCAPGSHIR  EVPRD
SAS1R-V2  EARDKPAPIQ  DAFERLAPLP  GGCAPGSHIR  EVPRD
SAS1R-V3  EARDKPAPIQ  DAFERLAPLP  GGCAPGSHIR  EVPRD
SAS1R-V4  EARDKPAPIQ  DAFERLAPLP  GGCAPGSHIR  EVPRD
SAS1R-V5  EARDKPAPIQ  DAFERLAPLP  GGCAPGSHIR  EVPRD
SAS1R-V6  EARDKPAPIQ  DAFERLAPLP  GGCAPGSHIR  EVPRD
```

Figure 9

```
                    1                                              ▼                                     50
         Human   MEGVGGLWPW  VLGLLSLPGV  ILGAPLAS..  SCAGACGTSF  PDGLTPEGTQ
         Mouse   MGIMGSLWPW  ILTMLSLLGL  SMGAPSAS..  RCSGVCSTSV  PEGFTPEGSP
     Zebrafish   ~~~~~~~~MD  IRASLSILLL  LFGLSQAS..  PL.....REF  EAVFVSEPET
      Nematode   ~~~~~~~~~~  ~MMTIQRYSL  VFCAIFATCW  TASVVNNKQV  IDTSVPQTET
     Consensus   ~~~~~~~~~~  ~~~~L~~~~~  ~~~~~~A~~~  ~~~~~~~~~~  ~~~~~~E~~~
                   51                                                   100
         Human   ASGDKDIPA.  INQ.......  GLILEETPES  SFLIEGDIIR  PSPFRLLSAT
         Mouse   VFQDKDIPA.  INQ.......  GLISEETPES  SFLVEGDIIR  PSPFRLLSVT
     Zebrafish   VDITTQILE.  TNK.......  G........SS  EVLFEGDVVL  PKNRNALICE
      Nematode   TLNDADFHSD  LHQRYDLQTL  GIKVKDDPTI  GNYSEGDILL  ESPKKFVEEN
     Consensus   ~~~~~~~~~~  ~~~~~~~~~~  G~~~~~~~~~  ~~~~EGDII~  ~~~~~~~~~~
                  101                                                   150
         Human   SN......K.  .WPMGGSGVV  EVPFLLSSKY  DEPSRQVILE  ALAEFERSTC
         Mouse   NN......K.  .WPKGVGGFV  EIPFLLSRKY  DELSRRVIMD  AFAEFERFTC
     Zebrafish   DK......SC  FWKKNANNIV  EVPYVVSGEF  SINDKSVIAN  AISIFHAQTC
      Nematode   NKLGRNAIKQ  IYRRWPNN..  EIPYTLSSQY  GSYARSVIAN  AMNEYHTKTC
     Consensus   ~~~~~~~~~~  ~W~~~~~~~~  E~P~~~S~~Y  ~~~~R~VI~~  A~~~F~~~TC
                  151                                                   200
         Human   IRFVTYQDQR  ..DFISIIPM  YGCFSSVGRS  GGMQVVSL.A  PTCLQKGRGI
         Mouse   IRFVAYHGQR  ..DFVSILPM  AGCFSGVGRS  GGMQVVSL.A  PTCLRKGRGI
     Zebrafish   IRFVPRSIQA  ..DYLSIENK  DGCYSAIGRT  GGKQVVSLNR  KGCVYS..GI
      Nematode   VKFVARDPSK  HHDYLWIHPD  EGCYSLVGKT  GGKQPVSLDS  .GCIQ..VGT
     Consensus   IRFV~~~~~~  ~~D~L~I~~~  ~GC~S~VGR~  GG~Q~VSL~~  ~~CL~~~~G~
                                                                        250
         Human   VLHELMHVLG  FWHEHTRADR  DRYIRVNWNE  ILPGFEINFI  KSQSS...NM
         Mouse   VLHELMHVLG  FWHEHSRADR  DRYIQVNWNE  ILPGFEINFI  KSRST...NM
     Zebrafish   AQHELNHALG  FYHEQSRSDR  DQYVRINWNN  ISPGMAYNFL  KQKTN...NQ
      Nematode   IVHELMHAVG  FFHEQSRQDR  DSYIDVWWQN  VMNGADDQFE  KYNLNVISHL
     Consensus   ~~HEL~H~~G  FWHE~~R~DR  D~YI~V~W~~  I~~G~~~~F~  K~~~~~~~~~
                  251                                                   300
         Human   LTPYDYSSVM  HYGRLAFSRR  .GLPTITPLW  APSVHIGQRW  NLSASDITRV
         Mouse   LVPYDYSSVM  HYGRFAFSWR  .GQPTIIPLW  TSSVHIGQRW  NLSTSDITRV
     Zebrafish   NTPYDYGSIM  HYGKTAFAIQ  PGLETITPIP  DENVQIGQRQ  GLSKIDTLGI
      Nematode   DEPYDYASIM  HYGPYAFS.G  SGKKTLVPKK  SGSERMGQRV  KFSDIDVRKI
     Consensus   ~~PYDY~SVM  HYG~~AF~~~  ~G~~TI~P~~  ~~~~~~GQR~  ~~S~~DI~~~
                  301                                                   350
         Human   LKLYGCSPSG  PRFRGRGSHA  HSTGRSPAPA  SLS.LQRLLE  ALSAESRSPD
         Mouse   CRLYNCSRSV  PDSHGRGFEA  QSDGSSLTPA  SISRLQRLLE  ALSEESGSSA
     Zebrafish   NKLYGC~~~~  ~~~~~~~~~~  ~~~~~~~~~~  ~~~~~~~~~~  ~~~~263 aa
      Nematode   NKLYNCPGVS  GNNNNNNNNQ  INSNSIVNHP  QV~~~~~~~~  ~~~~315 aa
     Consensus   ~KLY~C~~~~  ~~~~~~~~~~  ~~~~~~~~~~  ~~~~~~~~~~  ~~~~~~~~~~
                  351                                                   400
         Human   PSGSSAGGQP  VEAGPGESPH  GWESPALKKL  SAEASARQPQ  TLASSPRSRP
         Mouse   PSGSRTGGQS  I.AGLGNSQQ  GWEHPPQSTF  SVGALARPPQ  MLADASKSGP
                  401                                                   450
         Human   GAGAPGVAQE  QSWLAGVSTK  PTVPSSEAGI  QFVPVQGS..  ..PALPGGCV
         Mouse   GAGADSLSLE  QFQLAQAPTV  PLALFPEARD  KFAPIQDAFE  RLAPLPGGCA
                  451         461
         Human   PRNHFKGMSE  D   431 aa
         Mouse   PGSHIREVPR  D   435 aa
```

Figure 10

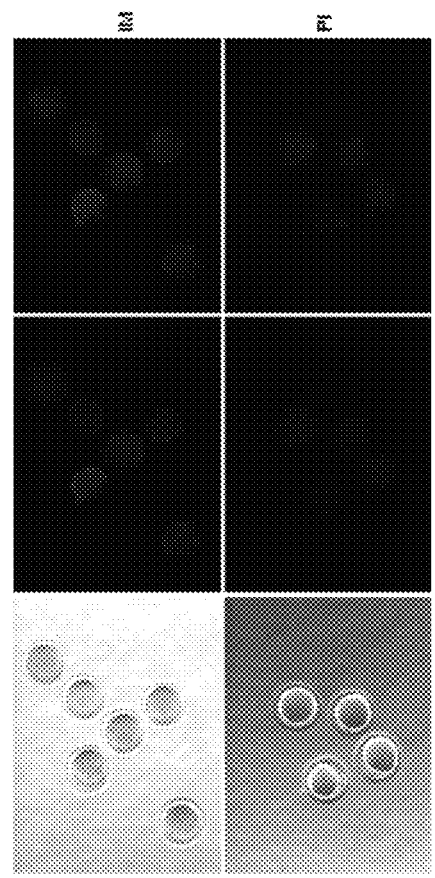
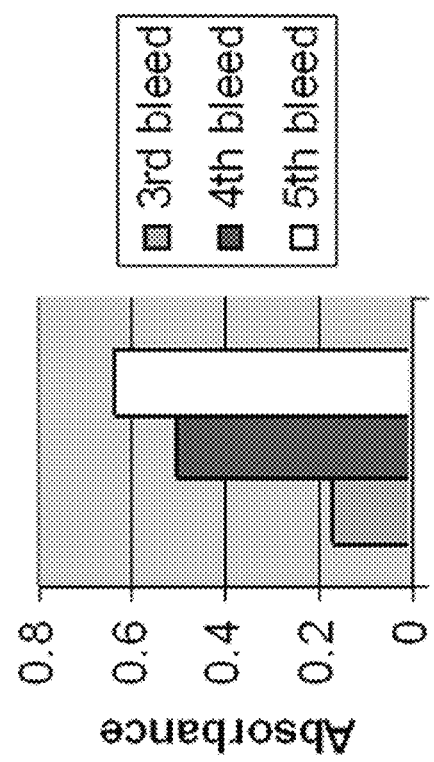
Figure 17

Figure 24

COMPOSITIONS AND METHODS FOR REGULATING SAS1R

CROSS REFERENCE TO RELATED APPLICATIONS

This application is a divisional of U.S. patent application Ser. No. 12/613,947, filed Nov. 6, 2009, which is a continuation-in-part of U.S. patent application Ser. No. 11/915,225, filed Nov. 24, 2008, which claims the benefit of priority to International Application No. PCT/US2006/005970, filed on Feb. 21, 2006, which is entitled to priority pursuant to 35 U.S.C. §119(e) to U.S. Provisional Patent Application Ser. Nos. 60/655,562, filed Feb. 23, 2005, and 60/689,181, filed Jun. 10, 2005, and this application is further entitled priority to U.S. Provisional Patent Application Ser. Nos. 61/111,903, filed Nov. 6, 2008, 61/225,790, filed Jul. 15, 2009, 61/243,411 filed Sep. 17, 2009, and 61/244,543, filed Sep. 22, 2009, the entire disclosures of which are herein incorporated by reference.

STATEMENT REGARDING FEDERALLY SPONSORED RESEARCH OR DEVELOPMENT

This invention was made with government support under Grant Nos. R03 HD055129 awarded by the NIH and D43 TW/HD 00654 from the Fogarty International Center. The government has certain rights in the invention.

BACKGROUND

Among the events of fertilization, few are more important, yet enigmatic, than interactions between the sperm and egg membranes. Although several sperm proteins that bind to mammalian oocytes have been identified, there has been less success in identifying oolemmal receptors for sperm ligands. The unique testis-specific c lysozyme-like, intra-acrosomal protein SLLP1, was reported to lack bacteriolytic activity (1); localize to mouse sperm acrosomal membranes, and have oolemma binding properties (2). SLLP1 antibody and recombinant (r) SLLP1 were noted to block fertilization and sperm-egg binding in mice, suggesting that the protein may play a role in sperm/egg adhesion.

Molecules posited to be involved in sperm-oolemmal binding and fusion include the ADAM family ligands and their oocyte integrin receptors (3-6). However, gene targeting studies have demonstrated that the sperm ADAMs including fertilin a (ADAM1), fertilinβ (ADAM2) and cyritestin (ADAM3) are important primarily for the process of zona pellucida binding rather than for gamete fusion (7-9). Attention has also focused on tetraspanins (e.g., CD9, CD81), on GPI-anchored proteins, and on PIG-A which are expressed on oocytes. Data suggest that these proteins are important for the sperm-oocyte fusion step, but not for the binding process (10-12). Although $CD9^{-/-}$ female mice produced eggs that matured normally, sperm-egg fusion failed in these animals (13, 14). Targeted disruption of CD81 resulted in a 40% reduction in fertility of only female mice while mice lacking both CD9 and CD81 were completely infertile, indicating their complementary roles in sperm-egg fusion (15). It is noteworthy that sperm ligands that interact with oolemmal tetraspanins have not been identified. Several sperm membrane ligands have been implicated in fusion with the oocyte although their oolemmal receptors are unknown. Epididymal protein DE (CRISP1) has been implicated in sperm-oocyte fusion (16) and a specific binding region within CRISP1 was mapped, however CRISP1 knockout male and female mice showed no differences in fertility compared to controls (17). Recently, Izumo, an Ig-domain molecule localized within the acrosome was shown to be essential for sperm-egg fusion (18) although its oolemmal receptor is still unknown.

Moreover, there has been a concerted effort to identify biomarkers and differentiation antigens that are specific to the sperm or the egg in order to target these cells for contraceptive purposes, including drug and vaccine development. These approaches have included monoclonal antibodies directed a the gametes, proteomic, transcriptomic and genomic approaches (Nass et al., Nat Rev Drug Discov. 2004 October; 3(10):885-90); Nass et al., Science. 2004 Mar. 19; 303(5665):1769-71; Nass et al., National Academy Press, p 27-77, (2004), Contraception. 2008 October; 78 (4 Suppl):S28-35. Epub 2008 Aug. 22; Aitken et al., Contraception. 2008 October; 78 (4 Suppl):S18-22. Epub 2008 Jun. 12.)

Candidates proteins for contraceptive targeting must meet selective criteria including 1) restriction of the protein to the gamete; 2) an essential role for the protein in key stages of gametogenesis, fertilization or implantation; 3) accessibility of the drug target at the cell surface or within a select window of differentiation; 4) structural domains amenable to drug targeting (drugability); and 5) the restriction of the target to selected stages of gamete differentiation that permit targeted drug action and contraceptive reversibility in the case of human applications. Until now, few proteins have been elucidated that meet all of these criteria.

There is a long felt need in the art to identify both sperm and oolemma specific interacting proteins involved in the process of fertilization and to find methods to regulate these interactions to regulate fertility and contraception. The present invention satisfies these needs.

SUMMARY OF THE INVENTION

The present invention provides compositions and methods useful as contraceptive vaccines, as methods of inducing an immune response, as a contraceptive drug target for selectively affecting maturing oocytes while sparing young oogonia that are naked, or within primordial or primary follicles; and as a method of modulating fertilization and fertility. The compositions comprise at least one mammalian egg protein, or a homolog, derivative, or fragment thereof, or at least one isolated nucleic acid comprising a nucleic acid sequence encoding an egg protein. The compositions are particularly useful as contraceptives for, including, but not limited to, humans, dogs, cats, and mice.

The compositions and methods of the invention are based on the unexpected results disclosed herein that SAS1R (Sperm Acrosomal SLLP1 Receptor) is, inter alia, an immunogenic oocyte stage specific metalloprotease that binds with the sperm protein SLLP1, furthermore that inhibition of the protein or its interaction with SLLP1 inhibits fertilization, and because of its specific stage specific expression in follicles its use as a contraceptive target will spare oocyte stem cells. Furthermore, these biological and biochemical properties of SAS1R allow for its use as a contraceptive target and its use as a contraceptive vaccine, both in a reversible manner, as well as methods of identifying contraceptive agents.

A contraceptive drug target, such as the one disclosed herein, fulfills essential criteria for drug development including functioning in fertilization and being specific to oocytes in secondary and subsequent follicular stages such that drug targeting of this protein will not affect stem germ cells including naked, primordial and primary oocytes.

In one aspect, the composition comprises a cocktail or mixture of two or more different egg proteins or two or more different isolated nucleic acids comprising nucleic acid sequences encoding different egg proteins, which can be used as a contraceptive vaccine or to induce an immune response directed against the egg proteins.

With knowledge of oolemmal receptors limited and with an eye to the design of molecular strategies for contraception, it is necessary to identify both sperm and oolemmal specific interacting proteins involved in the process of fertilization. The present application presents several lines of evidence characterizing the molecular, biochemical, and functional properties of the SLLP1 receptor, SAS1R (Sperm Acrosomal SLLP1 Receptor), their interactions, and demonstrating the timing and pattern of SAS1R expression in oocytes and early embryos. SAS1R appears to be the only oocyte and early embryo specific membrane receptor for a sperm ligand that has been identified to date in mammalian fertilization. Although sperm membrane metalloproteases have been previously characterized, SAS1R is the first oolemmal metalloprotease implicated in sperm-oolemma binding prior to sperm-egg fusion and it is disclosed herein as being capable of inducing an immune response in females. These properties support consideration of SAS1R as a candidate contraceptive drug or vaccine target.

The present invention provides compositions and methods useful for inhibiting the interaction of SLLP1 with SAS1R, thereby inhibiting fertilization. The present invention provides compositions and methods useful for inhibiting fertilization by inhibiting the interaction of SLLP1 and SAS1R. The interaction can be inhibited various ways, including, but not limited to, the use of purified SLLP1 and SAS1R proteins, or analogs, derivatives, homologs, or fragments thereof, to prevent binding of the sperm protein to the egg protein. The present application further provides for the use of antibodies directed against SAS1R to inhibit fertilization. In one aspect, the type of antibody includes, but is not limited to, a polyclonal antibody, a monoclonal antibody, a chimeric antibody, and a synthetic antibody. In one aspect, the antibody is a monoclonal antibody.

The present invention provides compositions and methods useful for identifying regulators of SAS1R and its function. In one aspect, the regulators are inhibitors of SAS1R. Inhibitors of SAS1R includes those which inhibit its interaction or binding with a sperm protein such as SLLP1, its activity as a protease, its role in fertilization, or inhibit its regulation of downstream activities included in SAS1R signal transduction pathways. In one aspect, the inhibitor is SAS1R, or a fragment or homolog of SAS1R which binds with SLLP1. In one aspect, the SAS1R fragment is an N-terminus portion of the protein. In one aspect, the N-terminus comprises about the amino terminal 121 amino acid residues of mature SAS1R. In another aspect, the SAS1R fragment which binds with SLLP1 and inhibits SLLP1 interaction with an egg is a C-terminus portion of SAS1R. In one aspect, the C-terminus of the SAS1R comprises about the carboxy terminal 210 amino acid residues of SAS1R. One of ordinary skill in the art will appreciate that any kind of compound that inhibits SAS1R levels, function, or activity as described herein, or those that are yet unknown, are encompassed by the present invention.

In one embodiment, the present invention provides compositions and methods useful for determining that SAS1R functions as an active metalloprotease, as well as for measuring that function. These methods are useful for determining whether a test compound or molecule can inhibit SAS1R.

In one aspect, SAS1R is inhibited in an N-terminus portion of the protein. In one aspect, the N-terminus comprises about the amino terminal 121 amino acid residues of mature SAS1R. In another aspect, the SAS1R is inhibited in a C-terminus portion of the protein. In one aspect, the C-terminus of the protein comprises about the carboxy terminal 210 amino acid residues of SAS1R. In one aspect, the inhibitor is an antibody directed against SAS1R. In another aspect, the inhibitor is a drug or other compound. In one aspect, the inhibitor inhibits the protease activity of SAS1R. In another aspect, the inhibitor inhibits the interaction of SAS1R with SLLP1 any other sperm protein. In one aspect, the interaction is binding.

The present inventors have surprisingly found that suitable antigens for immunotherapeutic strategies include the egg protein SAS1R. The present application discloses immunogenic compositions comprising an immunogen derived from eggs. That antigen is the SAS1R protein, as well as antigenic fragments and homologs thereof. The present invention provides compositions and methods useful for inhibiting fertilization and for contraception. In one aspect, SAS1R, or fragments or homologs thereof which maintain the immunogenic activity of full length SAS1R, can be administered to a subject to elicit an immune response against SAS1R. In one aspect, the administration of SAS1R and fragments and homologs thereof is useful as a vaccine.

In one embodiment, the compositions and methods of the invention are useful in mammals. In one aspect, the mammal is a human.

Together, the data disclosed herein demonstrated that SAS1R is a proteolytically active, oocyte and early embryo specific oolemmal metalloprotease receptor for the sperm intra-acrosomal ligand SLLP1 and is a target for regulating fertilization and as a contraceptive. Surprisingly, and importantly, the enzyme is demonstrated herein to show stage specific expression in secondary and subsequent follicular oocytes, including preantral and antral follicles, rendering it a suitable target for a reversible contraceptive that will spare naked, primordial, and primary oocytes, and preserve the ovarian reserve of stem germ cells. Therefore, the invention further encompasses the compositions and methods for identifying compounds that inhibit SAS1R.

Various aspects and embodiments of the invention are described in further detail below.

BRIEF DESCRIPTION OF THE DRAWINGS

FIG. 9: SAS1R splice variants (SEQ ID NOs: 6, 8, 10, 19, 20 and 21). Six isoforms of SAS1R were cloned from mouse ovarian cDNA library and aligned using ClustalW+, including the full-length protein (V1) and five splice variants (V2-V6). The beginning of each exon is marked by the exon number (E2-E10). The two peptides identified by surface plasmon resonance and mass spectrometric studies of SAS1R are marked with underlined residues in variant 1. Each ovarian variant possessed a zinc binding active site signature (in boxed) and contained a putative transmembrane domain (in shade) by specific algorithms available online (i.e., the Prediction of Transmembrane Regions and Orientation section of the website maintained by EMBnet and the Pasteur Institute's website). The predicted signal peptide cleavage site (using tools available at the website of The Center for Biological Sequence Analysis at the Technical University of Denmark) and the catalytic residue in the zinc binding active site are marked (♥ and ▼ respectively). The variants 1, 4 & 6 encode a signal peptide while variants 2, 3 & 5 lack the signal peptide (E2, exon 2). Variants 3 & 4 possess a deletion of 34 amino acids form exon 4 and 5. Variants 5 & 6 have a replacement of exon 5 with insertion of 9 residues (in italics). The GenBank accession numbers of these variants are: V1, FJ187790; V2; FJ187791; V3; FJ197792; V4, FJ187793; V5, FJ197794; V6, FJ187795.

FIG. 10: Alignment of deduced amino acid sequence of mouse SAS1R (V1), the human orthologue and homologs in zebrafish and nematodes from GenBank (SEQ ID NOs: 22, 23, 28 and 29), at the U.S. National Library of Medicine website maintained by the National Institutes of Health. For optimal alignment, gaps (•) were introduced into the sequence using GCG PileUp program (Accelrys, San Diego, Calif.). A consensus sequence was created using similarity of residue in all four sequences (accession #: mouse, FJ187790; human, NP 001002036.3; zebrafish, NP_998800.1; nematode, NP_498405.2). In all species, SAS1R has a predicted signal peptide (residues in italics) and a zinc-dependent metalloprotease domain (closed rectangle). The predicted signal peptide cleavage site and the catalytic residue in the zinc binding active site in human sequence are marked (♥ and ▼ respectively). Mammalian orthologues contain a predicted transmembrane domain (shaded residues) while lower organisms, including chicken (accession #, XP_421101.2), zebrafish, and nematode, except Drosopila (accession #, NP_651138.1), lack this putative transmembrane domain. The underlined region represents the conserved zince metalloprotease superfamily domain from several subfamilies (which include hatching enzyme, astacin, astacin-like, meprin, bone morphogenesis protein 1, etc). The number of residues (aa) in each protein is shown at the end of each sequence.

FIG. 17, comprising left and right panels, depicts the results of isologous immunization of female mice and Mouse SAS1R isologous antibody response. As an oocyte specific, sperm oolemmal receptor, SAS1R was hypothesized herein to be a candidate contraceptive vaccinogen and immunogen. Immunogenicity of recombinant mouse SAS1R was tested in female mice which showed serum titers by ELISA against the recombinant target up to a 1/10,000 dilution after the 3rd, 4th & 5th injections (FIG. 17, left panel). The immunoreactivity of the sera were also studied by immunolocalization in live mouse eggs (FIG. 17, right panel). The iso-antibodies from female mice stained the microvillar domain of mouse eggs exactly as noted earlier with allo-antibodies raised in guinea pigs (right panel). This finding confirmed that recombinant mouse SAS1R retained sufficient refolded epitopes to evoke iso-antibodies that cross-reacted with native SAS1R on the microvillar domain.

FIG. 24: Day 56—Adult mouse ovary sections 56 days after birth stained with pre-immune [PI, left panel] or guinea pig anti-SAS1R antibodies [IM, right panel] at identical concentrations [1:500].

DETAILED DESCRIPTION

Figure 1:
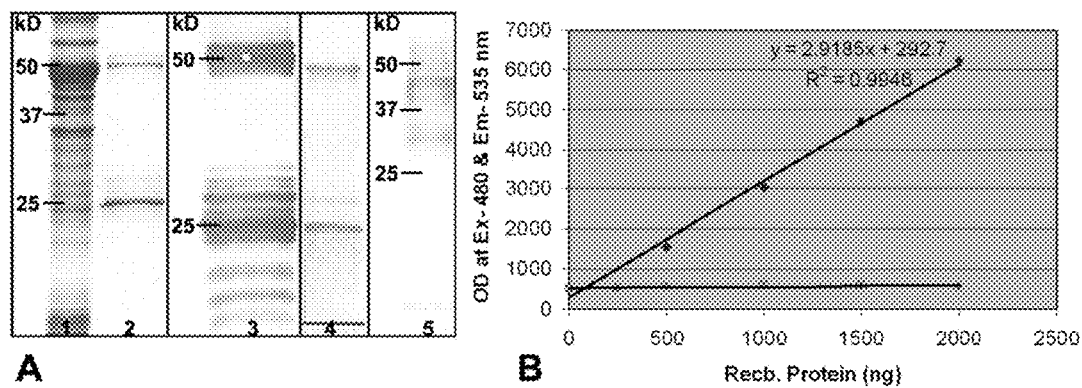
FIG. 1: Expression, purification, Western and protease activity of rSAS1R. (A) The mature protein was expressed in *E. coli* (L 1), purified (L 2) and stained with Coomassie Blue. All purified bands were confirmed as rSAS1R by anti-His Western analysis (L 3). Antibody to rSAS1R recognized the recombinant (L 4) and the native SAS1R in zona intact oocyte extracts (L 5). Native SAS1R showed microheterogeneity. (B) Assay of protease activity of rSAS1R (♦) using a fluorescent tagged synthetic peptide as substrate. Varying concentrations of purified proteins were used in 100 µL assay system. rSLLP1 (■) was used as a negative control.

Abbreviations and Acronyms
a.a.—amino acid(s)
BSA—bovine serum albumin
Co-IP—co-immunoprecipitation
FITC—fluorescein isothiocyanate FRET—fluorescence resonance energy transfer
FW—Far Western
GV—germinal vesicle
h—human (also hour)
HPLC—reversed-phase high-pressure liquid chromatography
HS—high stringency
I—induced or immune
IF—Indirect immunofluorescent
IP—immunoprecipitation
IPTG—Isopropyl-β-D-thiogalactopyranoside
LB—Luria broth
LS—low stringency
IM—immune
m—mouse
MET—mouse egg-specific TolA (referred to in the provisional application as a Colcin-like uptake protein or Colicin uptake protein)
min—minute
NGS—normal goat serum
OL—overlay
P—purified
PI—pre-immune
PBS—phosphate-buffered saline
PBST—phosphate buffered saline with 0.05% Tween 20
PVA—polyvinylalcohol
rec—recombinant (rec is used interchangeably with "r")
SAS1R—Sperm Acrosomal SLLP1 Receptor (previously referred to as ZEP)
rSAS1R—recombinant SAS1R
sec—second(s)
SLLP—sperm lysozyme-like protein
SPR—surface plasmon resonance
U—uninduced
ZEP—zinc endopeptidase (referred to in the provisional application as zinc peptidase, or ZP; used interchangeably with SAS1R)
ZFE—zona free egg
ZIE—zona intact egg

SUMMARY OF SEQ ID NOS: USED AND THE MATCHING NAMES

SEQ ID NOs:
SEQ ID NO:1—mouse ("m") MET normal nucleic acid sequence
SEQ ID NO:2—mouse MET normal amino acid sequence
SEQ ID NO:3—mouse MET variant nucleic acid sequence
SEQ ID NO:4—mouse MET variant amino acid sequence
SEQ ID NO:5—mouse SAS1R Variant 2 Normal nucleic acid sequence (formerly called ZEP-Normal)
SEQ ID NO:6—mouse SAS1R Variant 2 Normal amino acid sequence (formerly called ZEP-Normal)
SEQ ID NO:7—mouse SAS1R Variant 5 nucleic acid sequence (formerly called ZEP Variant 1)
SEQ ID NO:8—mouse SAS1R Variant 5 amino acid sequence (formerly called ZEP Variant 1)
SEQ ID NO:9—mouse SAS1R Variant 3 nucleic acid sequence (formerly called ZEP Variant 2)
SEQ ID NO:10—mouse SAS1R Variant 3 amino acid sequence (formerly called ZEP Variant 2)
SEQ ID NO:11—mouse SLLP1 nucleic acid sequence
SEQ ID NO:12—mouse SLLP1 amino acid sequence
SEQ ID NO:13—human ("h") SLLP1 nucleic acid sequence
SEQ ID NO:14—human SLLP1 amino acid sequence
SEQ ID NO:15—mouse SLLP2 nucleic acid sequence
SEQ ID NO:16—mouse SLLP2 mature protein amino acid sequence
SEQ ID NO:17—human SLLP2 nucleic acid sequence
SEQ ID NO:18—human SLLP2 amino acid sequence
SEQ ID NO:19—mouse SAS1R Variant 1 amino acid sequence
SEQ ID NO:20—mouse SAS1R Variant 4 amino acid sequence
SEQ ID NO:21—mouse SAS1R Variant 6 amino acid sequence
SEQ ID NO:22—human SAS1R nucleic acid sequence (GenBank accession no. NM_001002036, 1296 bp mRNA)
SEQ ID NO:23—human SAS1R amino acid sequence (GenBank accession no. NP_001002036.3, 431 amino acids)
SEQ ID NO:24—HELMHVLGFWH (motif in SAS1R with histidine residues for Zn coordination and conserved catalytic residue, E [glutamic acid], forms part of the catalytic pocket along with a tyrosine zinc ligand embedded in the motif SXMHY (SEQ ID NO:25).
SEQ ID NO:25—SVMHY (motif in SAS1R associated with the catalytic pocket)
SEQ ID NO:26—HEXXHXXGXXH (the consensus motif of SEQ ID NO:24 can have residues which can be substituted with any amino acid, as indicated by "X", that does not ablate the function of that motif).
SEQ ID NO:27—SXMHY (the consensus motif of SEQ ID NO:25 can have residues which can be substituted with any amino acid, as indicated by "X", that does not ablate the function of that motif).
SEQ ID NOs:1-18 are the same sequences as SEQ ID NOs:1-18 of international patent application WO 2006/091535 (PCT/US2006/005970; Mandal et al.; published Aug. 31, 2006), in which SAS1R was referred to as ZEP.

Definitions

In describing and claiming the invention, the following terminology will be used in accordance with the definitions set forth below.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

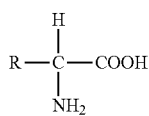

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

"C19" and "C23" are names which are also used for "SLLP1" and SLLP2",

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys V. Large, aromatic residues:

Phe, Tyr, Trp

"Contraceptive", as used herein, refers to an agent, compound, or method that diminishes the likelihood of or prevents conception.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, the term "diagnosis" refers to detecting a risk or propensity to an addictive related disease disorder. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

As used herein, the phrases "egg protein" or "egg-specific protein" refer to proteins which are expressed exclusively or predominately in eggs or ovaries. The proteins need not be expressed at all stages of egg or ovarian development.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

The phrase "inhibit conception", as used herein, refers to both direct and indirect inhibition of conception or impregnation, regardless of the mechanism. The phrase also includes reducing the rate of conception, and does not necessarily mean that conception is inhibited by 100%.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

By 'interaction" between a sperm protein and an egg protein is meant the interaction such as binding which is necessary for an event or process to occur, such as sperm-egg binding, fusion, or fertilization. In one aspect, the "interaction" may be similar to receptor-ligand type of binding or interaction.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self administration.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

An "oocyte" as used herein can be categorized more specifically several ways. A "naked oocyte" is defined as a female germ cell that is not surrounded by a continuous sheet of nurse granulose cells. A "primordial oocyte" is defined as a female germ cell that is surrounded by a single layer of squamous nurse granulosa cells. A "primary oocyte" is defined as a female germ cell that is surrounded by a single layer of cuboidal nurse granulose cells. A "secondary oocyte" is defined as a female germ cell that is surrounded by two layers of cuboidal granulose cells. A "preeantral oocyte" is defined as a female germ cell that is surrounded by three or more layers of granulose cells but without an antral space. An "antral oocyte" is defined as a female germ cell that is surrounded by three or more layers of granulosa cells and contains evidence of antral fluid spaces.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties. As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

"SLLP1" and "SLLP2" are also referred to as "C19" and "C23", respectively.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present invention provides compositions and methods to prevent or inhibit SAS1R function or activity, including the use of SAS1R proteins and fragments and homologs thereof. The present invention further provides compositions and methods utilizing SAS1R, and fragments and homologs thereof, to elicit an immune response against SAS1R. In one aspect, administration of SAS1R or antigenic fragments or homologs thereof results in inhibiting SAS1R. In one aspect, such an immunogenic response and resulting inhibition of SAS1R results in a decrease in fertility.

The following are useful mammalian SAS1R sequences:

```
mouse SAS1R Variant 1, 435 residues (SEQ ID NO: 19)-
MGIMGSLWPWILTMLSLLGLSMGAPSASRCSGVCSTSVPEGFTPEGSPVFQDKD

IPAINQGLISEETPESSFLVEGDIIRPSPFRLLSVTNNKWPKGVGGFVEIPFLLSRK

YDELSRRVIMDAFAEFERFTCIRFVAYHGQRDFVSILPMAGCFSGVGRSGGMQV

VSLAPTCLRKGRGIVLHELMHVLGFWHEHSRADRDRYIQVNWNEILPGFEINFI

KSRSTNMLVPYDYSSVMHYGRFAFSWRGQPTIIPLWTSSVHIGQRWNLSTSDIT

RVCRLYNCSRSVPDSHGRGFEAQSDGSSLTPASISRLQRLLEALSEESGSSAPSGS

RTGGQSIAGLGNSQQGWEHPPQSTFSVGALARPPQMLADASKSGPGAGADSLS
```

-continued

LEQFQLAQAPTVPLALFPEARDKPAPIQDAFERLAPLPGGCAPGSHIREVPRD mouse SAS1R Variant 2 (formerly called ZEP-N), 414 a. a. residues (SEQ ID NO: 6)-
MGAPSASRCSGVCSTSVPEGFTPEGSPVFQDKDIPAINQGLISEETPESSFLVEGDI

IRPSPFRLLSVTNNKWPKGVGGFVEIPFLLSRKYDELSRRVIMDAFAEFERFTCIR

FVAYHGQRDFVSILPMAGCFSGVGRSGGMQVVSLAPTCLRKGRGIVLHELMHV

LGFWHEHSRADRDRYIQVNWNEILPGFEINFIKSRSTNMLVPYDYSSVMHYGRF

AFSWRGQPTIIPLWTSSVHIGQRWNLSTSDITRVCRLYNCSRSVPDSHGRGFEAQ

SDGSSLTPASISRLQRLLEALSEESGSSAPSGSRTGGQSIAGLGNSQQGWEHPPQS

TFSVGALARPPQMLADASKSGPGAGADSLSLEQFQLAQAPTVPLALFPEARDKP

APIQDAFERLAPLPGGCAPGSHIREVPRD mouse SAS1R Variant 3 (formerly called ZEP-Variant 2), 380 a. a. residues (SEQ ID NO: 10)-
MGAPSASRCSGVCSTSVPEGFTPEGSPVFQDKDIPAINQGLISEETPESSFLLSRK

YDELSRRVIMDAFAEFERFTCIRFVAYHGQRDFVSILPMAGCFSGVGRSGGMQV

VSLAPTCLRKGRGIVLHELMHVLGFWHEHSRADRDRYIQVNWNEILPGFEINFI

KSRSTNMLVPYDYSSVMHYGRFAFSWRGQPTIIPLWTSSVHIGQRWNLSTSDIT

RVCRLYNCSRSVPDSHGRGFEAQSDGSSLTPASISRLQRLLEALSEESGSSAPSGS

RTGGQSIAGLGNSQQGWEHPPQSTFSVGALARPPQMLADASKSGPGAGADSLS

LEQFQLAQAPTVPLALFPEARDKPAPIQDAFERLAPLPGGCAPGSHIREVPRD mouse SAS1R Variant 4, 401 a. a. residues (SEQ ID NO: 20)-
MGIMGSLWPWILTMLSLLGLSMGAPSASRCSGVCSTSVPEGFTPEGSPVFQDKD

IPAINQGLISEETPESSFLLSRKYDELSRRVIMDAFAEFERFTCIRFVAYHGQRDF

VSILPMAGCFSGVGRSGGMQVVSLAPTCLRKGRGIVLHELMHVLGFWHEHSRA

DRDRYIQVNWNEILPGFEINFIKSRSTNMLVPYDYSSVMHYGRFAFSWRGQPTII

PLWTSSVHIGQRWNLSTSDITRVCRLYNCSRSVPDSHGRGFEAQSDGSSLTPASI

SRLQRLLEALSEESGSSAPSGSRTGGQSIAGLGNSQQGWEHPPQSTFSVGALARP

PQMLADASKSGPGAGADSLSLEQFQLAQAPTVPLALFPEARDKPAPIQDAFERL

APLPGGCAPGSHIREVPRD mouse SAS1R Variant 5 (formerly called ZEP Variant 1), 392 a. a. residues (SEQ ID NO: 8) -
MGAPSASRCSGVCSTSVPEGFTPEGSPVFQDKDIPAINQGLISEETPESSFLVEGDI

IRPGVSHGVSFPDELSRRVIMDAFAEFERFTCIRFVAYHGQRDFVSILPMAGCFS

GVGRSGGMQVVSLAPTCLRKGRGIVLHELMHVLGFWHEHSRADRDRYIQVN

WNEILPGFEINFIKSRSTNMLVPYDYSSVMHYGRFAFSWRGQPTIIPLWTSSVHI

GQRWNLSTSDITRVCRLYNCSRSVPDSHGRGFEAQSDGSSLTPASISRLQRLLEA

LSEESGSSAPSGSRTGGQSIAGLGNSQQGWEHPPQSTFSVGALARPPQMLADAS

KSGPGAGADSLSLEQFQLAQAPTVPLALFPEARDKPAPIQDAFERLAPLPGGCA

PGSHIREVPRD mouse SAS1R Variant 6, 413 a. a. residues (SEQ ID NO: 21)-
MGIMGSLWPWILTMLSLLGLSMGAPSASRCSGVCSTSVPEGFTPEGSPVFQDKD

IPAINQGLISEETPESSFLVEGDIIRPGVSHGVSFPNELSRRVIMDAFAEFERFTCIR

FVAYHGQRDFVSILPMAGCFSGVGRSGGMQVVSLAPTCLRKGRGIVLHELMHV

LGFWHEHSRADRDRYIQVNWNEILPGFEINFIKSRSTNMLVPYDYSSVMHYGRF

AFSWRGQPTIIPLWTSSVHIGQRWNLSTSDITRVCRLYNCSRSVPDSHGRGFEAQ

-continued

```
SDGSSLTPASISRLQRLLEALSEESGSSAPSGSRTGGQSIAGLGNSQQGWEHPPQS

TFSVGALARPPQMLADASKSGPGAGADSLSLEQFQLAQAPTVPLALFPEARDKP

APIQDAFERLAPLPGGCAPGSHIREVPRD

Human SAS1R nucleic acid sequence-GenBank accession no.
NM_001002036, 1296 by mRNA (SEQ ID NO: 22)-
atggagggtgtaggggtctctggccttgggtgctgggtctgctctccttgccaggtgtg atcctaggagcgcccctggcctccagctgcgcaggagcctgtggtaccagcttcccagat ggcctcacccctgagggaacccaggcctccggggacaaggacattcctgcaattaaccaa gggctcatcctggaagaaaccccagagagcagcttcctcatcgaggggacatcatccgg ccgagtcccttccgactgctgtcagcaaccagcaacaaatgcccatgggtggtagtggt gtcgtggaggtccccttcctgctctccagcaagtacgatgagcccagccgccaggtcatc ctggaggctcttgcggagtttgaacgttccacgtgcatcaggtttgtcacctatcaggac cagagagacttcatttccatcatccccatgtatgggtgcttctcgagtgtggggcgcagt ggagggatgcaggtggtctccctggcgcccacgtgtctccagaagggccggggcattgtc cttcatgagctcatgcatgtgctgggcttctggcacgagcacacgcgggccgaccgggac cgctatatccgtgtcaactggaacgagatcctgccaggctttgaaatcaacttcatcaag tctcagagcagcaacatgctgacgccctatgactactcctctgtgatgcactatgggagg ctcgccttcagccggcgtgggctgcccaccatcacaccactttgggcccccagtgtccac atcggccagcgatggaacctgagtgcctcggacatcacccgggtcctcaaactctacggc tgcagcccaagtggccccaggccccgtgggagagggtcccatgcccacagcactggtagg agccccgctccggcctccctatctctgcagcggcttttggaggcactgtcggcggaatcc aggagccccgaccccagtggttccagtgcgggaggccagcccgttcctgcagggcctggg gagagcccacatgggtgggagtcccctgccctgaaaaagctcagtgcagaggcctcggca aggcagcctcagaccctagcttcctcccaagatcaaggcctggagcaggtgcccccggt gttgctcaggagcagtcctggctggccggagtgtccaccaagcccacagtcccatcttca gaagcaggaatccagccagtccctgtccagggaagcccagctctgccaggggctgtgta cctagaaatcatttcaaggggatgtccgaagattaa Human SAS1R protein-431 amino acids, GenBank accession no.
NP_001002036.3 (SEQ ID NO: 23)-
MEGVGGLWPWVLGLLSLPGVILGAPLASSCAGACGTSFPDGLTPEGTQASGDK

DIPAINQGLILEETPESSFLIEGDIIRPSPFRLLSATSNKWPMGGSGVVEVPFLLSS

KYDEPSRQVILEALAEFERSTCIRFVTYQDQRDFISIIPMYGCFSSVGRSGGMQV

VSLAPTCLQKGRGIVLHELMHVLGFWHEHTRADRDRYIRVNWNEILPGFEINFI

KSQSSNMLTPYDYSSVMHYGRLAFSRRGLPTITPLWAPSVHIGQRWNLSASDIT

RVLKLYGCSPSGPRPRGRGSHAHSTGRSPAPASLSLQRLLEALSAESRSPDPSGS

SAGGQPVPAGPGESPHGWESPALKKLSAEASARQPQTLASSPRSRPGAGAPGV

AQEQSWLAGVSTKPTVPSSEAGIQPVPVQGSPALPGGCVPRNHFKGMSED
```

In one embodiment, the invention provides a pharmaceutical composition comprising a pharmaceutically-acceptable carrier and at least one egg protein, or a homolog, fragment or derivative thereof, wherein said protein is capable of inducing an immune response useful for inhibiting conception in a subject. In one aspect, the invention provides a pharmaceutical composition, wherein said egg protein or peptide comprises an amino acid sequence selected from the group consisting of SEQ ID NOs:6, 8, 10, 19, 20, 21, and 23, and fragments and homologs thereof. In another aspect, the invention provides a pharmaceutical composition further comprising at least one additional egg protein. In one aspect, the additional egg protein is capable of inducing an immune response useful for contraception.

The SAS1R protein, and fragments and homologs thereof, when administered to a subject can inhibit fertilization or conception directly or indirectly. It can inhibit fertilization directly by acting as a competitive inhibitor/binding agent that interacts with SLLP protein on sperm, which in turns prevents SLLP from interacting with native SAS1R on an egg. It can inhibit fertilization or conception indirectly by acting as an immunogen that elicits an immune response against native SAS1R on an egg, wherein the resultant antibodies bind to the native SAS1R and inhibit interaction of SLLP with SAS1R or block SAS1R activity and therefore inhibits fertilization or conception.

In one embodiment, the invention provides a pharmaceutical composition, wherein said pharmaceutical composition comprises at least two different proteins, or homologs, fragments, or derivatives thereof, wherein at least one of said at least two different proteins comprise an amino acid sequence selected from the group consisting of SEQ ID NOs: 6, 8, 10, 19, 20, 21, and 23, and fragments and homologs thereof.

In one embodiment, at least one isolated nucleic acid comprising a nucleic acid sequence encoding an egg protein is administered. In one aspect, the egg protein comprises a sequence selected from the group consisting of SEQ ID NOs: 6, 8, 10, 19, 20, 21, and 23, and fragments and homologs thereof.

An administered protein or a protein expressed by an administered isolated nucleic acid comprising a sequence encoding the protein can act to inhibit SLLP1 and SAS1R interaction or binding.

The present invention also provides for administering at least on SLLP1 protein or biologically active homologs and fragments thereof capable of binding with or interacting with SAS1R and preventing or inhibiting sperm and egg binding and fertilization.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Antibodies and their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

In one embodiment, antibodies, or antisera, directed against SAS1R or a homolog or fragment thereof, are useful for blocking the activity of SAS1R, including its ability to interact with sperm.

Fragments of SAS1R may be generated and antibodies prepared against the fragments. Assays are provided herein to determine whether an antibody directed against SAS1R or a fragment thereof have the ability to inhibit SAS1R activity or function. The assays include measuring the ability of SAS1R to bind with or interact with SLLP proteins, as well as the ability of an antibody to block SAS1R's role in fertilization. For example, in vitro fertilization assays are described herein using an antibody directed SAS1R and this type of assay can be used to test the ability of new antibodies to block SAS1R's function. These same assays can be used to test any compound or agent's ability to disrupt SAS1R's interaction with a SLLP protein or to inhibit fertilization. Protease assays for measuring SAS1R protease activity are also available when needed to confirm that a fragment or homolog of SAS1R maintains the same activity as the parent SAS1R molecule.

Various methods of preparing fragments of SAS1R and making antibodies against SAS1R are available and these methods can be used to map the various regions of SAS1R that are susceptible to inhibition by an antibody.

For example, fragments of SAS1R can be prepared for use as an antigen, such as wherein the antibody binds to one of more fragments comprising amino acids 1-25, 26-50, 51-75, 76-100, 101-125, 126-150, 151-175, 176-200, 201-225, 226-250, 251-275, 276-300, 301-325, 326-350, 351-375, 376-400, and 401-414 of SAS1R Variant 2 (SEQ ID NO:6) or wherein the antibody binds to one or more fragments comprising amino acids 1-25, 26-50, 51-75, 76-100, 101-125, 126-150, 151-175, 176-200, 201-225, 226-250, 251-275, 276-300, 301-325, 326-350, 351-375, 376-400, 401-425, and 426-435 of SAS1R Variant 1 (SEQ ID NO:19) or wherein the antibody binds to amino acids 1-25, 26-50, 51-75, 76-100, 101-125, 126-150, 151-175, 176-200, 201-225, 226-250, 251-275, 276-300, 301-325, 326-350, 351-375, 376-400, 401-425, and 426-431 of SAS1R Variant 1 (SEQ ID NO:23). Such techniques can also be applied to the full-length protein.

Of course, these fragments can also be prepared to yield overlapping sequences and longer and shorter fragments can be prepared. For example, as described herein, interaction experiments between SLLP1 and SAS1R indicate there are at least two binding regions between the two proteins when they interact, which may have different functions. There, fragments encompassing sections of the more N-terminal region of SAS1R or the more C-terminal region of SAS1R can be prepared, such as wherein the antibody binds to amino acids about 1 to about 121 (N-terminal) or an antibody which binds to about 204 to about 414 (more C-terminal) of SAS1R (SEQ ID NO:6) or an antibody which binds to similar regions of SEQ ID NO:23 (human SAS1R).

The antigenic fragments of the proteins of the invention may include peptide antigens that are at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 or up to about 200 amino acids in length. Also included are full-length unprocessed protein as well as mature processed protein. These various length antigenic fragments may be designed in tandem order of linear amino acid sequence of the immunogen of choice, such as SAS1R, or staggered in linear sequence of the protein. In addition, antibodies to three-dimensional epitopes, i.e., non-linear epitopes, can also be prepared, based on, e.g., crystallographic data of proteins. Hosts may also be injected with peptides of different lengths encompassing a desired target sequence. Antibodies obtained from that injection may be screened against the short antigens of SAS1R and against mature SAS1R. Antibodies prepared against a SAS1R peptide may be tested for activity against that peptide as well as the full length SAS1R protein. Antibodies may have affinities of at least about $10^{-6}$M, $10^{-7}$M, $10^{-8}$M, $10^{-9}$M, $10^{-10}$ M, $10^{-11}$M, or $10^{-12}$M toward the SAS1R peptide and/or the full-length SAS1R protein.

In one embodiment, the invention provides a contraceptive vaccine comprising a pharmaceutical composition of the invention, said composition comprising one or more proteins, or variants, homologs, or fragments thereof, comprising an amino acid sequence selected from the group consisting of SEQ ID NOs: 6, 8, 10, 19, 20, 21, and 23, and fragments and homologs thereof, and optionally at least one other egg protein, or a variant, fragment, or homolog thereof.

In one embodiment, the invention provides a method for inhibiting conception in a subject, said method comprising administering to said subject a pharmaceutical composition comprising a pharmaceutically-acceptable carrier and at least one egg protein, or a homolog, fragment or derivative thereof, wherein said protein is capable of inducing an immune response useful for inhibiting conception in a subject. In one aspect, the egg protein comprises an amino acid sequence selected from the group consisting of SEQ ID NOs: 6, 8, 10, 19, 20, 21, and 23, and fragments and homologs thereof.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, Science 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in *Solid Phase Peptide Synthesis*, 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification,* Harcourt Brace Jovanovich, San Diego).

Aptamers

The present invention is also directed to useful aptamers for blocking SAS1R function and activity, and its expression levels. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

The present invention further encompasses the use of phylomers which inhibit or prevent SAS1R function or levels.

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

Methods of Identifying Antagonists and Inhibitors of SAS1R

As used herein, an antagonist or inhibiting agent may comprise, without limitation, a drug, a small molecule, an antibody, an antigen binding portion thereof or a biosynthetic antibody binding site that binds a particular target protein; an antisense molecule that hybridizes in vivo to a nucleic acid encoding a target protein or a regulatory element associated therewith, or a ribozyme, aptamer, or small molecule that binds to and/or inhibits a target protein, or that binds to and/or inhibits, reduces or otherwise modulates expression of nucleic acid encoding a target protein.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

SAS1R assays also include those described in detail herein, such as far-western, co-immunoprecipitation, immunoassays, immunocytochemical/immunolocalization, interaction with SLLP protein, fertilization, contraception, and immunogenicity.

The assays can be performed in a variety of formats, including protein-protein binding assays, biochemical screening assays, high-throughput assays, immunoassays, and cell-based assays, which are well characterized in the art.

All assays for antagonists are common in that they call for contacting the compound or drug candidate with a peptide identified herein under conditions and for a time sufficient to allow these two components to interact.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to a particular peptide identified herein, its interaction with that peptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Complete kits for identifying protein-protein interactions between two specific proteins using the two-hybrid technique are available. This system can also be extended to map protein domains involved in specific protein interactions as well as to pinpoint amino acid residues that are crucial for these interactions.

Compounds that interfere with the interaction of a peptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the peptide may be added to a cell along with the compound to be screened for a particular activity and the ability of the compound to inhibit the activity of interest in the presence of the peptide indicates that the compound is an antagonist to the peptide. The peptide can be labeled, such as by radioactivity.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub. No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable sub-domains (15-50 amino acids long). This technology can be integrated with high throughput screening techniques such as phage display and reverse yeast two-hybrid traps.

The present application discloses compositions and methods for inhibiting the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

Vaccines and Immunogens

In one embodiment, the invention relates to methods and reagents for immunizing and treating a subject with an antigenic compound of the invention such as SAS1R and fragments and homologs thereof, to elicit specific cellular and humoral immune-responses against such specific antigens. The invention provides methods of using specifically prepared immunogen in fresh or lyophilized liposome, proper routes of administration of the immunogen, proper doses of the immunogen, and specific combinations of heterologous immunization including DNA priming in one administration route followed by liposome-mediated protein antigen boost in a different route to tailor the immune responses in respects of enhancing cell mediated immune response, cytokine secretion, humoral immune response, especially skewing T helper responses to be Th1 or a balanced Th1 and Th2 type. For more detail, see Klinefelter (U.S. patent application Ser. No. 11/572,453, which claims priority to international patent application PCT/US2005/026102).

A homolog herein is understood to comprise an immunogenic polypeptide having at least 70%, preferably at least 80%, more preferably at least 90%, still more preferably at least 95%, still more preferably at least 98% and most preferably at least 99% amino acid sequence identity with the naturally occurring SAS1R polypeptides mentioned above and is still capable of eliciting at least the immune response obtainable thereby. A homolog or analog may herein comprise substitutions, insertions, deletions, additional N- or C-terminal amino acids, and/or additional chemical moieties, such as carbohydrates, to increase stability, solubility, and immunogenicity.

In one embodiment of the invention, the present immunogenic polypeptides as defined herein, are glycosylated. Without wishing to be bound by any particular theory, it is hypothesized herein that by glycosylation of these polypeptides the immunogenicity thereof may be increased. Therefore, in one embodiment, the aforementioned immunogenic polypeptide as defined herein before, is glycosylated, having a carbohydrate content varying from 10-80 wt %, based on the total weight of the glycoprotein or glycosylated polypeptide. More preferably said carbohydrate content ranges from 15-70 wt %, still more preferably from 20-60 wt %. In another embodiment, said glycosylated immunogenic polypeptide comprises a glycosylation pattern that is similar to that of the corresponding zona pellucida glycoprotein (or fragment thereof) of the human that is treated. It is hypothesized that this even further increases the immunogenicity of said polypeptide. Thus, it is preferred that the immunogenic polypeptide comprises a glycosylation pattern that is similar to that of the corresponding SAS1R glycoprotein.

In one embodiment, the source of a polypeptide comprises an effective amount of an immunogenic polypeptide selected from SAS1R protein, and immunologically active homologs thereof and fragments thereof, or a nucleic acid sequence encoding said immunogenic polypeptide.

In one embodiment, the present method of immunization comprises the administration of a source of immunogenically active polypeptide fragments, said polypeptide fragments being selected from SAS1R protein fragments and/or homologs thereof as defined herein before, said polypeptide fragments comprising dominant CTL and/or HTL epitopes and which fragments are between 18 and 45 amino acids in length. Peptides having a length between 18 and 45 amino acids have been observed to provide superior immunogenic properties as is described in WO 02/070006.

Peptides may advantageously be chemically synthesized and may optionally be (partially) overlapping and/or may also be ligated to other molecules, peptides, or proteins. Peptides may also be fused to form synthetic proteins, as in Welters et al. (Vaccine. 2004 Dec. 2; 23(3):305-11). It may also be advantageous to add to the amino- or carboxy-terminus of the peptide chemical moieties or additional (modified or D-) amino acids in order to increase the stability and/or decrease the biodegradability of the peptide. To improve immunogenicity, immuno-stimulating moieties may be attached, e.g. by lipidation or glycosylation. To enhance the solubility of the peptide, addition of charged or polar amino acids may be used, in order to enhance solubility and increase stability in vivo.

For immunization purposes, the aforementioned immunogenic polypeptides of the invention may also be fused with proteins, such as, but not limited to, tetanus toxin/toxoid, diphtheria toxin/toxoid or other carrier molecules. The polypeptides according to the invention may also be advantageously fused to heatshock proteins, such as recombinant endogenous (murine) gp96 (GRP94) as a carrier for immunodominant peptides as described in (references: Rapp U K and Kaufmann S H, Int Immunol. 2004 April; 16(4): 597-605; Zugel U, Infect Immun. 2001 June; 69(6):4164-7) or fusion proteins with Hsp70 (Triebel et al; WO9954464).

The individual amino acid residues of the present immunogenic (poly)peptides of the invention can be incorporated in the peptide by a peptide bond or peptide bond mimetic. A peptide bond mimetic of the invention includes peptide backbone modifications well known to those skilled in the art. Such modifications include modifications of the amide nitrogen, the alpha carbon, amide carbonyl, complete replacement of the amide bond, extensions, deletions, or backbone cross-links. See, generally, Spatola, Chemistry and Biochemistry of Amino Acids, Peptides and Proteins, Vol. VII (Weinstein ed., 1983). Several peptide backbone modifications are known and can be used in the practice of the invention.

Amino acid mimetics may also be incorporated in the polypeptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit an immune response against the native SAS1R T cell epitopes. Amino acid mimetics may include non-protein amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.

In one embodiment, the present method comprises the administration of a composition comprising one or more of the present immunogenic polypeptides as defined herein above, and at least one excipient. Excipients are well known in the art of pharmacy and may for instance be found in textbooks such as Remington's pharmaceutical sciences, Mack Publishing, 1995.

The present method for immunization may further comprise the administration, and in one aspect, the co-administration, of at least one adjuvant. Adjuvants may comprise any adjuvant known in the art of vaccination and may be selected using textbooks like Current Protocols in Immunology, Wiley Interscience, 2004.

Adjuvants are herein intended to include any substance or compound that, when used, in combination with an antigen, to immunize a human or an animal, stimulates the immune system, thereby provoking, enhancing or facilitating the immune response against the antigen, preferably without generating a specific immune response to the adjuvant itself. In one aspect, adjuvants can enhance the immune response against a given antigen by at least a factor of 1.5, 2, 2.5, 5, 10, or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a human, thereby excluding immunostimulatory compounds that are endogenous to humans, such as e.g. interleukins, interferons, and other hormones.

A number of adjuvants are well known to one of ordinary skill in the art. Suitable adjuvants include, e.g., incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy-phosphoryloxy)-ethylamine (CGP 19835A, referred to as MTP-PE), DDA (2 dimethyl-dioctadecylammonium bromide), polyIC, Poly-A-poly-U, RIBI™., GERBU™, Pam3™, Carbopol™, Specol™, Titermax™, tetanus toxoid, diphtheria toxoid, meningococcal outer membrane proteins, diphtheria protein $CRM_{197}$. Preferred adjuvants comprise a ligand that is recognized by a Toll-like-receptor (TLR) present on antigen presenting cells. Various ligands recognized by TLR's are known in the art and include e.g. lipopeptides (see, e.g., WO 04/110486), lipopolysaccharides, peptidoglycans, liopteichoic acids, lipoarabinomannans, lipoproteins (from *mycoplasma* or spirochetes), double-stranded RNA (poly I:C), unmethylated DNA, flagellin, CpG-containing DNA, and imidazoquinolines, as well derivatives of these ligands having chemical modifications.

The methods of immunization of the present application further encompass the administration, including the co-administration, of a CD40 binding molecule in order to enhance a CTL response and thereby enhance the therapeutic effects of the methods and compositions of the invention. The use of CD40 binding molecules is described in WO 99/61065, incorporated herein by reference. The CD40 binding molecule is preferably an antibody or fragment thereof or a CD40 Ligand or a variant thereof, and may be added separately or may be comprised within a composition according to the current invention. Such effective dosages will depend on a variety of factors including the condition and general state of health of the patient. Thus, dosage regimens can be determined and adjusted by trained medical personnel to provide the optimum therapeutic or prophylactic effect.

In the present method, the one or more immunogenic polypeptides are typically administered at a dosage of about 1 ug/kg patient body weight or more at least once. Often dosages are greater than 10 ug/kg. According to the present invention, the dosages preferably range from 1 ug/kg to 1 mg/kg.

In one embodiment typical dosage regimens comprise administering a dosage of 1-1000 ug/kg, more preferably 10-500 ug/kg, still more preferably 10-150 ug/kg, once, twice or three times a week for a period of one, two, three, four or five weeks. According to one embodiment, 10-100 ug/kg is administered once a week for a period of one or two weeks.

The present method, in one aspect, comprises administration of the present immunogenic polypeptides and compositions comprising them via the injection, transdermal, or oral route. In another, embodiment of the invention, the present method comprises vaginal administration of the present immunogenic polypeptides and compositions comprising them.

Another aspect of the invention relates to a pharmaceutical preparation comprising as the active ingredient the present source of a polypeptide as defined herein before. More particularly pharmaceutical preparation comprises as the active ingredient one or more of the aforementioned immunogenic polypeptides selected from the group of SAS1R proteins, homologues thereof and fragments of said SAS1R proteins and homologs thereof, or, alternatively, a gene therapy vector as defined herein above.

The present invention further provides a pharmaceutical preparation comprising one or more of the immunogenic polypeptides of the invention. The concentration of said polypeptide in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the immunogenic polypeptides or gene therapy vectors to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

In one embodiment, the present pharmaceutical composition comprises an adjuvant, as defined in more detail herein before. Adjuvants useful for incorporation in the present composition are preferably selected from the group of ligands that are recognized by a Toll-like-receptor (TLR) present on antigen presenting cells, including lipopeptides, lipopolysaccharides, peptidoglycans, liopteichoic acids, lipoarabinomannans, lipoproteins (from *mycoplasma* or spirochetes), double-stranded RNA (poly I:C), unmethylated DNA, flagellin, CpG-containing DNA, and imidazoquinolines, as well derivatives of these ligands having chemical modifications. The routineer will be able to determine the exact amounts of anyone of these adjuvants to be incorporated in the present pharmaceutical preparations in order to render them sufficiently immunogenic. According to another preferred embodiment, the present pharmaceutical preparation may comprise one or more additional ingredients that are used to enhance CTL immunity as explained herein before. According to a particularly preferred embodiment the present pharmaceutical preparation comprises a CD40 binding molecule.

Methods of producing pharmaceutical compositions comprising polypeptides are described in U.S. Pat. Nos. 5,789,543 and 6,207,718. The preferred form depends on the intended mode of administration and therapeutic application.

In one embodiment, the present immunogenic proteins or polypeptides are administered by injection. The parenteral route for administration of the polypeptide is in accordance with known methods, e.g. injection or infusion by intravenous, intraperitoneal, intramuscular, intra-arterial, subcutaneous, or intralesional routes. The protein or polypeptide may be administered continuously by infusion or by bolus injection. A typical composition for intravenous infusion could be made up to contain 10 to 50 ml of sterile 0.9% NaCl or 5% glucose optionally supplemented with a 20% albumin solution and between 10 ug and 50 mg, preferably between 50 ug and 10 mg, of the polypeptide. A typical pharmaceutical composition for intramuscular injection would be made up to contain, for example, 1-10 ml of sterile buffered water and between 10 ug and 50 mg, preferably between 50 ug and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

For convenience, immune responses are often described in the present invention as being either "primary" or "secondary" immune responses. A primary immune response, which is also described as a "protective" immune response, refers to an immune response produced in an individual as a result of some initial exposure (e.g., the initial "immunization") to a particular antigen. Such an immunization can occur, for example, as the result of some natural exposure to the antigen (for example, from initial infection by some pathogen that exhibits or presents the antigen). Alternatively, the immunization can occur because of vaccinating the individual with a vaccine containing the antigen. For example, the vaccine can be a vaccine comprising one or more antigenic epitopes or fragments of SAS1R.

The vaccine can also be modified to express other immune activators such as IL2, and costimulatory molecules, among others.

Another type of vaccine that can be combined with antibodies to an antigen is a vaccine prepared from a cell lysate of interest, in conjunction with an immunological adjuvant, or a mixture of lysates from cells of interest plus DETOX™ immunological adjuvant. Vaccine treatment can be boosted with anti-antigen antibodies, with or without additional chemotherapeutic treatment.

When used in vivo for therapy, the antibodies of the subject invention are administered to the subject in therapeutically effective amounts (i.e., amounts that have desired therapeutic effect). They will normally be administered parenterally. The dose and dosage regimen will depend upon the degree of the infection, the characteristics of the particular antibody or immunotoxin used, e.g., its therapeutic index, the patient, and the patient's history. Advantageously the antibody or immunotoxin is administered continuously over a period of 1-2 weeks. Optionally, the administration is made during the course of adjunct therapy such as antimicrobial treatment, or administration of tumor necrosis factor, interferon, or other cytoprotective or immunomodulatory agent.

For parenteral administration, the antibodies will be formulated in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The antibodies will typically be formulated in such vehicles at concentrations of about 1.0 mg/ml to about 10 mg/ml.

Use of IgM antibodies can be preferred for certain applications; however, IgG molecules by being smaller can be more able than IgM molecules to localize to certain types of infected cells.

There is evidence that complement activation in vivo leads to a variety of biological effects, including the induction of an inflammatory response and the activation of macrophages (Unanue and Benecerraf, Textbook of Immunology, 2nd Edition, Williams & Wilkins, p. 218 (1984)). The increased vasodilation accompanying inflammation can increase the ability of various agents to localize. Therefore, antigen-antibody combinations of the type specified by this invention can be used in many ways. Additionally, purified antigens (Hakomori, Ann. Rev. Immunol. 2:103, 1984) or anti-idiotypic antibodies (Nepom et al., Proc. Natl. Acad. Sci. USA 81: 2864, 1985; Koprowski et al., Proc. Natl. Acad. Sci. USA 81: 216, 1984) relating to such antigens could be used to induce an active immune response in human patients.

The antibody compositions used are formulated and dosages established in a fashion consistent with good medical practice taking into account the condition or disorder to be treated, the condition of the individual patient, the site of delivery of the composition, the method of administration, and other factors known to practitioners. The antibody compositions are prepared for administration according to the description of preparation of polypeptides for administration, infra.

As is well understood in the art, biospecific capture reagents include antibodies, binding fragments of antibodies which bind to activated integrin receptors on metastatic cells (e.g., single chain antibodies, Fab' fragments, F(ab)'2 fragments, and scFv proteins and affibodies (Affibody, Teknikringen 30, floor 6, Box 700 04, Stockholm SE-10044, Sweden; See U.S. Pat. No. 5,831,012, incorporated herein by reference in its entirety and for all purposes)). Depending on intended use, they also can include receptors and other proteins that specifically bind another biomolecule.

The hybrid antibodies and hybrid antibody fragments include complete antibody molecules having full length heavy and light chains, or any fragment thereof, such as Fab, Fab', F(ab')2, Fd, scFv, antibody light chains and antibody heavy chains. Chimeric antibodies which have variable regions as described herein and constant regions from various species are also suitable. See for example, U.S. Application No. 20030022244.

Initially, a predetermined target object is chosen to which an antibody can be raised. Techniques for generating monoclonal antibodies directed to target objects are well known to those skilled in the art. Examples of such techniques include, but are not limited to, those involving display libraries, xeno or humab mice, hybridomas, and the like. Target objects include any substance which is capable of exhibiting antigenicity and are usually proteins or protein polysaccharides. Examples include receptors, enzymes, hormones, growth factors, peptides and the like. It should be understood that not only are naturally occurring antibodies suitable for use in accordance with the present disclosure, but engineered antibodies and antibody fragments which are directed to a predetermined object are also suitable.

The present application discloses compositions and methods for inhibiting the proteins described herein, and those not disclosed which are known in the art are encompassed within the invention. For example, various modulators/ effectors are known, e.g. antibodies, biologically active nucleic acids, such as antisense molecules, RNAi molecules, or ribozymes, aptamers, peptides or low-molecular weight organic compounds recognizing said polynucleotides or polypeptides, as well as the protein itself and fragments thereof.

The present invention further encompasses the identification of functional fragments for the use of SAS1R for use as antigens for contraceptive antibodies as well as its use as an immunogen and as an antifertility vaccine.

In one embodiment, a mimotope analysis of full length SAS1R can be performed by subdividing the sequence into a series of 15 amino acid peptides, with each peptide overlapping by three amino acids. All peptides can be biotinylated and allowed to bind to streptavidin-coated wells in 96-well plates. The reactivity of various antisera can be detected by enzyme-linked immunosorbent assay (ELISA). After blocking non-specific binding, SAS1R antibody can be added sequentially (i.e., either affinity-purified anti-SAS1R or affinity-purified anti-full-length recombinant SAS1R), followed by the sequential addition of peroxidase-conjugated secondary antibody, and peroxidase substrate.

The optical density of each well can be read at 450 nm and duplicate wells averaged. The average value obtained from a similar ELISA using control serum (i.e., preimmune serum) can be subtracted from the test Ig values and the resultant values plotted to determine which linear epitopes are recognized by the Ig.

The second and third components in the strategy to identify functional fragments of SAS1R rely on the synthesis of non-biotinylated peptides corresponding to the epitopes (peptides) predicted by the mimotope analysis. To determine whether any of the epitopes recognized by mimotope analysis are exposed on the egg, immunocytochemical staining with the Ig, without and with each of the peptides, can performed.

Methods for reducing fertility in females using peptides can be found, for example, in Klinefelter (U.S. patent application Ser. No. 11/572,453, filed Feb. 19, 2008, based on international patent application PCT/US2005/026102, filed Jul. 22, 2005).

Pharmaceutical Compositions and Administration

The present invention is also directed to pharmaceutical compositions comprising the compounds of the present invention. More particularly, such compounds can be formulated as pharmaceutical compositions using standard pharmaceutically acceptable carriers, fillers, solublizing agents and stabilizers known to those skilled in the art.

The invention is also directed to methods of administering the compounds of the invention to a subject. In one embodiment, the invention provides a method of treating a subject by administering compounds identified using the methods of the invention description. Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the animal, etc.

Suitable preparations of vaccines include injectables, either as liquid solutions or suspensions, however, solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra arterial, intramedullary, intrathecal, intraventricular, transdermal, subcutaneous, intraperitoneal, intranasal, enteral, topical, sublingual, or rectal means.

In accordance with one embodiment, a method of treating and vaccinating a subject in need of such treatment is provided. The method comprises administering a pharmaceutical composition comprising at least one compound of the present invention to a subject in need thereof. Compounds identified by the methods of the invention can be administered with known compounds or other medications as well.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

A variety of vaginal drug delivery systems is known in the art. Suitable systems include creams, foams, tablets, gels, liquid dosage forms, suppositories, and pessaries. Mucoadhesive gels and hydrogels, comprising weakly crosslinked polymers which are able to swell in contact with water and spread onto the surface of the mucosa, have been used for vaccination with peptides and proteins through the vaginal route previously. The present invention further provides for the use of microspheres for the vaginal delivery of peptide and protein drugs. More detailed specifications of vaginally administered dosage forms including excipients and actual methods of preparing said dosage forms are known, or will be apparent, to those skilled in this art. For example, Remington's Pharmaceutical Sciences (15th ed., Mack Publishing, Easton, Pa., 1980) is referred to.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Other techniques known in the art may be used in the practice of the present invention, including those described in international patent application WO 2006/091535 (PCT/US2006/005970), the entirety of which is incorporated by reference herein.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

Example 1

Materials & Methods

Identification of SAS1R by SPR:

Using purified soluble rSLLP1 as bait, SAS1R was initially identified as a SLLP1 binding partner using mouse oocyte protein lysates.

Purification of Mouse SAS1R and SLLP1:

Mature SAS1R (without signal sequence, 414 a.a.) was cloned by PCR from mouse ovary cDNA, expressed in *E. coli* and purified by affinity column chromatography. SLLP1 was purified as described earlier (2).

Antibody Production and Western Analyses:

Antibody to purified rSAS1R was raised in guinea pigs. Specificity of the antibody was tested against rSAS1R and mouse oocyte extracts following SDS-PAGE and western blotting using HRP-$2^{nd}$ antibody and TMB substrate.

IF Localization of SAS1R in Mouse Ovary:

Fixed ovary sections were probed with anti-SAS1R antibody followed by Cy3-$2^{nd}$ antibody and imaged with UV-microscopy.

IF Microscopy of Oocytes, Early Embryos and Sperm:

Zona intact-, zona free oocytes, early embryos and sperm were collected as before (10), blocked and probed with $1^{st}$ and $2^{nd}$ antibody and imaged with UV-microscopy. For co-LC studies, gametes were incubated with soluble rSAS1R or rSLLP1, washed, probed with $1^{st}$- and $2^{nd}$ antibodies and imaged with UV-microscopy.

Scanning Confocal Microscopy:

Mouse oocytes (GV, M2) and early embryos (2, 4, 8 cell & blastocyst) were further examined. The indirectly IF stained preparations were washed, fixed, permeabilized, treated with RNase, stained with Sytox, mounted in slow-fade and imaged with confocal microscopy.

Localization of SAS1R in Transformed CHO-K1 Cells:

A full length SAS1R construct in pcDNA3.1/V5/His-TOPO vector was used to transform cells, probed with anti-SAS1R or C-terminal V5 antibody following permeabilization or not.

Protease Activity Assay of SAS1R:

Protease activity was assayed with purified soluble rSAS1R using the EnzChek® Peptidase/Protease Assay Kit.

Far-Western Analysis:

Purified rSAS1R on nitrocellulose membrane was overlaid or not with soluble rSLLP1, washed and probed with anti-SLLP1 antibody.

Analysis of SLLP1-SAS1R Interactions by Y2H System 3:

Mature SLLP1 (c-term 128 a.a.) and SAS1R fragments (mature 414 aa without signal peptide, N-term 121 aa and C-term 210 a.a.) were cloned in pGADT7 and pGBKT7 vectors respectively, transformed AH109 yeast cells, grown on low and high stringency selection media and observed for expression of reporter genes.

Co-IP of In Vitro Translated Proteins:

SLLP1 and SAS1R constructs (same as Y2H) were in vitro translated with $^{35}$S-methionine in rabbit reticulocyte lysate and co-IP with tagged monoclonal antibodies from the partner proteins.

Gamete Preparation and IVF:

Epididymal sperm from sexually mature and oocytes from 6 to 8 weeks old ICR mice were used for gamete studies and IVF. Capacitated sperm in presence or absence of rSAS1R were used to inseminate cumulus intact oocytes and fertilization was scored by counting two cell embryos.

Methods for FIGS. 9-15

Identification of SAS1R by Surface Plasmon Resonance (SPR):

Cumulus and zona free mouse oocytes (n=~1000) were suspended in 500 µl of Dulbecco's PBS, freeze-thawed three times over the range −80° C. to 37° C., and then mixed by vortexing. The mixtures were centrifuges for 5 min at 13000×g at room temperature, pellets were discarded and the supernatants were passed over a BIACORE® Sensor Chip CM5 (Biacore AB, Uppsala, Sweden) containing bound soluble recombinant mouse SLLP1 (binding concentration used 1 µg/µl, 200 µl) or no SSLP1 (negative control) at a flow rate of 10 µl/min at 25° C. Following sample binding, the chips were washed in PBS and eluted in 5 µl of 0.1% trifluoroacetic acid at a flow rate of 12 µl/min at 25° C. For each SPR analysis, 7 to 10 samples bound to the chip were collected and pooled. The pooled samples, with volumes ranging from ~35 to 50 µl, were digested with trypsin and analyzed by mass spectrometry in the Biomolecular Research Facility at the University of Virginia. Few proteins were identified as putative ligands and one in particular, SAS1R, showed EST database informatics that indicated specificity to the oocyte and fertilized ovum.

Expression and Purification of Mouse SAS1R and SLLP1:

BLAST analysis of peptide microsequences from mass spectrometry matched a hypothetical 414 amino acid mouse protein, GenBank accession NP_766127, belonging to an astacin-like protein. A mouse ovarian cDNA library (Ambion, TX) was amplified with gene-specific forward and reverse primers containing NdeI and NotI restriction sites, respectively, obtained from Invitrogen (Carlsbad, Calif.). PCR was performed for 40 cycles in a PTC 200 DNA Engine (MJ Research, MA). PCR reaction products were separated on agarose gels, and the amplicon (~1200 base pairs) was gel extracted by the freeze-thaw method and cloned in a pCR2.1-TOPO vector (Invitrogen, CA). Multiple cDNA clones were sequenced in both directions using vector-derived primers on a Perkin-Elmer Applied Biosystems DNA sequencer at the Biomolecular Research Facility, University of Virginia Health System. Inserts were restriction digested, gel purified and cloned into a predigested pET-28b(+) vector at the NdeI and NotI restriction sites. This vector added nucleotides encoding twenty amino acids including a six histidine tag at the N-terminus and ten amino acids including a six histidine tag at the C-terminus. Ligated constructs were used to transform competent cells of *E. coli* strain BL21DE3 (Novagen, WI). A 2 L culture from a single colony was grown to optical density of 0.6 at 600 nm at 37° C. in Luria broth (LB) media. Isopropyl-β-D-thiogalactopyranoside (IPTG) (Sigma, MO) was then added to a final concentration of 1 mM to induce expression. Following 3 h of induction, the bacteria were collected by centrifugation. The recombinant protein was isolated from the insoluble fraction of the *E. coli*, dissolved in 8 M urea in binding buffer (20 mM Tris-HCl, pH 7.9, 5 mM imidazole, and 0.5 M NaCl), and purified by chromatography on a His binding $Ni^{2+}$ chelation affinity resin column (Novagen, NJ). The purified protein fractions were stored at −80° C. until used. Relative protein concentrations were determined by optical density at 280 nm and by Coomassie plus Bradford reagent (Pierce, IL). Mouse SLLP1 was purified as described earlier (2).

Polyclonal Antibody Production and Western Analyses:

Following collection of pre-immune sera by heart puncture, adult male guinea pigs were injected with 150 μg of purified recombinant SAS1R in complete Freund's adjuvant (Sigma). Booster injections were given twice at intervals of 21 days with 150 μg of recSAS1R in incomplete Freund's adjuvant. For all immunizations, one-half of the antigen emulsion was injected intramuscularly in the hind legs and the other half subcutaneously at two super-scapular sites. Animals were exsanguinated by heart puncture 10 days after the third immunization and blood was collected in serum separation tubes (Becton Dickinson, Franklin Lakes, N.J.). After centrifugation at 3200×g for 10 min, the serum was removed, aliquoted, and frozen. Two adult male guinea pigs were injected with the adjuvants lacking SAS1R immunogen on an identical regimen to produce control sera. Specificity of the antisera was tested against recombinant SAS1R protein. Recombinant SAS1R protein (50 ng/lane) was solubilized in Laemmli buffer (2×), and proteins were resolved on a 12% SDS-PAGE (Criterion™, Bio-Rad) gel at 20 mA. Proteins were then blotted to nitrocellulose membrane (0.2 μm, Bio-Rad), and all blots were blocked with 5% nonfat dry milk in phosphate buffered saline with 0.05% Tween 20 (PBST) for 45 min at room temperature. For immunoblotting, 1:25,000 or 1:50,000 dilutions of the anti-recombinant SAS1R guinea pig sera were incubated for two hours. The blots were then washed three times for 10 min in PBST, incubated with a 1:5000 dilution of peroxidase-conjugated donkey anti-guinea pig IgG secondary antibody for 1 h, and washed two times for 10 min in PBST and three times for 10 min in PBS. The blots were then developed in TMB peroxidase substrate (3,3',5,5'-tetramethylbenzidine; KPL, Md.).

This antiserum was also tested against mouse oocyte extracts following 1D SDS-PAGE and western blotting. Oocytes (150/lane) from super-ovulated mice were solubilized in Laemmli buffer and proteins were resolved on a 12% SDS-PAGE gel at 20 mA. Proteins were then blotted to nitrocellulose membranes and were blocked with 5% nonfat dry milk in PBST for 30 min at room temperature. For immunoblotting, a 1:1,000 dilution of guinea pig anti-recombinant SAS1R serum was incubated overnight. Blots were washed three times for 10 min in PBS-T and incubated with a 1:2500 dilution of peroxidase-conjugated goat anti-guinea pig IgG secondary antibody for 1 hour. The blots were then washed twice for 10 min in PBST and three times for 10 min in PBS and were developed in TMB peroxidase substrate.

Indirect Immunofluorescent (IF) Localization of SAS1R in the Mouse Ovary:

Ovaries were collected from superovulated mice, fixed in 4% paraformaldehyde for 24 hrs, embedded in paraffin, and sectioned, and the resulting specimens were mounted on glass slides. At five minute intervals the slides were serially rehydrated by successive immersions in microclear (xylene) twice, absolute ethanol twice, 95% ethanol, 80% ethanol, 70% ethanol, and double distilled water. Specimens were blocked with 10% NGS (Normal Goat Serum) in PBS for 30 min in a humid chamber and incubated with guinea pig anti-recombinant SAS1R polyclonal antibody (1:200) in 0.1% NGS/PBS overnight at 4° C. Slides were thrice washed with PBS for 5 min and incubated with secondary goat anti-guinea pig/Cy3 Red antibody (1:200) (Jackson ImmunoResearch, PA) in 0.1% NGS/PBS for 1 h at 37° C. in the dark. Slides were washed thrice for five min with PBS, mounted with slow-fade reagent (Molecular Probes, CA), coverslips sealed with nail polish, and specimens visualized under a Carl Zeiss Standard 18 ultraviolet microscope. Images were captured using MrGrab 1.0 (Carl Zeiss Vision GmbH, Germany).

Indirect IF Microscopy of Oocytes, Early Embryos, and Sperm:

The fate of SAS1R during early development was studied by standard indirect immunofluorescence microscopy. Metaphase II eggs and subsequent embryonic stages including 2, 4, 8 cells and blastocyst stages, were obtained as described earlier (15) and incubated with 5% NGS/TYH media for 30 min. Oocytes and early embryos were incubated with guinea pig anti-recombinant SAS1R polyclonal antibody (1:200) in 0.1% NGS/media for 1 h at 37° C. and 5% $CO_2$. Preparations were washed five times and incubated with goat anti-guinea pig/Cy3 Red antibody (1:200) (Jackson ImmunoResearch, PA) in 0.1% NGS/media for 1 h at 37° C. and 5% $CO_2$, washed again, mounted in media on glass slides, and visualized under a Zeiss Standard 18 ultraviolet microscope as above.

Mouse oocytes were also examined for co-localization of SLLP1 binding sites and SAS1R localization. Oocytes were incubated with gradually increasing concentrations (0-100 μg/ml) of recombinant SLLP1 for 1 h, and then oocytes were washed five times and incubated with guinea pig anti-recombinant SAS1R polyclonal antibody (1:200) and rat anti-recombinant SLLP1 polyclonal antibody (1:200), simultaneously, in 0.1% NGS/media for 1 h at 37° C. and 5% $CO_2$. Oocytes were washed five times and incubated with goat anti-guinea pig/Cy3 Red antibody (1:200) (Jackson ImmunoResearch, PA) and goat anti-rat/FITC Green antibody (1:200) (Jackson ImmunoResearch, PA), in 0.1% NGS/media for 1 h at 37° C. and 5% $CO_2$. Oocytes were washed and mounted in media on glass slides. SLLP1 and SAS1R images were captured separately with MrGrab 1.0 (Carl Zeiss Vision GmbH, Germany) on the Zeiss Standard 18 ultraviolet microscope and were merged digitally to evaluate their respective localizations.

Similarly capacitated mouse sperm were also examined for co-localization of SAS1R binding sites and SLLP1 localization. Sperms were incubated with increasing concentrations (0-100 μg/ml) of rSAS1R for 1 h, then sperm were washed two times at 700 g for 8 min and droplets were made on glass slide. These droplets were air-dried for 30 min and rehydrated again with 20 μl of PBS for 5 min. Now in the droplets, sperm were fixed with 20 μl of 4% paraformaldehyde for 25 min and then washed with 20 μl of PBS thrice for 5 min each. Now the droplets were blocked with 10% NGS for 30 min and incubated with guinea pig antirSAS1R polyclonal antibody (1:200) and rat anti-rSLLP1 polyclonal antibody (1:200) simultaneously, in 0.1% NGS/media for 1 h at 37° C. and 5% $CO_2$. All the droplets were washed three times and incubated with goat anti-guinea pig/Cy3 red antibody (1:200, Jackson ImmunoResearch, PA) and goat anti-rat/FITC green antibody (1:200, Jackson ImmunoResearch, PA), in 0.1% NGS/media for 1 h at 37° C. and 5% $CO_2$. Sperms were washed and mounted in media on glass slides. SLLP1 and SAS1R images were captured separately with MrGrab 1.0 (Carl Zeiss Vision GmbH, Germany) on the Zeiss Standard 18 ultraviolet microscope and were merged digitally to evaluate their respective localizations.

Scanning Confocal Microscopy:

Mouse oocytes and early embryos were also studied by scanning confocal microscopy. The preparations were washed three times in PBS containing 1% BSA (PBS/BSA) and then fixed in 4% paraformaldehyde in PBS-polyvinyl-alcohol (PVA) for 20 min at room temperature. Following fixation, oocytes and embryos were washed 5 times in PBS/BSA and permeabilized with 0.5% Triton X-100 in PBS for 20 min at room temperature. Specimens were washed five times in PBS/BSA, placed in 0.4 mg/ml RNase (Sigma, USA) in PBS/BSA for 30 min, and stained with 20 nM Sytox (Molecular Probes, CA) for 10 min. Oocytes and embryos were then extensively washed, placed in slow-fade equilibration media (Molecular Probes, USA) for about 1 min, and then mounted on slides in slow fade mounting media. Images were obtained on a Zeiss 410 Axiovert 100 Microsystems LSM confocal microscope. For each panel, 4-sec scans were averaged four times per line using a 63× oil lens equipped with a zoom factor of two. Attenuation, contrast, brightness, and pinhole aperture remained constant.

Localization of SAS1R in Transformed CHO-K1 Cells:

Full length SAS1R was cloned into pcDNA3.1/V5/His-TOPO vector (Invitrogen, CA) from a PCR product generated from a mouse ovary cDNA library (Ambion, TX) using gene-specific forward and reverse primers. PCR reaction products were separated on agarose gels, and the amplicon was gel extracted by freeze-thawing and cloned. Multiple cDNA clones were sequenced in both directions using vector-derived primers on a Perkin-Elmer Applied Biosystems DNA sequencer to verify the insert sequence.

Adherent Chinese hamster ovary (CHO-K1) cells maintained in Ham's F-12 nutrient medium (F12-Ham 1×; Invitrogen, CA) supplemented with fetal calf serum (10% v/v) and 1 mM sodium pyruvate were used for all transfection experiments. Cells were maintained at 37° C. in a humidified 5% $CO_2$ atmosphere and the media changed every second day. The day before transfection, cells were seeded on 6-well plates containing poly-D-lysine coated 12 mm round coverslips (BD BioCoat™ Cellware, Franklin Lakes, N.J.), and were used at approximately 50-70% confluence. Cells were transfected with Lipofectamine™ 2000 (pDNA: lipofectamine; 4 µg: 10 µl, per well) in a final volume of 500 µl of Opti-MEM (Invitrogen, CA). Cells were then incubated at 37° C. for 5 h after which the media containing the transfection complex was removed. After transfection, the cells were washed in PBS, supplemented with F12 media, and incubated for 48 h.

The cells were fixed briefly with 4% paraformaldehyde in phosphate-buffered saline (PBS), blocked with 10% FBS (Fetal Bovine Serum) in PBS for 30 min, and a cohort permeabilized with 0.05% NP-40. Cells were incubated on the cover slips with anti-SAS1R guinea pig polyclonal antibody for 1 h or mouse anti-V5 tag monoclonal antibody, and immune-complexes were visualized with fluorescein isothiocyanate (FITC)-conjugated donkey anti-guinea pig or mouse antibody (Jackson ImmunoResearch Laboratories, PA). Cover slips were mounted with slowfade (Molecular Probes, CA), sealed with nail polish, and visualized by ultraviolet microscopy as noted above.

Protease Activity Assay of SAS1R:

Protease activity was assayed in serial dilutions (0-2000 ng) of purified bacterial recombinant SAS1R using the EnzChek® Peptidase/Protease Assay Kit (Molecular Probes, OR), which provides a FRET (fluorescence resonance energy transfer)-based method for quantitation of a wide range of protease activities. This assay was performed in 100 µl size reactions and repeated three times with varying concentrations of recombinant SAS1R. Fluorescence was measured over 24 h following the manufacturer's protocol. Protease activity of recombinant SAS1R appeared within 1 h and increased within 24 h. SLLP1 was used as a negative control. The assay method was validated using purified trypsin as a positive control (Sigma, MO).

Far-Western Analysis Between SAS1R and SLLP1:

Purified recombinant SAS1R was resolved by SDS-PAGE and transferred to nitrocellulose membranes. The membrane was probed with c-terminal anti-his monoclonal antibody and developed with TMB. Duplicate SAS1R blotted strips were overlaid with mouse rSLLP1 or not (with 5 µg/ml in blocking buffer i.e., 5% milk in PBS with 0.05% Tween 20 [PBST]) for 90 min at room temperature. Before protein overlay, the strips were incubated with blocking buffer for 1 h. Following overlay, the strips were incubated with either anti-SLLP1 (ADD2) monoclonal antibody for 1 h in blocking buffer. After washing in PBST (×4), the strips were probed with goat anti-mouse HRP secondary antibody in blocking buffer for 1 h, washed in PBST (×4) followed by PBS (×1), and developed with TMB.

Analysis of SLLP1-SAS1R Interactions by Yeast Matchmaker Two-Hybrid (Y2H) System 3:

Protein—protein interactions between mouse SLLP1 and mouse SAS1R were studied in the advanced GAL4 based yeast two-hybrid system 3 (Clontech, CA). The mature, mSLLP1 protein (C-terminal 128 residues) was cloned as a fusion to the GAL4 activation domain in the pGADT7 vector utilizing EcoRI and BamHI sites. Full-length mouse SAS1R (414 residues, without signal sequence), an N-terminal SAS1R protein (121 residues), and a C-terminal 210 residue protein were each fused to the GAL4 DNA-binding domain in the pGBKT7 vector utilizing EcoRI and BamHI sites. The plasmids were amplified in TOP10 E. coli cells (Invitrogen, CA) using ampicillin (pGADT7 vector) or kanamycin (pGBKT7 vector) at 50 µg/ml.

To test interactions between the constructs, strain AH109 yeast cells were made competent using 1×TE/1×LiAc and PEG/LiAc solutions (following the manufacturer's protocol), transformed with single, double, or empty constructs, and plated on low stringency (LS) and high stringency (HS) plates. The low stringency selection plates were deficient in tryptophan and leucine, and this selection confirmed the co-transformation by both plasmids which supplied the missing amino acids in the pGBKT7 and pGADT7 vectors, respectively. The high stringency plates were deficient of adenine and histidine in addition to tryptophan and leucine, and this was used for evaluation of interaction between the test plasmids. This yeast two-hybrid system 3 uses the expression of three reporter genes—ADE2, HIS3, and MEL1 (or LacZ)—under the control of distinct GAL4 upstream activating sequences and TATA boxes. The ADE2 and HIS3 reporters provide strong nutritional selections to the yeast strain, AH109. Furthermore, the expression of MEL1 gene (an endogenous GAL4-responsive gene), which encodes a secretory α-galactosidase enzyme, was used to screen and visualize the blue colonies indicative of positive interaction by incorporating X-α-gal directly into the stringent culture plates. The cells were grown at 30° C. for 5 to 6 days. The experiments were repeated 3 times.

Co-Immunoprecipitation (Co-IP) of In Vitro Translated Proteins:

Interactions between SLLP1 and SAS1R were evaluated using in vitro translated proteins from rabbit reticulocyte lysates labeled with $^{35}$S-methionine. The pGADT7 and pGBKT7 expression plasmids, which encode N-terminal HA and N-terminal c-Myc epitopes, respectively, were employed to produce radiolabeled SLLP1 and SAS1R recombinant proteins in vitro, utilizing the Quick Coupled Transcription/Translation (TNT) system (Promega, WI). The TNT reactions were performed for 90 min at 30° C. in 1.5 ml Eppendorf tubes containing the plasmid (≤2 μg), TNT reaction buffer, T7 RNA polymerase, an amino acid mixture lacking methionine, RNasin ribonuclease inhibitor, rabbit reticulocyte lysate, and $^{35}$S-methionine (GE Healthcare, NJ) in 50 μl aliquots per the manufacturer's protocol. The profile of the radiolabeled proteins was analyzed by SDS-PAGE (15% gels) using 5 μl of TNT product along with 15 μl of 2× reducing sample buffer (Pierce, IL). Following electrophoresis, the gels were fixed (50% methanol, 10% glacial acetic acid and 40% $H_2O$) for 30 min, equilibrated in 20% ethanol/10% glycerol for 30 min, dried between sheets of cellophane for 1 h (GelAir drying system, Bio-Rad, CA), and exposed to image intensifying phosphor screens. The ionizing radiation profiles were imaged using a PhosphorImager (Storm 860, GE Healthcare, NJ) and analyzed by ImageQuant software.

High affinity anti-c-Myc and anti-HA monoclonal antibodies coupled to agarose beads were employed to immunoprecipitate proteins (IP) and their radiolabeled putative interacting partners (Co-IP) using the Profound c-Myc/HA Tag IP/Co-IP system (Pierce, IL). For Co-IP reactions, the specific TNT products, ranging from 7-23 μl were gently mixed and kept at 4° C. for 1 h. Simultaneously the anti-c-Myc and anti-HA antibody beads were incubated with 5% milk in PBST (phosphate buffer saline with 0.05% Tween 20) for 1 h at 4° C. in Handy spin columns (Pierce, IL) with gentle end-over-end mixing to prevent loss of beads during the subsequent steps. Following blocking, the antibody beads were incubated with IP or Co-IP samples overnight at 4° C. in Handee spin columns with gentle end-over-end mixing. The beads were then precipitated and washed 3 times in 500 μl of PBST at 4000×g for 10 sec with 3 gentle mixes during each wash. The IP and co-IP products were then recovered from the beads in 23 μl of 2× non-reducing sample buffer, heated at 99° C. for 5 min, centrifuged, and mixed with 2 μl of β-mercaptoethanol, and 20 μl of this mixture was loaded per lane for SDS-PAGE analysis using Criterion gels (Bio-Rad, CA). After electrophoresis, the gels were fixed, air dried, exposed to phosphor screens, and imaged as described above for analysis of TNT products.

Gamete Preparation and In Vitro Fertilization:

ICR mice were used in all experiments. Suspensions of epididymal spermatozoa from sexually mature male mice were prepared for insemination of isolated oocytes. Oocytes were obtained from 6 to 8 weeks old females superovulated with 10 IU PMSG and 10 IU hCG, injected intraperitoneally at 48 h intervals. Females were killed 16 h after hCG injection, and both oviducts were immediately removed, placed in mineral oil, and flushed to recover oocytes.

In vitro fertilization was conducted with cumulus intact oocytes using sperm dispersed from cauda epididymides. Sperm were placed for 5 min in 200 μl drops of fertilization medium under paraffin oil. The sperm suspension was diluted to a concentration of $10^6$ sperm/ml in a volume of 200 μl and then incubated for 120 min in a humidified tissue culture incubator (37° C., 5% $CO_2$ in air) to allow capacitation. The spermatozoa were incubated with varying concentrations (0-100 μg/ml) of purified rSAS1R for the last 60 min of capacitation. Cumulus masses were placed in 135 μl drops of fertilization medium (one mass per drop) under paraffin oil, and fifteen microliters of the sperm suspension (final: $10^5$ sperm/nil) was added to each cumulus mass drop. Thus, recombinant protein was present in the incubation droplet during gamete interaction. Six hours following insemination, oocytes were relocated to 100 μl drops of fertilization medium under mineral oil. Following overnight incubation, eggs were stained in 10 μg/ml Hoechst dye for 10 min and washed 3 times in fertilization medium. The eggs were then placed in 5 μl of fertilization medium between a microscope slide and an elevated coverslip, and visualized at 160× using light and fluorescence microscopy (Zeiss Axioplan). Two-cell embryos were scored as fertilized, while one-celled oocytes were scored as unfertilized.

Isoimmunization of Female Mice: Female mice received five injections at intramuscular and intraperitoneal sites with 40 μg of purified recombinant SAS1R in complete Freund's adjuvant (primary immunization) or incomplete Freund's adjuvant (booster immunizations) at weeks 1, 3, 5, 7 and 9. Sera were collected on weeks 2, 4, 6, 8 and 10. Anti-SAS1R titers were checked after the $3^{rd}$, $4^{th}$ and $5^{th}$ bleeds by ELISA using 100 ng of recombinant SAS1R in 100 mM carbonate—bicarbonate buffer, pH 9.6 (Kurth et al., 2008) and by immunofluorescence microscopy on oocytes as noted above.

Results:

Identification of SAS1R:

To identify SLLP1 putative oolemmal receptor(s), ligand affinity panning was performed with mouse egg lysate using soluble rSLLP1 as bait using surface plasmon resonance (SPR). Peptide analysis of eluted proteins matched to several proteins including an oocyte specific protein, SAS1R. Six SAS1R splice variants were cloned with three signal sequences (FIGS. 9 and 10). All six variants contained the zinc binding active site motif, a characteristic of zinc dependent metalloproteases, and a putative transmembrane domain. Three SAS1R variants (V1, V4, and V6) revealed a putative signal sequence followed by a predicted cleavage site between residues SMG-AP. SAS1R variants revealed deletions of 34 residues from exons 4 and 5 (V3, V4) or deletion and insertion in exon 5 (V5, V6). Variants 5 and 6 showed 31 a.a. deletions and 9 a.a. insertion in the $5^{th}$ exon.

SAS1R was found to be conserved among mammals (FIG. 10, 67% identity to human) and its homologs can be traced to lower invertebrates (identity, 42% zebrafish; 36% nematode). Alignment reveals conservation of signal peptide and the zinc binding signatures.

Proform sizes: V1—435-421 a.a. [G-A]; V2—414 (SEQ ID NO:6); V3—380; V4—402-381 [G-A]; V5—392; V6—413-390 [G-A].

The Zn metal ion binding catalytic pocket is underlined in FIG. 9. The consensus motif HELMHVLGFWH (SEQ ID NO:24) with histidine residues for Zn coordination and conserved catalytic residue, E [glutamic acid], forms part of the catalytic pocket along with a tyrosine zinc ligand embedded in the motif SVMHY (SEQ ID NO:25). These consensus motifs have residues which can be substituted with any amino acid that does not ablate the activity, i.e., HEXX-HXXGXXH (SEQ ID NO:26) and SXMHY (SEQ ID NO:27).

The Zn binding active site cleft in SAS1R is formed by two distinct N-terminal and C-terminal domains on either side and lined by evolutionarily conserved histidine residues. Of four highly conserved histidines, three (H161, H165, and H171) are predicted with high confidence to be involved in Zn coordination.

SAS1R isoforms and protease assay:

The mature rSAS1R (414 residues; SEQ ID NO:6) was expressed in E. coli with histidine tag and purified by affinity chromatography. The purified rSAS1R revealed two major bands (~50 & ~25 kD) and several minor bands (FIG. 1A). The ~25 kD band was found to be a 210 residue C-terminal fragment of SAS1R by Edman degradation (FIG. 9; begins at a.a. residue position 226, Variant 1). Each of the affinity purified bands identified by Coomassie staining immunoreacted with anti-his antibody confirming them as rSAS1R proteins. The C-terminal fragments appear to result from proteolysis during purification.

Guinea pig anti-rSAS1R recognized the rSAS1R proteins (FIG. 1A, L4; e.g., ~50 kD, ~25 kD). Protein extracts from zona-intact and zona-free mouse eggs showed microheterogeneity of immunoreactive bands of native SAS1R between ~51 and ~31 kD (FIG. 1A, L5; 11, L2), with major bands of ~45 and ~31 kD and minor bands of ~51, ~49 and ~42 kD. Pre-immune control antibody showed no reactivity to rSAS1R or egg extracts (FIG. 11A). SAS1R microheterogeneity likely corresponds to isoforms derived from the six splice variants, which are predicted to encode proteins of 47.4, 45.2, 44.8, 42.5, 43.7 and 41.4 kD, while the lower ~31 kD protein may be a processed form following endoproteolytic cleavage. The presence of masses higher than those of deduced from primary sequences suggest post-translational modifications of SAS1R isoforms. The identical SAS1R profile between zona free and zona intact oocytes, suggest that native SAS1R isoforms reside predominately with the oocyte and not with zona pellucida.

Purified rSAS1R was tested for protease activity using a fluorescent conjugated synthetic peptide substrate (FIG. 1B). rSAS1R exhibited dose dependent proteolytic activity assayed by fluorescence resonance energy transfer (FRET) method over the range 200-2000 ng. rSAS1R demonstrated protease activity within one hour (FIG. 11B) and the hydrolysis were linear until 24 h (FIG. 1B). Mouse rSLLP1 purified by identical procedures to rSAS1R from same E. coli strain was used as a negative control. The results also indicated that E. coli expressed rSAS1R refolded sufficiently to retain proteolytic activity.

Figure 2:
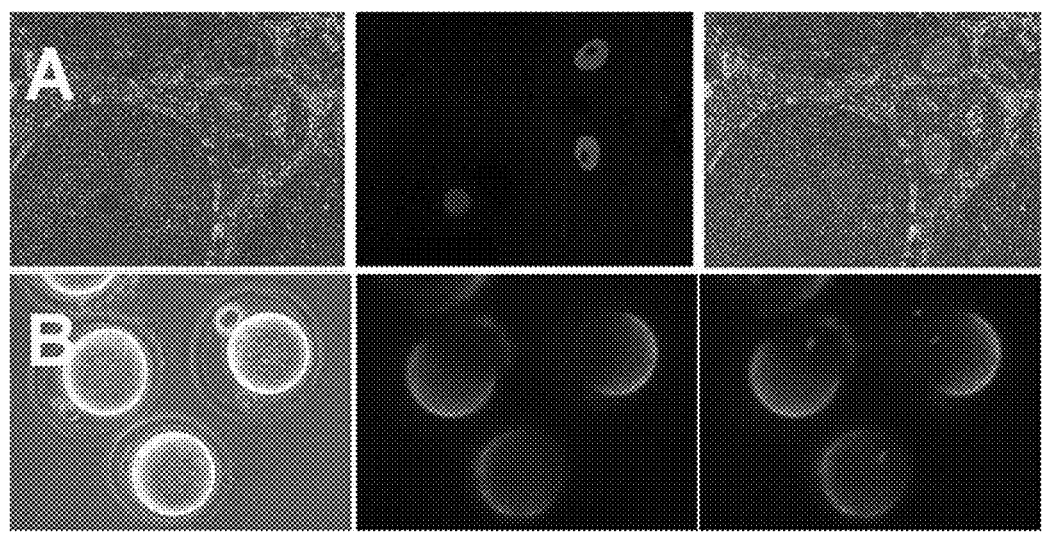
FIG. 2: IF localization of SAS1R in ovary and oocytes. (A) SAS1R localized specifically to oocyte cytoplasm within primary, secondary and Graafian follicles. (B) In unpermeabilized zona-intact ovulated M2 oocytes, SAS1R concentrated in a dome shaped microvillar domain on the surface of oocyte plasma membrane. Eccentric nuclei (blue) were antipodal to the SAS1R positive domain. Panels: left, phase; middle, fluorescence; right, merge.

Oocyte Specific Microvillar Surface Expression of SAS1R:

Using indirect immunofluorescence (IF), SAS1R was localized exclusively in oocyte cytoplasm (FIG. 2A, 12A). SAS1R was not localized in oocytes within primordial follicles but was first detected in primary follicles with maximum staining intensity noted in secondary follicles and relatively less in large antral follicles. This indicated that, within ovarian tissues, SAS1R is specific to the oocyte. IF of live, zona-intact and zona-free ovulated M2 oocytes prior to fertilization showed that SAS1R was localized asymmetrically on the oocyte surface (FIG. 2B, 12C), being concentrated in a dome corresponding to the oolemmal microvillar region (6) which is antipodal to the eccentric nucleus. The concentrated SAS1R staining on the microvillar surface was similar whether the zona pellucida was intact or absent.

Parallel studies found that SAS1R is localized in live human eggs retrieved for in vitro fertilization purposes.

Figure 3:
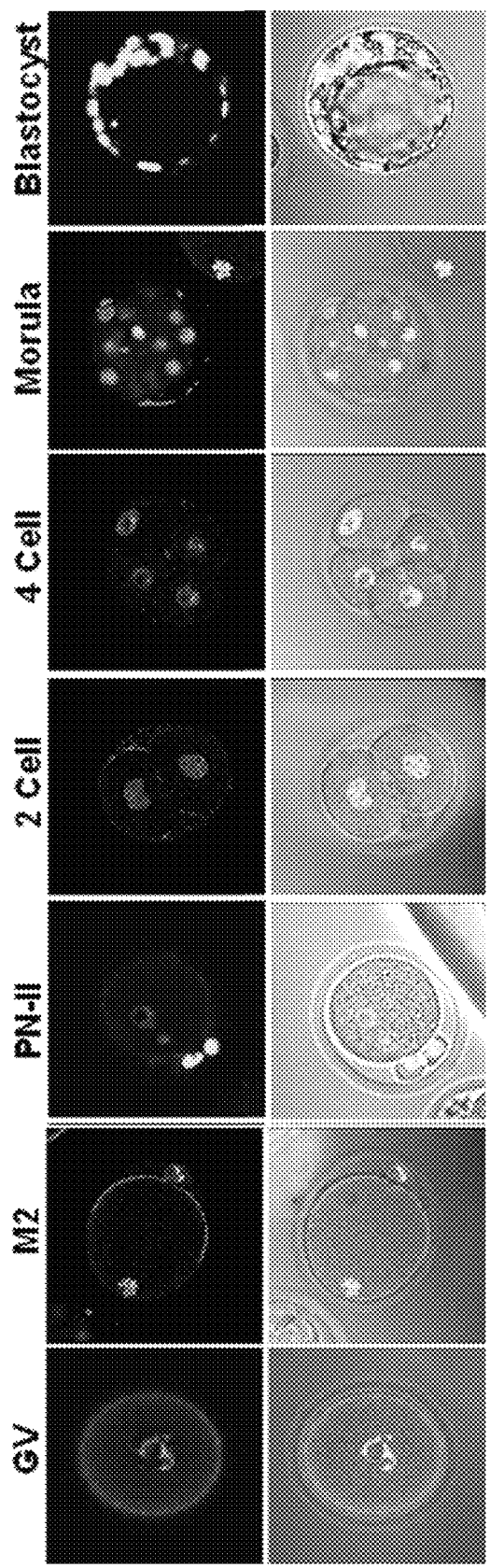
FIG. 3: Confocal localization of SAS1R, before and after fertilization. Oocytes and cultured early embryos stained with SAS1R antibody (red) and with Sytox (for nucleus, green; upper panel; merged on phase images, lower panel). SAS1R was localized uniformly in the cytoplasm of the GV oocyte where it concentrated at the cell periphery. After polar body formation, in M2 oocyte SAS1R localized mainly in the microvillar domain of oolemma. In fertilized oocytes (PN-II), SAS1R was located only in punctate regions at the cell periphery. These small patches persisted from 2-cell to morula stages when SAS1R appeared within the PVS. SAS1R was virtually undetectable in blastocyst stages.

SAS1R Confocal Localization in Oocyte and Early Embryo:

In ovulated GV stage oocytes, SAS1R was observed throughout the ooplasm and was particularly concentrated at the oocyte periphery (FIG. 3, GV). In M2 phase oocytes, SAS1R was concentrated in the microvillar domain of the oolemma antipodal to the M2 nucleus and in the membrane of the first polar body. The observations imply that in the GV to M2 transition, a re-orientation of membrane components including SAS1R takes place. Observations of zygotes with two pronuclei revealed that SAS1R was no longer polarized in the microvillar domain but now showed only weak staining of the plasma membrane (PN-II). In 2-cell through morulae stages diffuse, punctuate SAS1R staining was observed mainly in the perivitelline space (PVS), but occasionally on the oolemma. This low level of diffuse, punctate staining remained mainly in the PVS through early blastocyst stage and then disappeared in late blastocyst stages. Thus, SAS1R demonstrated the greatest intensity of staining in the plasma membranes of GV and M2 oocytes, which suggested SAS1R plays its main role at the oocyte surface of pre-zygotic stages of development. Subsequently, the protein appeared to aggregate in the membrane of early zygote and then to be shed into the PVS.

Figure 13:
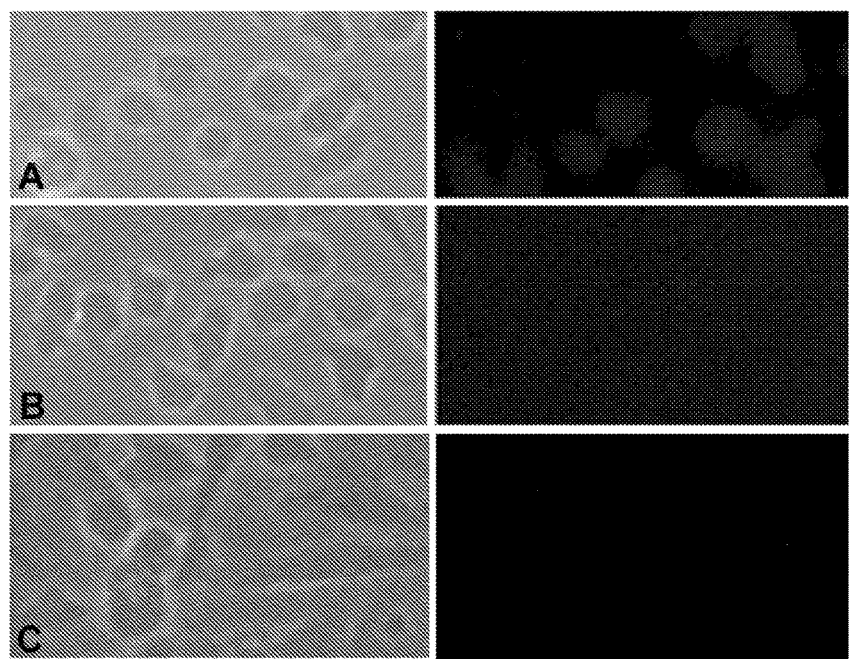
FIG. 13: Control SAS1R expression in transfected CHO-K1 cells. The cells were transfected with pcDNA3.1-TOPO vector without any SAS1R construct and probed with SAS1R specific antibodies. (A) Fixed and permeabilized cells probed with SAS1R antibody showed no IF signal (control of FIG. 3A). (B) Fixed and unpermeabilized CHO-K1 cells probed with SAS1R antibody showed no IF signal (control of FIG. 3B). (C) Fixed and permeabilized cells probed with anti-V5 monoclonal antibody revealed no IF signal (control of FIG. 3C). Panels: left—phase; right—immunofluorescence image.

SAS1R is a Membrane Protein:

Full length SAS1R with a C-terminal V5 tag was expressed in mammalian CHO-K1 cells and the protein was localized in permeabilized and unpermeabilized transfected cells by IF. The anti-rSAS1R antibody localized SAS1R in the cytoplasm and on the cell membranes of permeabilized cells and at the cell membrane of unpermeabilized cells (FIG. 4A, 4B). Interestingly, SAS1R was concentrated asymmetrically in unpermeabilized transfected cells where it localized in regions where blebs and lamellipodia were noted by phase contrast microscopy (arrows). Unpermeable CHO-K1 cells did not stain with anti-V5 antibody to the C-terminal tag (data not shown), whereas permeable CHO-K1 did stain (FIG. 4C). The results suggested that the C-terminus of SAS1R is cytoplasmic and the N-terminus is extracellular in orientation. Together, these observations support the conclusion that SAS1R is a protein that translocates to the plasmalemma. The control cells transfected with blank vector showed no staining (FIG. 13).

Protein Protein Interactions Between SAS1R and SLLP1: SPR Analysis:

As noted earlier, SAS1R was first identified by SPR as a putative partner protein for the sperm acrosomal ligand SLLP1 (FIG. 9).

Figure 5:
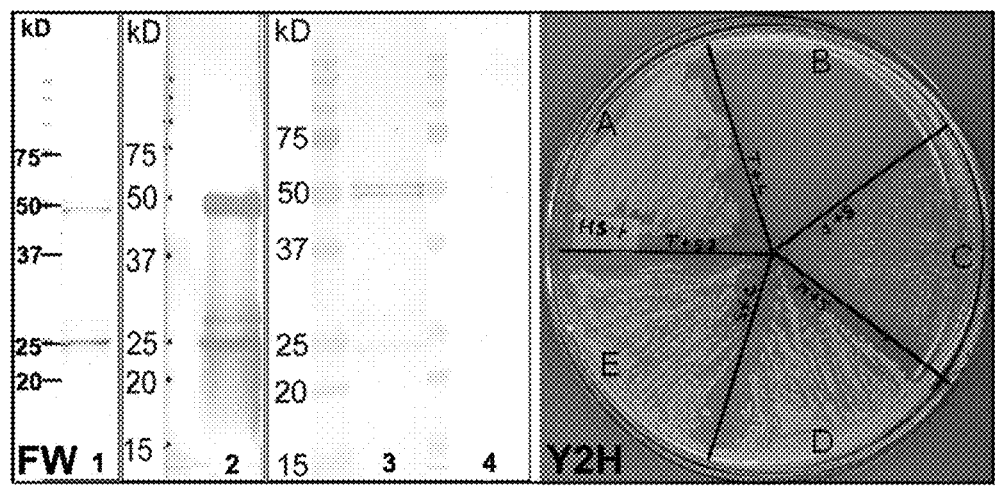
FIG. 5: SAS1R-SLLP1 interaction analyses by Far-Western (FW) and Y2H. (FW) Profile of purified rSAS1R stained with Coomassie used for FW analysis (L 1). Western of rSAS1R probed with anti-his tag antibody (L 2). rSAS1R blot was either overlaid (L 3) or not overlaid (L 4) with purified soluble rSLLP1 (5 µg/ml) and probed with anti-SLLP1 monoclonal antibody. Full length SAS1R (~51, ~50 kD) binds to rSLLP1 however, the equal intensity C-terminal ~25 kD protein bound rSLLP1 very weakly. (Y2H) Y2H assay showing affinity between SLLP1 and SAS1R fragments. Growth of yeast cells on high stringency plate forming blue colonies indicated interaction between the partner proteins. (A) Positive interaction between SV40 large T-antigen and its murine partner p53. (B) Negative interaction between large T-antigen and human Lamin C. (C) Very weak interaction between full length SAS1R and SLLP1 with few small colonies but none in 3 days (see FIG. 14). (D) Positive interaction between N-terminal SAS1R and SLLP1. (E) Positive interaction between C-terminal SAS1R and SLLP1.

Far-Western Analysis:

Affinity between SAS1R and SLLP1 was studied by far-western analysis with purified rSAS1R and rSLLP1. Purified rSAS1R was resolved by SDS-PAGE, stained with Coomassie (FIG. 5, FW1) and also transferred to nitrocellulose membranes. A blot probed with C-terminal anti-His tag monoclonal antibody, identified the specific rSAS1R bands (FIG. 5, FW2), including the full length and truncated proteins. Additional blots were either overlaid or not with rSLLP1, washed and probed with monoclonal antibody to SLLP1 (FIG. 5, FW, 3, 4). The FW revealed that SLLP1 interacted strongly with the full length SAS1R doublet (~51, ~50 kD) but very weakly to the C-terminal fragment (~25 kD) [of equal intensity], indicating that the N-terminus of SAS1R is important to the conformation of the SLLP1 binding domain than the C-terminus alone.

Figure 14:
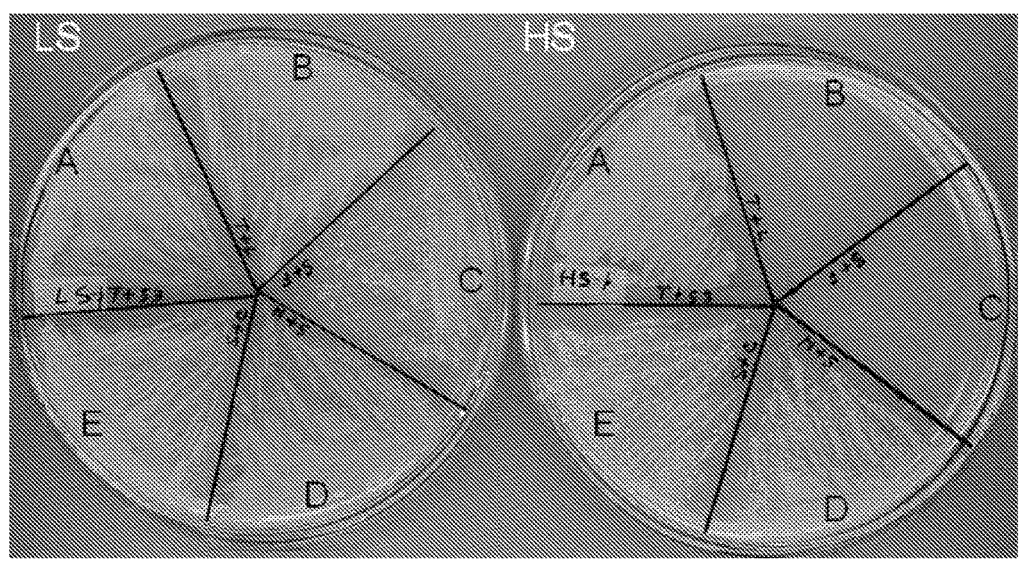
FIG. 14: Yeast two hybrid analyses of SAS1R-SLLP1 interaction. Yeast strain AH109 cells were grown on low stringency (LS) and high stringency (HS) plates containing X-gal transformed with both SLLP1 and SAS1R constructs. Growth on LS plate devoid of tryptophan and leucine confirms transfection by both constructs. Growth on HS plate devoid of tryptophan, leucine, adenine, and histidine along with formation of blue colonies reveals interaction between given protein constructs. The plates were examined after three days of transfection. (A) Positive interaction between SV40 large T-antigen and its partner p53, as a positive control. (B) Negative interaction between large T-antigen and human Lamin C, as a negative control. (C) Negative interaction between SLLP1 and SAS1R full length. (D) Positive interaction between SLLP1 and SAS1R N-terminus. (E) Positive interaction between SLLP1 and SAS1R C-terminus.

Yeast Two Hybrid (Y2H) Analysis:

The Y2H system under stringent selection conditions was used to study the affinity between SLLP1 and three SAS1R constructs: full-length 414 residues (V2; SEQ ID NO:6), N-terminal 121 residues, and C-terminal 210 residues. Successful co-transfection by both plasmid constructs was confirmed by survival on the low stringency plate (FIG. 14). Protein-protein interactions were confirmed by survival and formation of blue colonies on high stringency plates. Yeast cells co-transfected with SLLP1 and N-terminal SAS1R showed the fastest rescue with strongest blue color by 3 and 5 days (FIG. 5D, 14D). Co-transfection of C-terminal SAS1R and SLLP1 also rescued the cells within three days (FIG. 14E, HS); however, co-transfection of full length SAS1R with SLLP1 did not rescue the yeast cells in 3 days but only weakly in 5 days (FIG. 5C, 14). The relative lack of full-length SAS1R interaction with SLLP1 is likely due to the presence of the putative transmembrane domain in SAS1R as membrane proteins are known to be incapable of nuclear transport and proper folding leading to weaker or no interaction in the yeast system (19, 20). The results in the Y2H system confirm the strong molecular interaction between N-terminal SAS1R and SLLP1.

Figure 15:
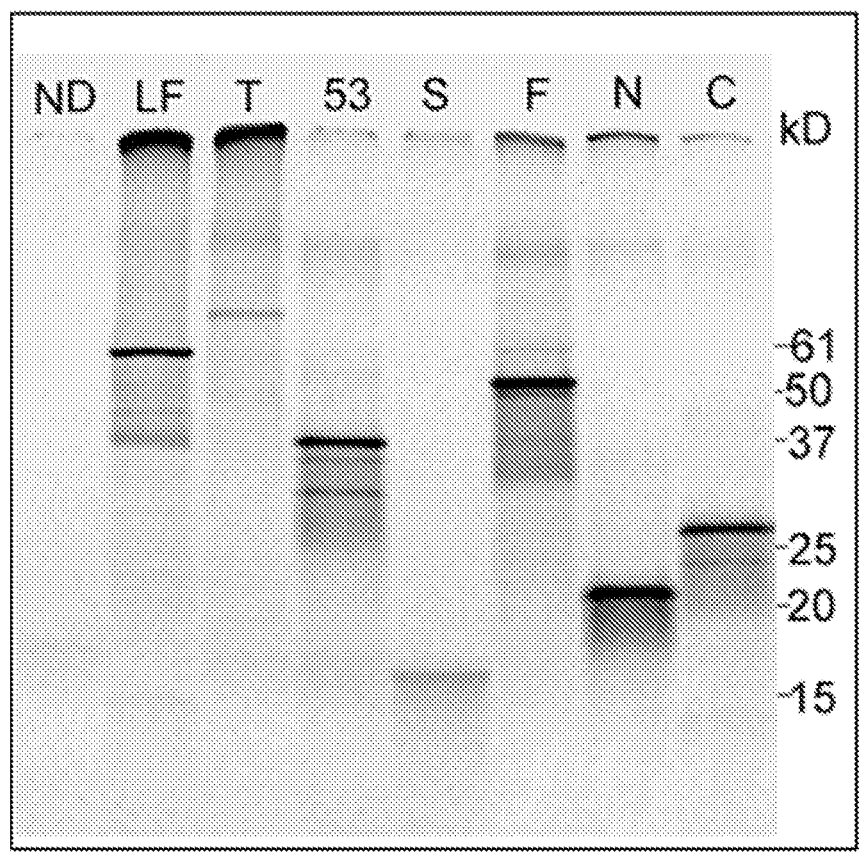
FIG. 15: Autoradiogram of in vitro translated SLLP1 and SAS1R constructs used in co-immunoprecipitation analyses (FIG. 6). Each construct was translated in presence of $^{35}$S-methionine using rabbit reticulocyte lysate and resolved by SDS-PAGE. In 50 μl reactions, the following proteins were synthesized: ND, no protein control; LF, luciferase translation control; T, large T-antigen; 53, p53 partner protein of T-antigen; S—SLLP1; F—SAS1R full length; N—SAS1R N-terminus; C—SAS1R C-terminus. Each translated protein contained a major band that resolved at the expected size on SDS-PAGE analysis.

Co-Immunoprecipitation (Co-IP) Studies:

To further study interactions between SAS1R and SLLP1, co-IP was performed with $^{35}$S-methionine labeled recombinant constructs. The in vitro translated N-, C-, full length SAS1R and p53 contained myc-tags while SLLP1 and T-antigen had HA-tags and each produced a major band at expected masses (FIG. 15). SLLP1 (~16 kD) was pulled down by co-IP with anti-myc tag antibody to SAS1R full length, N- and C-terminal fragments (FIG. 6A). In the reverse co-IP, SAS1R full length (~50 kD), N- (~21 kD) and C-terminal (~26 kD) fragments were pulled down by anti-HA antibody to SLLP1 (FIG. 6B). The IPs of SLLP1 and SAS1R constructs were performed with HA-tag and myc-tag antibodies, respectively. As a positive control, the T-antigen was pulled down by co-IP with p53 tagged myc antibody. Together, the results indicate that SLLP1 has interacting domains with SAS1R.

Figure 7:
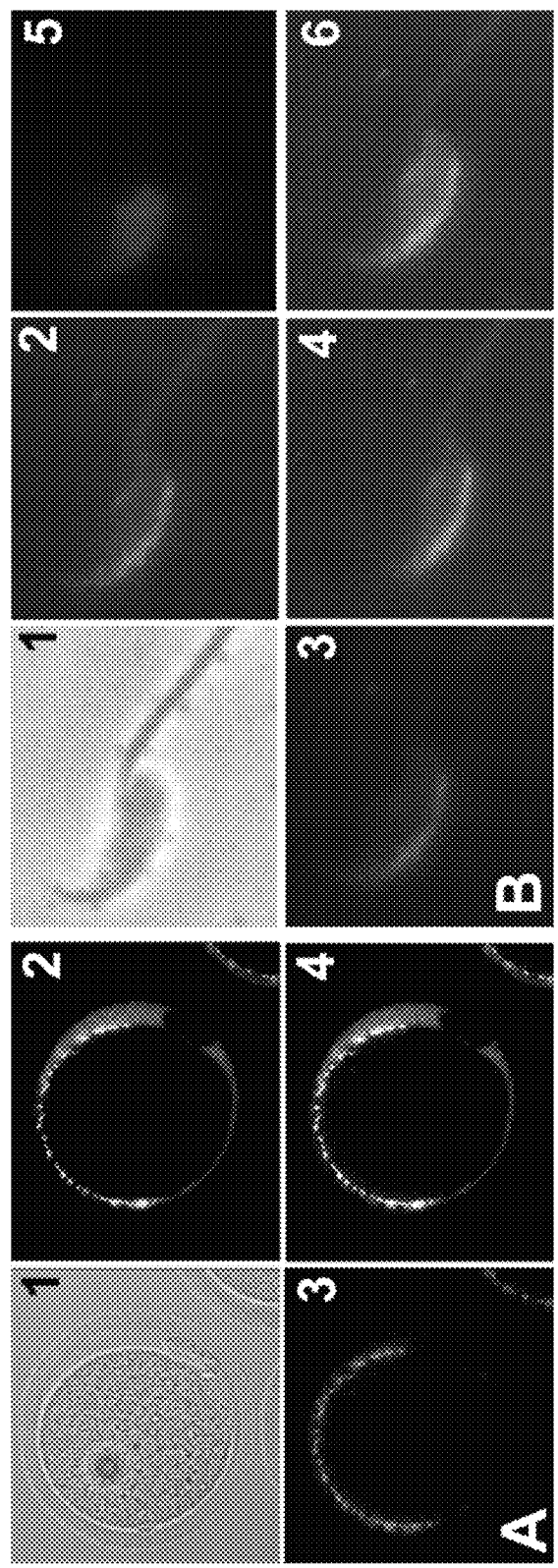
FIG. 7: Co-localization of rSLLP1 and rSAS1R in gametes. (A) M2 oocytes incubated with rSLLP1, washed and probed with SLLP1 and SAS1R antibodies. SLLP1 predominantly co-localized to the microvillar region of the mouse oolemma marked by SAS1R localization. (B) Capacitated sperm incubated with rSAS1R, washed and probed with both antibodies. SAS1R co-localized to sperm acrosomal domain, the site of SLLP1 localization. The sperm nucleus was stained with DAPI. Panels: 1, phase; 2, SLLP1; 3, SAS1R; 4, merge of 2 & 3; 5, nucleus; 6, merge of 4 & 5.
Figure 8:
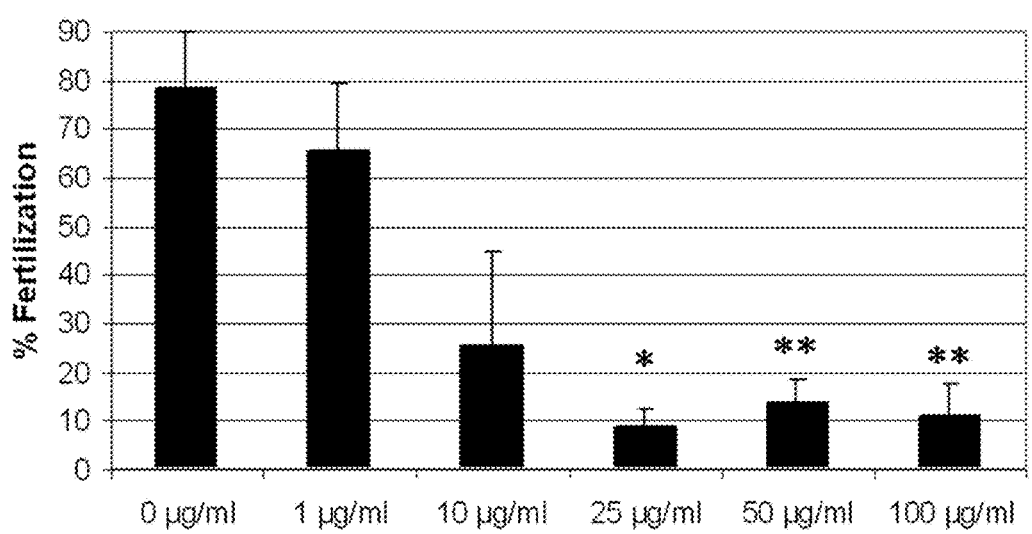
FIG. 8: Inhibition of mouse fertilization by rSAS1R. Capacitated mouse sperm were incubated with varying concentrations of rSAS1R prior to fertilization of cumulus intact oocytes. The percentage of fertilized eggs decreased with increased concentration of SAS1R. Significant P-value differences from no protein control were marked with asterisks (**, $P<0.01$; *, $P<0.03$). N=3 experiments at each concentration.
Figure 11:
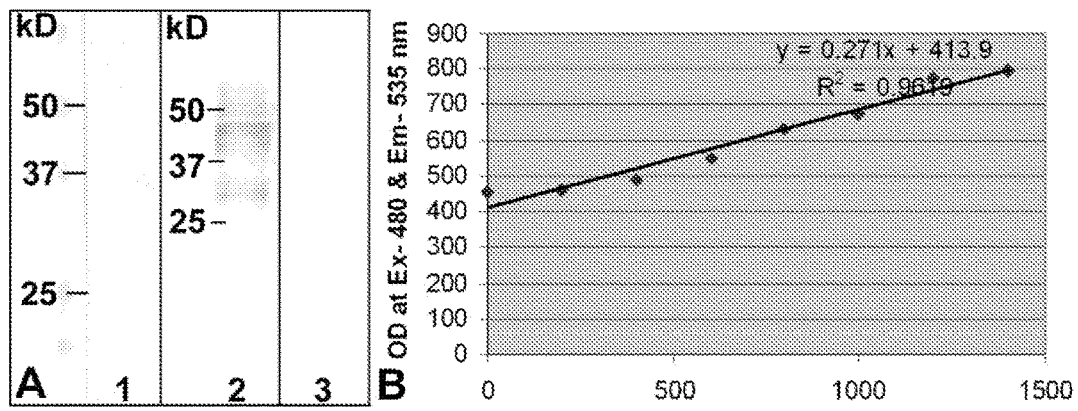
FIG. 11: Oocyte Western and protease activity assay of SAS1R. (A) Western analysis of rSAS1R probed with SAS1R preimmune antibody (L 1) showing no immunoreactivity. Western analysis of zona free oocytes probed with immune (L 2) and preimmune (L 3) SAS1R antibody. The SAS1R Western profile of zona free oocytes was very similar to zona intact oocytes (FIG. 1, L 5). (B) Protease activity assay of rSAS1R using fluorescent tagged synthetic peptide as a substrate. Varying concentration of rSAS1R (multiples of 0.2 μg) was used in 100 μl assay system for 1 h. The released fluorophore following cleavage of the peptide bond was measured by FRET based method at an excitation and emission of 480 and 535 nm, respectively. A concentration dependent hydrolysis of the synthetic peptide was observed with rSAS1R (♦, correlation, $R^2$=0.96).
Figure 12:
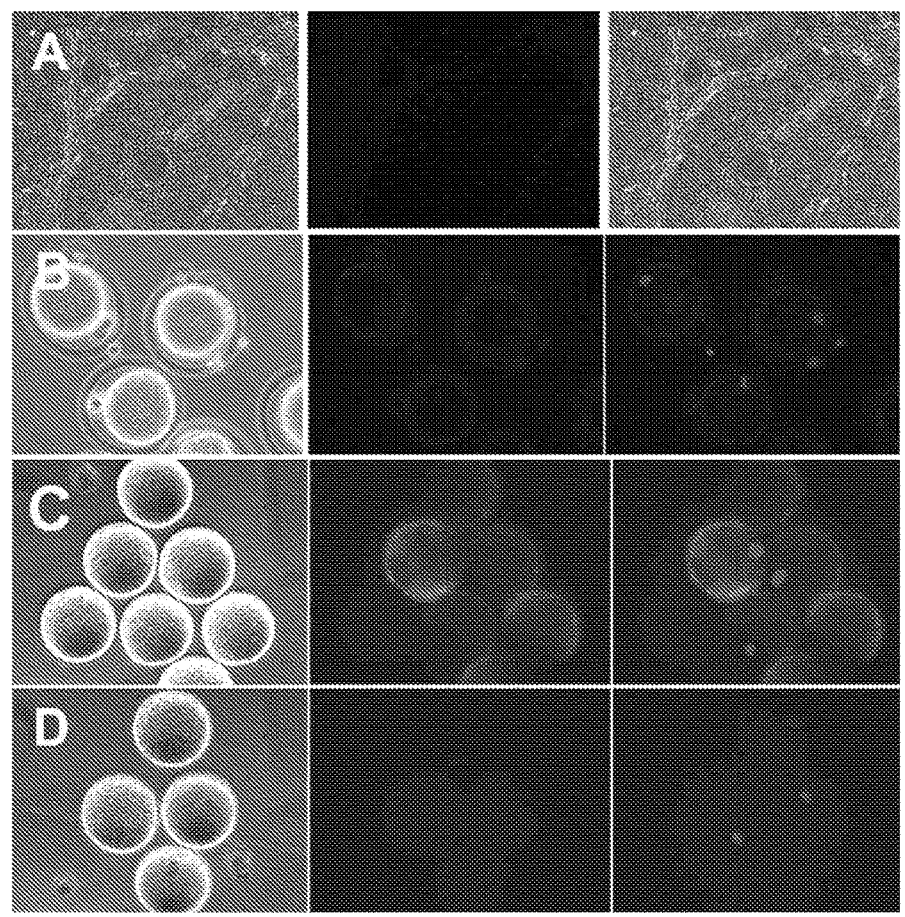
FIG. 12: Immunofluorescent (IF) localization of SAS1R in zona free M2 oocytes and controls. (A) Control IF localization of SAS1R in adult ovary section probed with preimmune antibody showing lack of specific signal (control of FIG. 2A). (B) Control IF of zona intact unpermeabilized oocytes probed with SAS1R preimmune antibody indicating lack of specific signal (control of FIG. 2B). (C) IF localization of SAS1R in zona free unpermeabilized M2 oocytes probed with anti-SAS1R antibody. DAPI (blue) stained areas indicate M2 arrested eccentrically positioned nuclei opposite to the microvillar domain decorated with SAS1R expression. (D) Control zona free unpermeabilized oocytes stained with preimmune antibody showed no immunoreactivity. Panels: left, phase; middle, fluorescence; right, merge image.

Co-Localization of SAS1R and SLLP1:

To determine if SAS1R and SLLP1 co-localize on gametes, M2 oocytes or capacitated sperm were incubated with each purified recombinant proteins, washed, and probed with both antibodies. SAS1R signals were present strongly in the microvillar region of the oolemma and weakly in PVS of the oocyte, and co-localized with the major SLLP1 signal, which also diffusely stained the PVS (FIG. 7A). The diffuse staining of SLLP1 and SAS1R in the PVS is consistent with the presence of oolemmal microvilli and CD9 in PVS of M2 oocytes (21). Conversely, SLLP1 localized in the anterior acrosomal region of sperm, and the SAS1R binding sites were observed to precisely co-localize with SLLP1 (FIG. 7B). In sum, native SAS1R co-localizes with rSLLP1 binding sites on the oocyte membrane and native SLLP1 co-localizes with rSAS1R binding sites on the sperm acrosomal membrane indicating shared domains of specific interaction.

rSAS1R Inhibits In Vitro Fertilization (IVF):

To determine the role of mouse SAS1R during IVF, capacitated spermatozoa were pre-incubated with rSAS1R prior to insemination (FIG. 8). A statistically significant reduction in fertilization was observed in samples treated with 25 μg/ml (89% reduction, P≤0.03) or more of SAS1R. While a reduction was noted at 10 μg/ml, this was not statistically significant. When sperm were incubated with no protein, fertilization was not reduced. These observations are in agreement with the previous inhibition of mouse IVF by rSLLP1 (2). Together, the results suggested a role of SAS1R in fertilization.

Verification of Results Using Native SAS1R and Native SLLP1

Further experiments were done showing that native SLLP1 and native SAS1R interact with one another. For example, it was shown that native mSLLP1 binds to mSAS1R microvillar domain in a co-localization study in zona intact mouse MII oocytes. In that study, native mouse cauda sperm extract in PBS was incubated with zona intact mouse M2 egg and probed with guinea pig anti-SAS1R or rat anti-SLLP1 immune or pre-immune sera followed by probing with fluorescent conjugated secondary antibodies (data not shown).

In another study using native proteins, it was demonstrated using co-localization techniques that native acrosomal mouse SLLP1 binds to SAS1R in zona intact oocytes (data not shown).

In yet another study, the interaction of native mSAS1R and native mSLLP1 was further verified using co-immunoprecipitation techniques and a rat antibody directed against mSLLP1, using a sperm-egg extract, followed by western analysis using a guinea pig antibody directed against mSAS1R. It was found that following mixing sperm and egg extracts, that the anti-SLLP1 antibody was able to precipitate a complex of SAS1R and SLLP1, as demonstrated in the western blot (data not shown).

These experiments provide further support for those described above.

Figure 4:
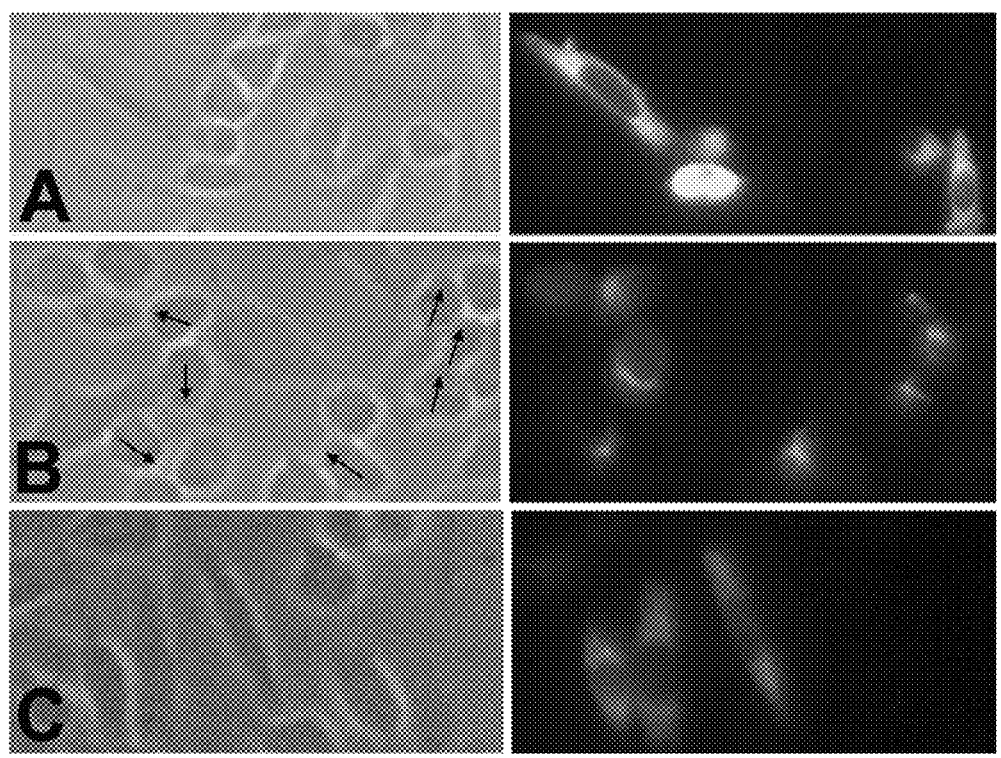
FIG. 4: SAS1R expression on the cell surface of transfected CHO-K1 cells. (A) In fixed and permeabilized cells SAS1R localized to cytoplasmic and surface domains. (B) Polarized localization (arrows) of SAS1R at the cell surface in fixed, unpermeabilized cells confirming that SAS1R is a membrane protein. (C) Fixed and permeabilized cells probed with SAS1R C-terminal V5 tag antibody showing its expression in the cytoplasm. Panels: left—phase, right—fluorescence.
Figure 6:
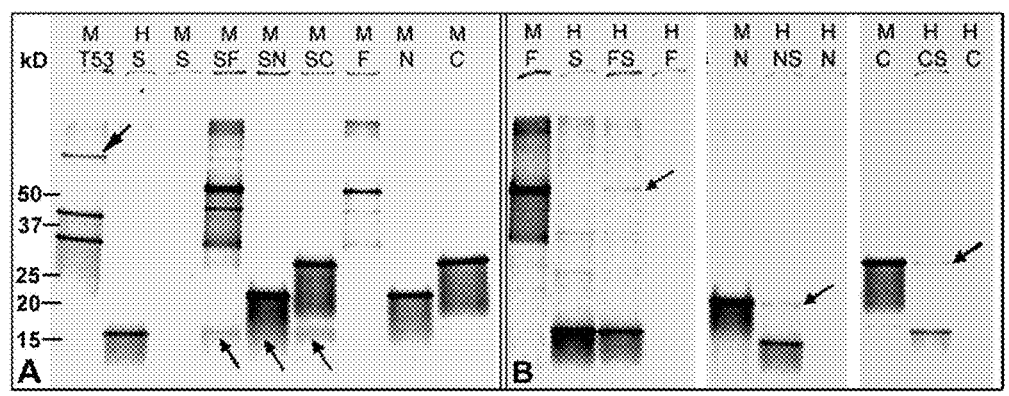
FIG. 6: Co-Immunoprecipitation of SAS1R and SLLP1. Proteins were synthesized by in vitro translation in presence of $S^{35}$-methionine and analyzed by SDS-PAGE (FIG. 15). Translated SAS1R full length (F), N-terminus (N), C-terminus (C) and p53 (53) had Myc-tag (M) while T-antigen (T) and SLLP1 (S) had HA-tag (H). (A) Co-Immunoprecipitation of T-antigen or SLLP1 using Myc-tag antibody from partner proteins. (B) Co-Immunoprecipitation of SAS1R full length, N-terminal and C-terminal proteins using HA-tag antibody from partner protein. The co-immunoprecipitation products were marked by arrows. The IPs of SLLP1 and SAS1R constructs were done using HA- and Myc-tag antibodies respectively.

Discussion:

SAS1R is an Oolemmal SLLP1 Receptor:

Five lines of biochemical evidence support the hypothesis that SAS1R is an oolemmal receptor for the intra-acrosomal ligand SLLP1. First, native SAS1R extracted from oocytes specifically bound to and was eluted from rSLLP1 bait from SPR chip (FIG. 9). Second, rSLLP1 bound to rSAS1R in far western analyses (FIG. 5). Third, molecular affinity between SAS1R and SLLP1 was demonstrated in the Y2H assay system (FIG. 5), a eukaryotic model. Fourth, SAS1R-SLLP1 interactions were shown by co-IP of SAS1R with antibody against SLLP1, and the converse, using eukaryotic in vitro translation system (FIG. 6). Fifth, co localization of rSLLP1 binding and SAS1R expression profile on oocyte membrane (FIG. 7A) was consistent with the binding of rSLLP1 to native SAS1R (FIG. 9), while the converse study demonstrated the co-localization of rSAS1R and SLLP1 on the acrosomal membrane of capacitated sperm (FIG. 7B). The oolemmal localization of SAS1R in mature oocytes is also supported by surface localization of SAS1R in unpermeabilized CHO-K1 cells (FIG. 4). Furthermore, the rSAS1R/rSLLP1 binding to opposite gametes is also strengthened by their ability to inhibit fertilization of cumulus intact oocytes (FIG. 8, (2)). Noteworthy, both SLLP1 and SAS1R are gamete specific molecules and both are exposed prior to sperm-egg fusion. Both Far-western and Y2H studies suggest that the SAS1R N-terminus binds SLLP1 more strongly than the C-terminus. Together these lines of evidence support the hypothesis that SAS1R is an oolemmal receptor that binds the sperm ligand SLLP1.

SAS1R is an Oocyte Specific Oolemmal Protein:

EST databases show expression of SAS1R exclusively in the ovary, oocyte, and zygote in mice suggesting a tight spatial and temporal regulation of SAS1R gene expression. In mouse ovary, immunolocalizations showed the SAS1R protein is confined to ooplasm of primary, secondary and Graafian follicles. Thus, available evidence both at protein and mRNA levels supports the conclusion that SAS1R is specifically expressed only in the oocyte and early embryo, suggesting it is a maternal gene expressed during oogenesis.

Dynamic Re-Localization of SAS1R to the Microvillar Domain:

SAS1R was localized throughout the ooplasm of germinal vesicle stage oocytes and was particularly concentrated symmetrically in a corona at the oocyte periphery. SAS1R subsequently localized to the microvillar domain of the oolemma in M2 arrested ovulated oocytes, being detected at the cell surface of live oocytes. These observations indicate that a dynamic re-organization of the SAS1R domain occurs as the oocyte matures following meiosis I and the two distinct regions of the oocyte plasma membrane form; i.e., the amicrovillar region overlying the eccentric meiotic spindle, and the microvillar region (6). The development of this polarity with respect to SAS1R is particularly noteworthy, as sperm bind to and fuse with the oolemma in the microvillar region.

Figure 16:
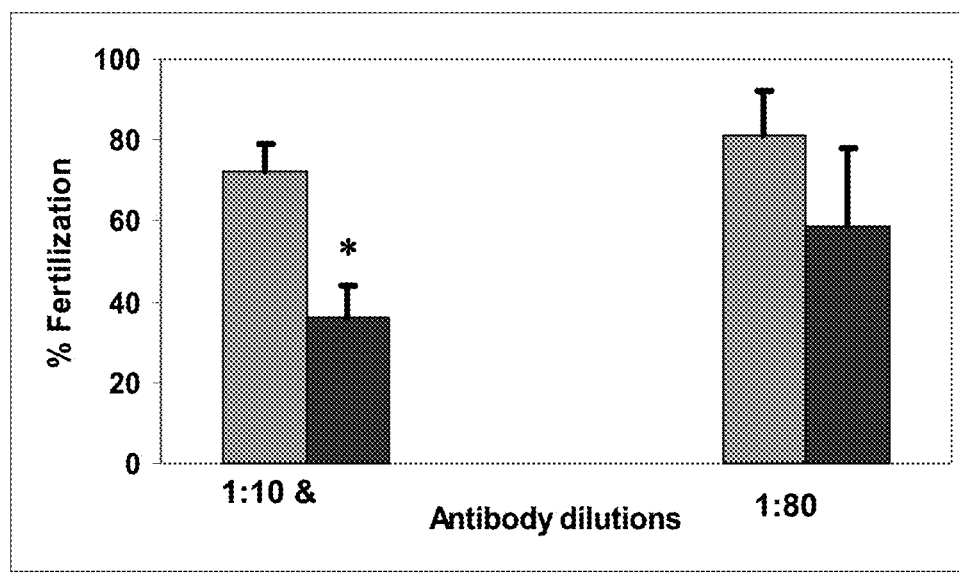
FIG. 16: Effect of SAS1R antibody on mouse in-vitro fertilization. Cumulus intact mouse oocytes were incubated with either preimmune (light shade) or immune (black shade) sera at 1/10 & 1/20 (N=4) or 1/80 (N=2) dilutions for 45 min followed by insemination with capacitated sperm. The number of two cell embryos was scored as fertilized eggs. The statistical significance between the preimmune and immune sera was calculated by t test assuming equal variances; P<0.01.

Antibodies generated to SAS1R in both mice and guinea pigs localized the protein on the microvillar domain in both zona-intact and zona-free live, ovulated oocytes, indicating that the molecule is exposed at the cell surface (see FIGS. 16 and 17). Further, CHO-K1 cells transfected with full length SAS1R (FIG. 4) showed localization to plasma membrane protrusions rather than the planar portions of the cell surface. This observation directly correlates with published reports regarding targeting of membrane proteins to sites of membrane insertion in microvilli of epithelial cells and to plasma membrane protrusions of non-epithelial cells (22). The observation that unpermeabilized CHO-K1 cells did not stain with antibody to C-terminal V5 tag but by anti-SAS1R antibody, whereas permeable cells did stain by both, suggests that the C-terminus of SAS1R is not accessible externally at the cell surface. This result is consistent with the notion that the N-terminus of SAS1R is exposed on the cell surface and mediates interaction with the SLLP1 ligand. Furthermore, the stronger interactive nature of N-terminus of SAS1R with SLLP1 is also evident from both Far-Western and Y2H analyses (FIG. 5).

Role of SAS1R in Sperm Oolemma Binding:

The specific microvillar localization of SAS1R in mature oocytes and co-localization of rSLLP1 to this region (FIG. 7), which is known to be involved in sperm-egg binding and fusion (23), provides correlative physiological support for SAS1R-SLLP1 binding interactions in vivo. An earlier report showed that rSLLP1 reduced fertility and sperm-egg binding at the level of oolemma in a dose dependent manner in mouse IVF studies and retention of SLLP1 in 90% of acrosome reacted sperm (2; see also U.S. patent application Ser. No. 11/915,225, filed Nov. 24, 2008). The present study also revealed a dose dependent inhibition of fertilization when sperm were incubated with rSAS1R (FIG. 8). These data, together with the molecular interactions between SAS1R and SLLP1 evident from surface plasmon resonance, Far-western, Y2H and co-IP studies, suggest SAS1R functions as a receptor for intra-acrosomal SLLP1 at the oolemma.

SAS1R is an Active Protease:

Bioinformatic analysis predicted that SAS1R belongs to a metalloprotease family due to its characteristic zinc binding active site signature. The observation of in vitro proteolytic activity of rSAS1R confirmed this prediction experimentally (FIG. 1, 11). Several other metalloproteases have been reported in the ovary and their role in ovulation and formation and regression of corpus *luteum* has been noted (24). These metalloproteases were localized either in theca interna or externa, interstitial glands, germinal epithelium, in granulosa or theca-interstitial cells and in oocyte cytoplasm (25). By contrast, SAS1R is the first metalloprotease reported to be selectively expressed in oocytes and to be localized on the oolemmal surface. These properties along with the known drugability of metalloproteases suggest this molecule as a candidate contraceptive target. To our knowledge, there are no previous reports of a mammalian oolemmal metalloprotease. Metalloproteases are known to be involved in cellular fusion events. In yeast, cell-cell fusion requires the zinc metalloprotease gene, AXL1 (26). In sea urchin, the zinc chelator (1,10-phenanthroline) showed no effect on binding of acrosome reacted sperm to the oolemma but virtually blocked (95%) subsequent membrane fusion (27). In mouse, inhibitors of the aspartic, cysteine, and serine protease classes had no effect on sperm egg binding or fusion. However, 1,10-phenanthroline, a metalloprotease inhibitor, inhibited mouse sperm-egg fusion without reducing sperm-egg binding, suggesting a critical role of membrane metalloproteases in gamete fusion (28).

SAS1R Conservation in Mammals and Role in Fertilization:

SAS1R has been identified and characterized in the mouse model as an oolemmal receptor for the sperm acrosomal ligand SLLP1. Orthologous and homologous genes with significant homology were identified in other mammals and in lower organisms, respectively. Those in *Drosophila* and *C. elegans* showed about 36% identity while zebrafish showed 42% identity to mouse SAS1R. All these species conserve the signal peptide and the zinc binding metalloprotease domain (FIG. 10). The putative transmembrane domain appears to be conserved in mammals but notably absent in bird, fish, and invertebrates, except *Drosophila*, where it is expressed in the gonad.

In lower organisms, homologous proteins were characterized as hatching enzymes (29). In a previous report an astacin metalloproteinase detected at the RNA level in human and mouse ovaries was tentatively called ovastacin, and, based on evolutionary conservation of function, a similar role in zonal hatching was predicted in mammals (30). The expression of SAS1R begins to decrease after fertilization and is virtually undetectable in blastocysts prior to hatching (FIG. 3) while SAS1R RNA was not detected beyond 1.5 days postcoitum in preimplantation embryos (30). Taken together these results point to a role of this protein in mammalian fertilization, particularly sperm-oolemma interactions, rather than in zonal hatching in mammals, suggesting that the name SAS1R (sperm acrosomal SLLP1 receptor) best conveys its biological interactions.

Fertilization in mammals culminates with fusion of sperm with the oocyte membrane. After acrosome reaction at the zonal surface, the inner acrosomal membrane of the sperm becomes exposed and serves as the limiting membrane on the anterior sperm surface. The intra-acrosomal protein SLLP1 is exposed and retained on the inner acrosomal membrane of acrosome reacted sperm (2). Thus, acrosome reacted sperm that penetrate the zona pellucida will display SLLP1 on their anterior heads and equatorial segments and interact with microvillar SAS1R. The present study advances our understanding of molecular interactions between acrosome-reacted sperm and the mature oocyte at the level of the oolemma.

Example 2—SAS1R as a Target for Contraception

Effect of SAS1R Antibody on Mouse In-Vitro Fertilization.

Antibodies and sera directed SAS1R were prepared. Cumulus intact mouse oocytes were incubated with either preimmune or immune sera at 1/10 & 1/20 (N=4) or 1/80 (N=2) dilutions for 45 min followed by insemination with capacitated sperm. The number of two cell embryos was scored as fertilized eggs. The statistical significance between the preimmune and immune sera was calculated by t test assuming equal variances and are presented in FIG. 16. It can be seen that an inhibitor of SAS1R, such as an antibody directed against SAS1R, is an effective inhibitor of fertilization.

SAS1R is an Effective Immunogen.

Next, it was shown that the SAS1R protein is an effective immunogen in females. As an oocyte specific, sperm oolemmal receptor, SAS1R was hypothesized herein to be a candidate contraceptive vaccinogen and immunogen. Immunogenicity of recombinant mouse SAS1R was tested in female mice which showed serum titers by ELISA against the recombinant target up to a 1/10,000 dilution after the 3rd, 4th & 5th injections (see FIG. 17, left panel). The immunoreactivity of the sera were also studied by immuno-localization in live mouse eggs (see FIG. 17, right panel). The iso-antibodies from female mice stained the microvillar domain of mouse eggs exactly as noted earlier with allo-antibodies raised in guinea pigs (see right panel). This finding confirmed that recombinant mouse SAS1R retained sufficient refolded epitopes to evoke iso-antibodies that cross-reacted with native SAS1R on the microvillar domain.

Figure 18:
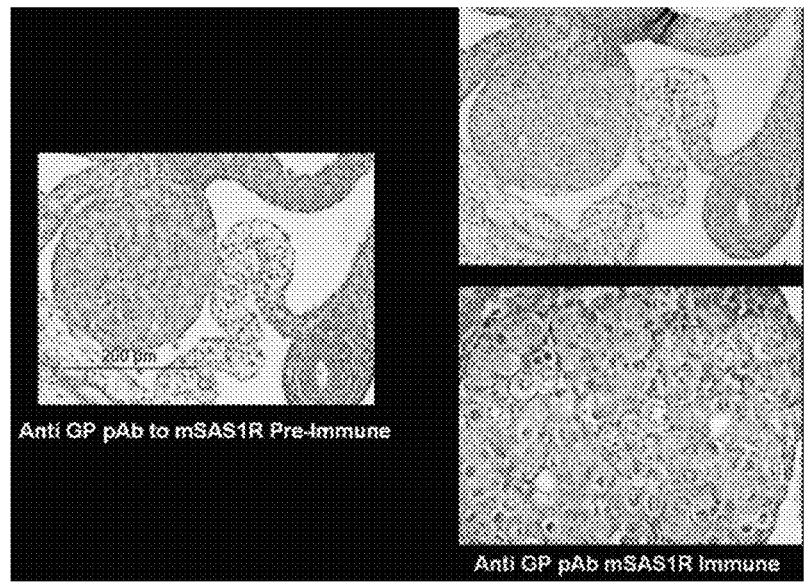
FIG. 18: Day 0—Neonatal mouse ovary on day of birth stained with pre-immune [PI, left panel] or guinea pig anti-SAS1R antibodies [IM, right panel] at identical concentrations [diluted 1:500].

Example 3—SAS1R Localization and Temporal Expression Defines the Opportunity for Reversible Contraception Mouse ovaries were studied from birth until day 56. Sections from day 0 (day of birth) neonatal mouse ovaries were obtained and stained with pre-immune or guinea pig anti-SAS1R antibodies at identical concentrations [diluted 1:500] (FIG. 18). The ovary on this day is comprised principally of naked oocytes or a few forming primary follicles. No immunoreactivity was observed on any ovarian cell type with either sera on day 0, indicating SAS1R protein was not expressed at this stage in the ovary.

Figure 19:
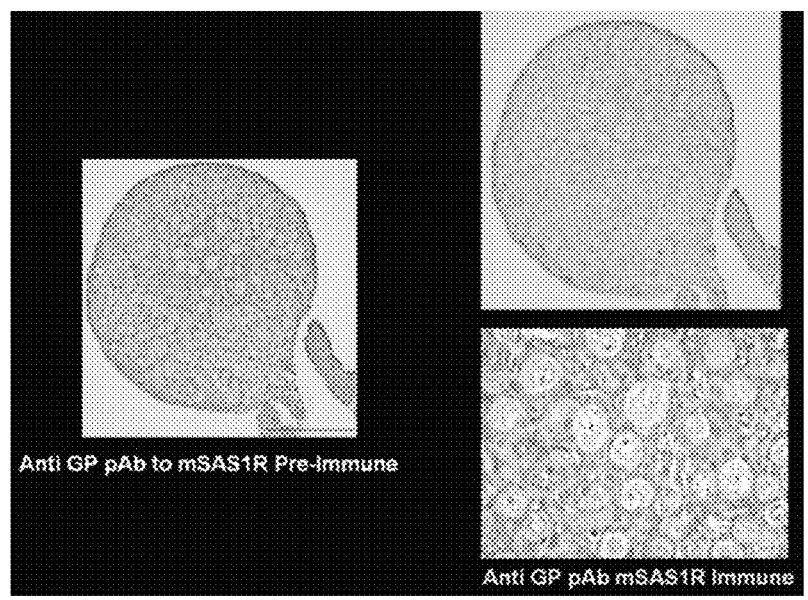
FIG. 19: Day 1.5—Mouse ovary sections 1.5 days after birth stained with pre-immune [PI, left panel] or guinea pig anti-SAS1R antibodies [IM, right panel] at identical concentrations [1:500].

Sections from day 1.5 mouse ovary were stained with pre-immune at identical concentrations [1:500] (FIG. 19). The ovary on day 1.5 is comprised principally of primordial follicles and forming primary follicles in which oocytes are surrounded by a single flat (squamous) layer of granulose cells. No immunoreactivity was observed on any ovarian cell type with either sera, indicating SAS1R was not expressed at this stage in the ovary.

Figure 20:
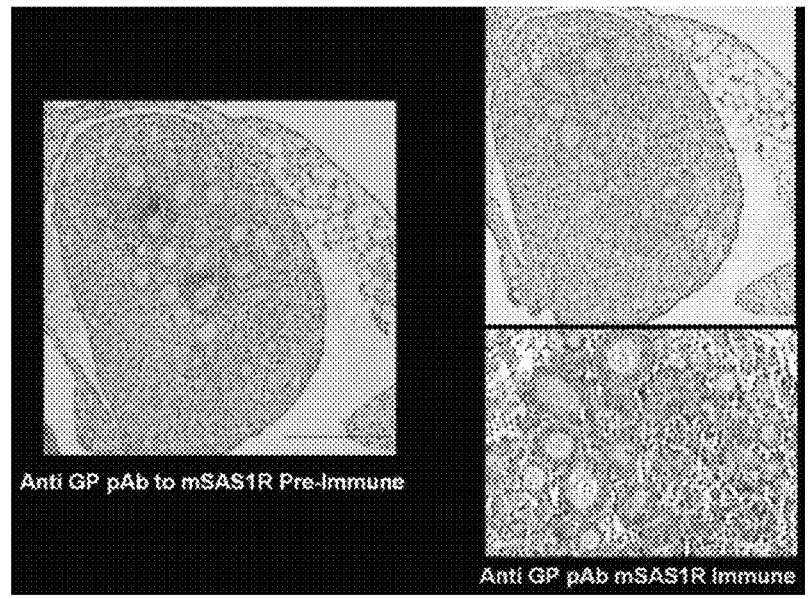
FIG. 20: Day 4—Mouse ovary sections 4 days after birth stained with pre-immune [PI, left panel] or guinea pig anti-SAS1R antibodies [M, right panel] at identical concentrations [1:500].

Sections from day 4 mouse ovary were stained with pre-immune or guinea pig anti-SAS1R antibodies at identical concentrations [1:500] (FIG. 20). The cortex of the ovary on day 4 is comprised of primordial and primary follicles while the ovarian medulla on this day is comprised principally of forming primary follicles in which oocytes are surrounded by a single flat (squamous) layer of granulosa cells as well as more mature secondary follicles containing oocytes surrounded by two layers of cuboidal granulosa cells. Immunoreactivity, indicating the presence of SAS1R, was observed only in oocytes. Further, and importantly, the only oocytes that stained had reached the secondary follicle stage. Pre-immune sera did not stain any cell type indicating that the immune staining was specific for SAS1R. Conclusion: SAS1R is located only in oocytes and only in oocytes that have reached secondary follicle stage.

Figure 21:
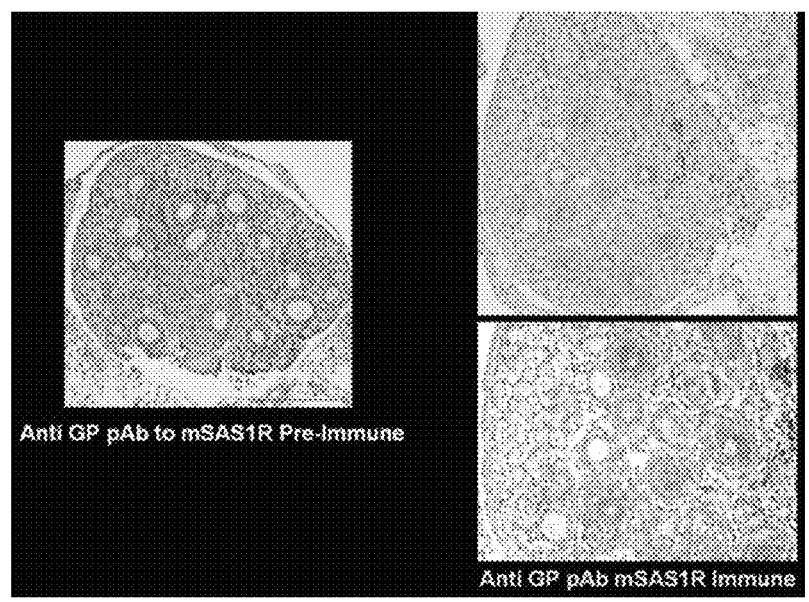
FIG. 21: Day 7—Mouse ovary sections 7 days after birth stained with pre-immune [PI, left panel] or guinea pig anti-SAS1R antibodies [IM, right panel] at identical concentrations [1:500].

Sections from day 7 mouse ovary were stained with pre-immune or guinea pig anti-SAS1R antibodies at identical concentrations [1:500] (FIG. 21). The ovarian medulla on this day is comprised principally of forming primary follicles in which oocytes are surrounded by a single flat (squamous) layer of granulosa cells as well as more mature secondary follicles containing oocytes surrounded by two layers of cuboidal granulosa cells. Immunoreactivity, indicating the presence of SAS1R, was observed only in oocytes. The only oocytes that stained had reached the secondary follicle stage. Pre-immune sera did not stain any cell type indicating that the immune staining was specific. Conclusion: SAS1R is located only in oocytes and only in oocytes that have developed to secondary follicle stages.

Figure 22:
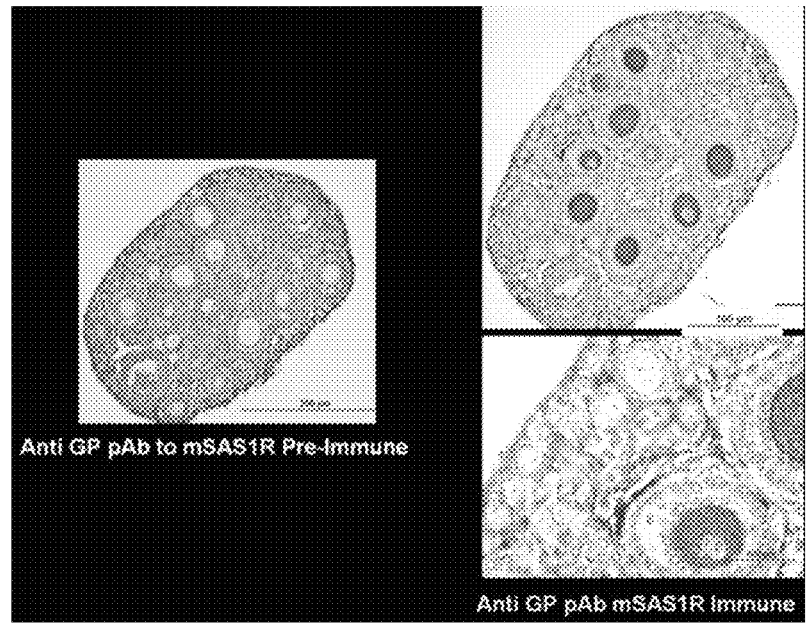
FIG. 22: Day 14—Mouse ovary sections 14 days after birth [pre-pubertal] stained with pre-immune [PI, left panel] or guinea pig anti-SAS1R antibodies [IM, right panel] at identical concentrations [1:500].

Day 14 mouse ovary sections (14 days after birth) were stained with pre-immune or guinea pig anti-SAS1R antibodies at identical concentrations [1:500] (FIG. 22). The ovarian medulla on this day is comprised principally of forming primary follicles in which oocytes are surrounded by a single flat (squamous) layer of granulosa cells as well as more mature secondary follicles containing oocytes surrounded by two layers of cuboidal granulosa cells. A few follicles show signs of being pre-antral. Immunoreactivity, indicating the presence of SAS1R, was observed only in oocytes. The oocytes that stained had all reached the secondary follicle stage or progressed to the pre-antral stage. Pre-immune sera did not stain any cell type indicating that the immune staining was specific. The data demonstrate that SAS1R is located only in oocytes and only in oocytes that have developed to secondary follicle or pre-antral stages.

Figure 23:
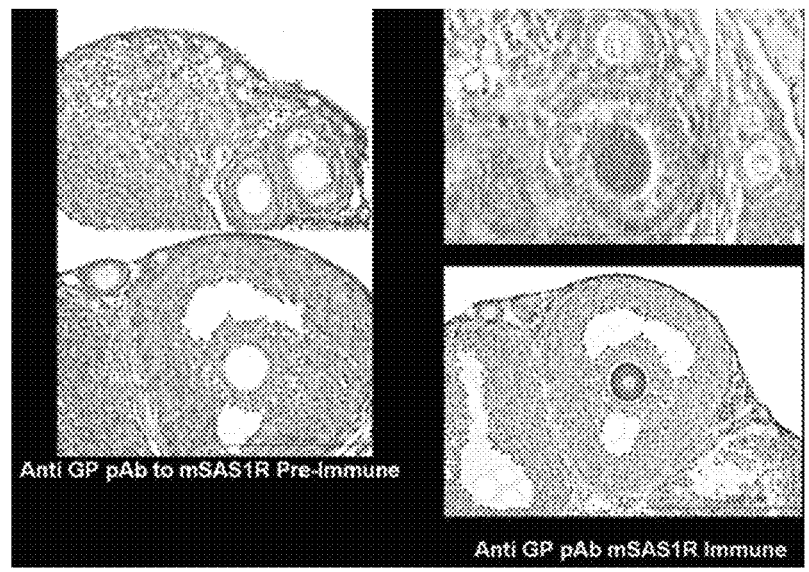
FIG. 23: Day 28—Mouse ovary sections 28 days after birth stained with pre-immune [PI, left panel] or guinea pig anti-SAS1R antibodies [IM, right panel] at identical concentrations [1:500]. Immunoreactivity, indicating the presence of SAS1R, was observed only in oocytes.
Figure 25:
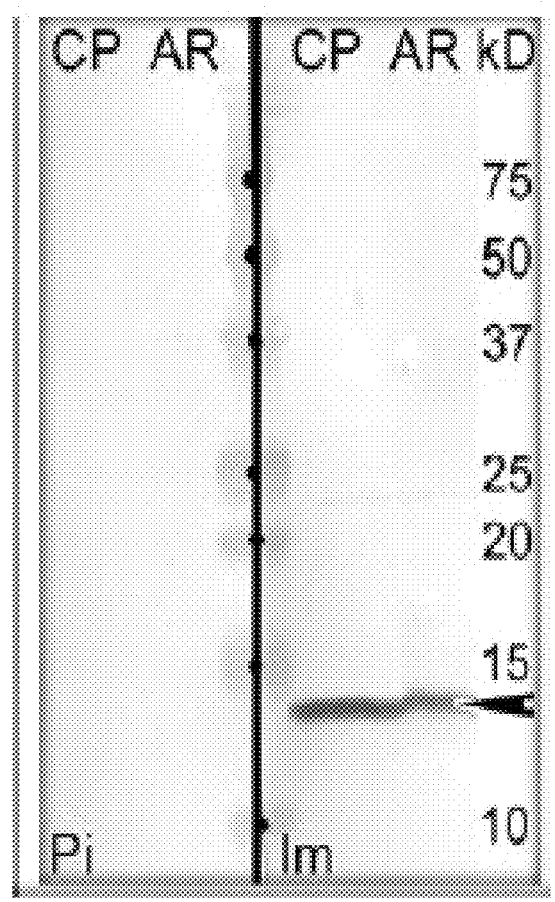
FIG. 25: The insert shows Western analysis of the capacitated (CP) and acrosome reacted (AR) mouse cauda epididymal sperm probed with preimmune (Pi) and immune (Im) serum. The acrosome reacted sperm clearly demonstrated the retention of some mSLLP1, a ~14 kD band (arrow head) in the acrosome reacted population.

Day 28 mouse ovary sections were stained with pre-immune or guinea pig anti-SAS1R antibodies at identical concentrations [1:500] (FIG. 23). The ovarian cortex on this day is comprised of forming primary follicles in which oocytes are surrounded by a single flat (squamous) layer of granulosa cells, more mature secondary follicles containing oocytes surrounded by two layers of cuboidal granulosa cells, and antral follicles with many layers of granulosa cells and fluid filled antral spaces. Immunoreactivity, indicating the presence of SAS1R, was observed only in oocytes. Oocytes that stained were those that had reached the secondary follicle stage of maturation as well as antral [Graafian follicle] stages. Pre-immune sera did not stain any cell type indicating that the immune staining was specific. Conclusion: In the ovaries of mice at puberty, SAS1R is located only in oocytes and only in oocytes that have developed to secondary follicle stage as well as subsequent stages.

Figure 24:
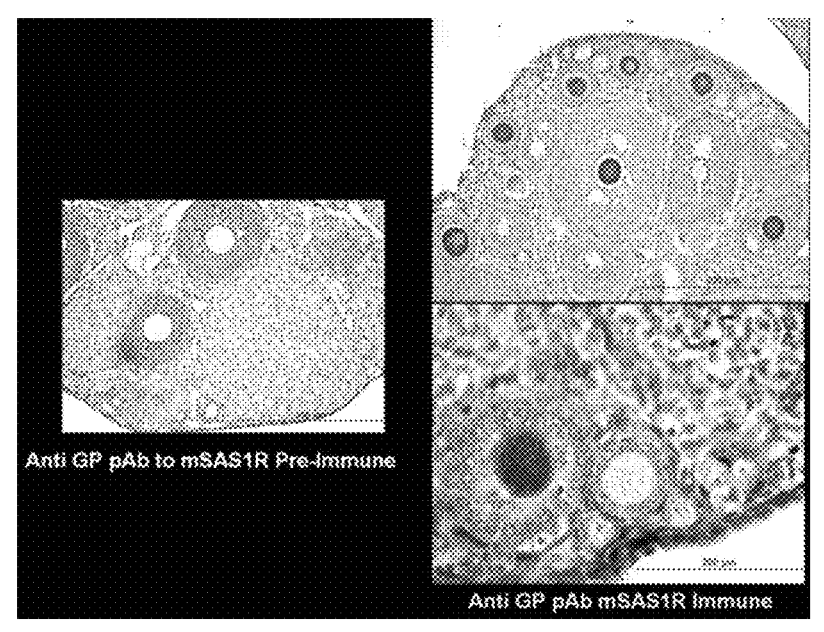

Day 56 adult mouse ovary sections were stained with pre-immune or guinea pig anti-SAS1R antibodies at identical concentrations [1:500] (FIG. 24). The ovarian cortex on this day is comprised of primordial follicles, primary follicles in which oocytes are surrounded by a single flat (squamous) layer of granulosa cells, more mature secondary follicles containing oocytes surrounded by two layers of cuboidal granulosa cells, and many multi-lamellar follicles including antral follicles with many layers of granulosa cells and fluid filled antral spaces. Immunoreactivity, indicating the presence of SAS1R, was observed only in oocytes. Oocytes that stained were those in secondary follicles as well as all intermediate sized oocytes as well as antral [Graafian follicle] stages. Pre-immune sera did not stain any cell type indicating that the immune staining was specific. Particularly noteworthy is the absence of staining in corpora *lutea*. Conclusion: In the ovaries of adult mice, SAS1R is located only in oocytes and only in oocytes that have developed to secondary follicle stage. The SAS1R protein then persists in the oocyte cytoplasm in follicles of all sizes including ovulating follicles.

Summary

Evidence that SAS1R is a Receptor for SLLP1

Native SAS1R showed binding to rSLLP1 by surface plasmon resonance technique.

Bound rec SAS1R captured rec SLLP1 in membrane overlay assay (Far Western analysis).

SAS1R and SLLP1 revealed molecular binding properties by yeast two hybrid analysis.

Immunoprecipitation of rSAS1R recovered rSLLP1 and immunoprecipitated rec SLLP1 recovered rec SAS1R from rabbit reticulocyte extract.

rSLLP1 binds to oocyte microvillar domain and co-localizes with native SAS1R.

rSAS1R binds to acrosome of sperm and co-localizes with native SLLP1.

Native SLLP1 from sperm acrosomal matrix localizes with native SAS1R.

Native SAS1R and native SLLP1 are co-precipitated from mixtures of non-ionic detergent extracts of oocytes and sperm.

Contraceptive Target and Use Implications of Data on SAS1R Ontogeny

SAS1R protein first arises in bilaminar secondary follicles during postnatal oogenesis, in pubertal oogenesis, as well as adult oogenesis. The pattern is uniform irrespective of the age of the animal.

In adult mouse ovaries, SAS1R staining is restricted to oocytes within secondary follicles and all subsequent stages.

Primordial oocytes and primary oocytes do not stain for SAS1R at any developmental stage. No other cell type but oocytes stain for SAS1R, nor is SAS1R found in any other ovarian structure.

SAS1R is localized on live human eggs retrieved for in vitro fertilization.

Administration of exogenous SAS1R elicits an immune response against SAS1R, which localizes to the egg.

Without wishing to be bound by any particular theory, the data disclosed herein suggest that, regarding contraception, oogonia stem cells, including naked oocytes and oocytes within primordial and primary follicles, will not be affected by a drug to SAS1R; the ovarian reserve of stem cells will remain intact.

A contraceptive drug against SAS1R will be reversible.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

Bibliography

1. Mandal A, et al. (2003) SLLP1, a unique, intra-acrosomal, non-bacteriolytic, c lysozyme-like protein of human spermatozoa. Biol Reprod 68, 1525-1537.
2. Herrero M B, et al. (2005) Mouse SLLP1, a sperm lysozyme-like protein involved in sperm-egg binding and fertilization. Dev Biol 284, 126-142.
3. Evans J P, Schultz R M, Kopf G S (1995) Mouse sperm-egg plasma membrane interactions: analysis of roles of egg integrins and the mouse sperm homologue of PH-30 (fertilin) beta. J Cell Sci 108, 3267-3278.
4. Almeida E A, et al. (1995) Mouse egg integrin alpha 6 beta 1 functions as a sperm receptor. Cell 81, 1095-1104.
5. Yuan R, Primakoff P, Myles, D G (1997) A role for the disintegrin domain of cyritestin, a sperm surface protein belonging to the ADAM family, in mouse sperm-egg plasma membrane adhesion and fusion. J Cell Biol 137, 105-112.
6. Evans J P, Schultz R M, Kopf G S (1997) Characterization of the binding of recombinant mouse sperm fertilin alpha subunit to mouse eggs: evidence for function as a cell adhesion molecule in sperm-egg binding. Dev Biol 187, 94-106.
7. Cho C, et al. (1998) Fertilization defects in sperm from mice lacking fertilin beta. Science 281, 1857-1859.
8. Shamsadin R, et al. (1999) Male mice deficient for germ-cell cyritestin are infertile. Biol Reprod 61, 1445-1451.
9. Nishimura H, Cho C, Branciforte D R, Myles D G, Primakoff P (2001) Analysis of loss of adhesive function in sperm lacking cyritestin or fertilin beta. Dev Biol 233, 204-213.
10. Coonrod S A, et al. (1999) Treatment of mouse oocytes with PI-PLC releases 70-kDa (pI 5) and 35- to 45-kDa (pI 5.5) protein clusters from the egg surface and inhibits sperm-oolemma binding and fusion. Dev Biol 207, 334-349.
11. Miyado K, et al. (2000) Requirement of CD9 on the egg plasma membrane for fertilization. Science 287, 321-324.
12. Alfieri J A, et al. (2003) Infertility in female mice with an oocyte-specific knockout of GPI-anchored proteins. J Cell Sci 116, 2149-2155.
13. Kaji K, et al. (2000) The gamete fusion process is defective in eggs of Cd9-deficient mice. Nat Genet 24, 279-282.
14. Le Naour F, Rubinstein E, Jasmin C, Prenant M, Boucheix C (2000) Severely reduced female fertility in CD9-deficient mice. Science 287, 319-321.
15. Rubinstein E, et al. (2006) Reduced fertility of female mice lacking CD81. Dev Biol 290, 351-358.
16. Cohen D J, Ellerman D A, Cuasnicu P S (2000) Mammalian sperm-egg fusion: evidence that epididymal protein D E plays a role in mouse gamete fusion. Biol Reprod 63, 462-468.
17. Da Ros V G, et al. (2008) Impaired sperm fertilizing ability in mice lacking Cysteine-Rlch Secretory Protein 1 (CRISP1). Dev Biol 320, 12-18.
18. Inoue N, et al. (2005) The immunoglobulin superfamily protein Izumo is required for sperm to fuse with eggs. Nature 434, 234-238.
19. Luban J, Goff S P (1995) The yeast two-hybrid system for studying protein-protein interactions. Curr Opin Biotechnol 6, 59-64.
20. Li X, McDermott B, Yuan B, Goff S P (1996) Homomeric interactions between transmembrane proteins of Moloney murine leukemia virus. J Virol 70, 1266-1270.
21. Miyado K, et al. (2008) The fusing ability of sperm is bestowed by CD9-containing vesicles released from eggs in mice. Proc Natl Acad Sci USA 105, 12921-12926.
22. Weigmann A, Corbeil D, Hellwig A, Huttner W B (1997) Prominin, a novel microvilli-specific polytopic membrane protein of the apical surface of epithelial cells, is targeted to plasmalemmal protrusions of non-epithelial cells. Proc Natl Acad Sci US A 94, 12425-12430.

23. Evans J P, et al. (2000) Effects of perturbation of cell polarity on molecular markers of sperm-egg binding sites on mouse eggs. Biol Reprod 62, 76-84.
24. Goldman S, Shalev E (2003) The role of the matrix metalloproteinases in human endometrial and ovarian cycles. Eur J Obstet Gynecol Reprod Biol 111, 109-121.
25. Robinson L L, Sznajder N A, Riley S C, Anderson R A (2001) Matrix metalloproteinases and tissue inhibitors of metalloproteinases in human fetal testis and ovary. Mol Hum Reprod 7, 641-648.
26. Elia L, Marsh L (1998) A role for a protease in morphogenic responses during yeast cell fusion. J Cell Biol 142, 1473-1485.
27. Roe J L, Farach H A, Strittmatter W J, Lennarz W J (1988) Evidence for involvement of metalloendoproteases in a step in sea urchin gamete fusion. J Cell Biol 107, 539-544.
28. Correa L M, Cho C, Myles D G, Primakoff P (2000) A role for a TIMP-3-sensitive, Zn(2+)-dependent metalloprotease in mammalian gamete membrane fusion. Dev Biol 225, 124-134.
29. Hiroi J, et al. (2004) Structure and developmental expression of hatching enzyme genes of the Japanese eel Anguilla *japonica*: an aspect of the evolution of fish hatching enzyme gene. Dev Genes Evol 214, 176-184.
30. Quesada V, Sanchez L M, Alvarez J, Lopez-Otin, C (2004) Identification and characterization of human and mouse ovastacin: a novel metalloproteinase similar to hatching enzymes from arthropods, birds, amphibians, and fish. J Biol Chem 279, 26627-26634.

Example 4

SLLP1 and its Role in Binding to Eggs

Materials and Methods
Cloning and Expression of Mouse SLLP1 (mSLLP1)

Human SLLP1 and SLLP2 nucleic acids and proteins were previously identified and sequenced by the inventors (see U.S. patent application Ser. No. 10/181,611, filed Jul. 18, 2002, the entirety of which is incorporated herein by reference). These proteins were further characterized, and other members of the family were identified by the present inventors (see U.S. patent application Ser. No. 10/542,038 filed Jul. 13, 2005, the entirety of which is incorporated herein by reference; see also Mandal et al., 2003, Biology of Reproduction, 68:1525-1537, the entirety of which is incorporated herein by reference). Both SLLP proteins are sperm specific in their expression.

Using a Blast search tool (Altschul, 1990), a mouse orthologue of the human SLLP1 was sought in the NCBI GenBank database and a candidate gene identified. Single gene-specific forward and reverse primers with NcoI and XhoI restriction sites respectively were designed to amplify the predicted processed form (128 amino acids, from 94 to 221) of the mouse SLLP1. Primers were obtained from Invitrogen (Carlsbad, Calif.). The cDNA was amplified by PCR from a mouse testis cDNA library (Clontech, Palo Alto, Calif.). The cycling parameters employed were 94° C., 2 min; 94° C., 30 sec; 51° C., 1 min; and 68° C., 1.5 min, for 40 cycles. PCR reaction products were separated on agarose gels, and a band of ~400 bp was isolated, reamplified, and subcloned in pCR2.1 TOPO vector (Invitrogen). Multiple cDNA clones were sequenced in both directions using vector-derived primers on a Perkin-Elmer Applied Biosystems DNA sequencer (Biomolecular Research Facility, Univ. of Virginia Health System, VA). The cloned cDNA sequence for mouse SLLP1 was submitted to the GenBank (accession number, AY601763). The insert was then restriction digested, gel purified, ligated into the predigested pET28b+ vector and used to transform competent BL21DE3 cells (Novagen, Madison, Wis.). The final construct added two amino acids at the N-terminus and eight residues at the C-terminus including a six histidine tag. A 7.0 ml culture from a single colony was grown to optical density of ~0.8 at 600$_{nm}$ at 37° C. in Luria broth (LB) in the presence of 50 µg/ml of kanamycin. Isopropyl-β-D-thiogalactopyranoside (IPTG) (Sigma, St. Louis, Mo.) was then added to a final concentration of 1 mM to induce expression. Following 3 h of induction, the bacteria were collected by centrifugation. The recombinant protein was isolated from the insoluble fraction of *E. coli*, dissolved in 8 M urea in binding buffer (20 mM tris-HCl, pH 7.9, 5 mM imidazole and 0.5 M NaCl) and purified on a His binding Ni$^{2+}$ chelation affinity resin column by a modification of the manufacture's procedures (Novagen). The eluates were then dialyzed overnight against three changes of PBS. The dialyzed protein was stored at −20° C. until used. Protein concentrations were determined by Coomassie Plus-200 (Pierce, Rockford, Ill.) using bovine serum albumin (BSA) as a standard.

Polyclonal Antibody Production and Western Blot Analysis

Five adult virgin female guinea pigs were used for antibody production against the purified recmSLLP1. Preimmune serum was collected by heart puncture, and subsequently, each animal was injected with 200 µg of the purified recmSLLP1 in complete Freund's adjuvant and boosted twice at intervals of 14 days with the same amount of protein in incomplete Freund's adjuvant. For all immunizations, half of the antigen emulsion was injected intramuscularly in the legs and half subcutaneously in two sites on the back. All animals were exsanguinated by heart puncture 9 days after the final immunization. Blood was collected in serum separation tubes (Becton Dickinson, Franklin Lakes, N.J.). After centrifugation at 1750 g for 10 min, the serum was removed, aliquoted, and frozen until needed.

Specificity of the antisera was tested against recmSLLP1 and mouse sperm extracts following 1D SDS-PAGE western blotting. RecmSLLP1 (0.1 µg/lane) or cauda epididymal mouse spermatozoa (10 µg/lane) were solubilized in Laemmli buffer (2×) and proteins were resolved on a 15% SDS-PAGE gel and separated at 20 mA. Proteins were then blotted to nitrocellulose and stained by Ponceau. All blots were blocked with 5% nonfat dry milk in PBS with 0.05% Tween 20 (PBS-T) for 30 min at room temperature. For immunoblotting of purified recmSLLP1, 1:15,000 or 1:30,000 dilution of the anti-recmSLLP1 guinea pig sera was tested, whereas for mouse sperm proteins, 1:5,000 or 1:10,000 dilutions of the sera was used. The blots were then washed three times for 10 min in PBS-T, and incubated with 1:5000 dilution of peroxidase conjugated goat anti-guinea pig IgG secondary antibody for 1 h and washed two times for 10 min in PBS-T. The blots were then developed either in TMB peroxidase substrate (3,3',5,5'-tetramethylbenzidine, KPL, Gaithersburg, Md.) or with ECL reagent (Amersham Corp., Buckinghamshire, UK).

Culture Media and Reagents for In Vitro Fertilization Assays

The medium used for in vitro fertilization assays was Fraser's modification of Whittingham's medium (Fraser and Drury, 1975) supplemented with 3% BSA and prepared with culture grade H$_2$O with analytical-grade reagents. TYH (Toyoda, 1971) medium was used for sperm-oolemma binding assays. Pregnant mare's serum gonadotrophin (PMSG), human chorionic gonadotrophin (hCG), BSA, culture grade $H_2O$, hyaluronidase, chymotrypsin, Hoechst dye 33342 and other reagents were obtained from Sigma.

Gamete Preparation for In Vitro Assays

Hybrid F1 mice (C57BL/6J×CBA) were used in all experiments. Suspensions of epididymal spermatozoa from sexually mature male mice were prepared for insemination of isolated oocytes. Oocytes were obtained from 28-day-old females superovulated with 10 IU PMSG and 10 IU hCG, injected intraperitoneally 48 h apart. Females were killed 16 h after hCG injection and both oviducts were immediately removed and placed in mineral oil.

In Vitro Fertilization with Cumulus-Oocyte Complexes

In vitro fertilization with cumulus intact oocytes was conducted with sperm dispersed from cauda epididymides placed for 5 min in 200 µl drops of fertilization medium under paraffin oil. The sperm suspension was diluted to a concentration of $10^6$ sperm/ml in a volume of 200 µl and then incubated for 120 min in a humidified tissue culture incubator (37° C., 5% $CO_2$ in air) to allow capacitation. In the experiments where anti-recmSLLP1 serum was tested, spermatozoa were incubated with varying concentrations of decomplemented (56° C., 30 min) immune or preimmune serum for the last 45 min of capacitation. In the experiments where recmSLLP1 was evaluated, spermatozoa were incubated under standard capacitating conditions.

Cumulus masses were placed in 135 µl drops of fertilization medium (one mass per drop) under paraffin oil and were incubated for 45 min with immune or preimmune serum or in presence or absence of recmSLLP1 prior to insemination. Fifteen µl of the sperm suspension (final concentration: $10^5$ sperm/ml) was then added to each cumulus mass drop. Thus, sera or recombinant protein was present in the incubation droplet during gamete interaction. Six hours following insemination oocytes were relocated in 100 µl drops of fertilization medium under mineral oil. Following overnight incubation, eggs were stained in Hoechst dye (10 µg/ml) for 10 min and washed 3 times in fertilization medium. The eggs were then placed in a 5 µl drop of fertilization medium between a microscope slide and an elevated coverslip, and visualized at 160× using light and fluorescence microscopy (Zeiss Axioplan). Two cells embryos were scored as fertilized, while one-celled oocytes were scored as unfertilized.

In Vitro Fertilization with Zona-Free Eggs

For the sperm-oolemma binding assay, two cauda epididymides were placed in 900 µl drops of fertilization medium under paraffin oil for the dense mass of spermatozoa to flow freely for ~15 min and then diluted at $1×10^6$/ml for 3 h of capacitation. Cumulus oocyte complexes were placed in 200 µl drops of TYH medium under paraffin oil. Cumulus cells were removed by treating the oocytes for 3 min with 1 mg/ml hyaluronidase in TYH medium and then washed 8 times in 50 µl drops. Zona pellucidae were loosened by treating the oocytes with 10 µg/ml chymotrypsin in TYH media for 1 min and loosened zonae were removed by mechanical agitation using a pulled Pasteur pipette. The oocytes were then washed 10 times and allowed to recover from chymotrypsin treatment by incubating in TYH media for 3 h, following which, they were stained with 10 µg/ml Hoechst dye for 10 min, and then gently washed.

To test the effects of anti-recmSLLP1 antibodies, spermatozoa were incubated with varying concentrations of decomplemented immune or preimmune sera for the last 30 min of capacitation. Untreated oocytes were then added to the incubation drops containing the treated sperm with the final concentration being $2.5×10^4$ sperm/ml.

To compare the effects of recmSLLP1 with human and chicken c lysozymes, spermatozoa were first incubated under standard capacitating conditions. Oocytes were preincubated for 45 min before insemination with recmSLLP1 (0.1 to 200 µg/ml) or with hSLLP1 (25 µg/ml) or with chicken or human lysozyme (50 µg/ml, 100 µg/ml). Untreated capacitated sperm were then added to the incubation drops containing the treated eggs with a final sperm concentration of $2.5×10^4$/ml. Thus, in all the experiments performed the sera, the recombinant protein, or the lysozyme was present in the incubation droplet during gamete interaction. After 30 min of gamete co-incubation, oocytes were gently washed 5 times in TYH medium and placed between a microscope slide and an elevated coverslip and visualized at 160×. Binding to the oocyte was scored by counting the number of bound spermatozoa per oocyte using phase contrast. Fusion with the egg was scored by counting the number of decondensed sperm heads within each oocyte using fluorescence microscopy.

Indirect Immunofluorescence Studies of Mouse Spermatozoa and Oocytes Localization of mSLLP1 on Fixed Spermatozoa Cauda epididymal mouse spermatozoa were placed in 0.9 ml drop of phosphate-buffered saline without calcium (PBS; pH 7.4) (two epididymides per drop) and incubated at 37° C. in an atmosphere of 5% $CO_2$ for 5 min. To induce the acrosome reaction, spermatozoa were incubated in TYH media for 90 min to undergo capacitation (Visconti et al, 1995) and 5 µM calcium ionophore A23187 was added for another 15 min for the acrosome reaction to occur. Each drop was then collected, centrifuged for 10 min at 500 g and resuspended in PBS; this washing procedure was repeated three times. Smears of the final suspension of mouse sperm in PBS were air-dried on microscope slides at room temperature and fixed in 2% w/v paraformaldehyde in PBS for 10 min. After 6 washes in PBS, spermatozoa were incubated for 30 min at 37° C. with normal goat serum (NGS) (5% v/v in PBS) and then incubated for 1 h with anti-recmSLLP1 sera (1:25). The slides were washed 3 times in PBS and spermatozoa were incubated for 1 hour at 37° C. with Texas red-conjugated polyclonal antibody from donkey (1:200, Jackson Laboratories). Slides were then washed, incubated for 30 min at room temperature with Peanut agglutinin lectin (PNA) (1:50) (Molecular Probes) conjugated with FITC, washed, mounted in Slowfade® (Molecular Probes, Eugene, Oreg.), and visualized under a Zeiss Standard 18 ultraviolet microscope. Images were captured by using MrGrab (Carl Zeiss Vision GmbH, Germany).

Egg Labeling:

Metaphase II eggs were obtained as previously described (Coonrod et al, 1999) and incubated with 5% NGS/media for 30 min. Oocytes were washed five times in TYH medium and incubated with 100 µg/ml recmSLLP1 or 100 µg/ml lysozymes for 45 min at 37° C. and 5% $CO_2$. Oocytes were washed five times and incubated with guinea pig anti-recmSLLP1 polyclonal antibody (1:50), sheep anti-human lysozyme (1:25) or rabbit anti-chicken lysozyme (1:400) in 5% NGS/media for 1 h at 37° C. and 5% $CO_2$. Oocytes were washed five times and incubated with donkey anti-guinea pig/Texas Red antibody (1:200) or goat anti-guinea pig/FITC antisera 1:200), donkey anti-sheep and goat anti-rabbit FITC-labeled secondary antibody (1:200) (Jackson ImmunoResearch), respectively in 5% NGS/media for 1 h at room temperature at 37° C. and 5% $CO_2$. Oocytes were washed and mounted in media onto glass slides and visualized under a Zeiss Standard 18 ultraviolet microscope. Images were captured by using MrGrab 1.0 (Carl Zeiss Vision GmbH, Germany).

Scanning Confocal Microscopy

Metaphase II eggs employed for immunofluorescence studies (above) were utilized for scanning confocal microscopy. The stained eggs were washed three times in PBS containing 1% BSA (PBS/BSA) and then fixed in 4% paraformaldehyde in PBS-polyvinylalcohol (PVA) for 20 min at room temperature. Following fixation, eggs were washed 5 times in PBS/BSA and then permeabilized with 0.5% Triton X-100 in PBS for 20 min at room temperature. Eggs were then washed five times in PBS/BSA and placed in 0.4 mg/ml RNase in PBS/BSA for 30 min and then stained with 20 nM Sytox (Molecular Probes) for 10 min. Eggs were then extensively washed, placed in slow fade (Molecular Probes) equilibration media for approximately 1 min and then mounted on slides in slow fade mounting media. Images were obtained on a Zeiss 410 Axiovert 100 microsystems LSM confocal microscope. For each panel, attenuation, contrast, brightness and pinhole aperture remained constant. For each panel, four seconds scans were averaged four times per line using a 63× oil lens equipped with a zoom factor of two.

Sperm Labeling During Binding to Metaphase II Eggs

Zona-free eggs inseminated with capacitated spermatozoa from the in vitro fertilization studies above were fixed with 2% paraformaldehyde for 10 min at room temperature. Gametes were washed in PBS-BSA, incubated with 5% NGS/PBS-BSA for 30 min at 37° C. and then incubated for 1 h with anti-recmSLLP1 sera (1:25). The slides were washed 3 times in PBS and gametes were incubated for 1 h at 37° C. with donkey anti-guinea pig Texas red-conjugated polyclonal antibody (1:200, Jackson Laboratories). Gametes were then washed five times in PBS/BSA, placed in 0.4 mg/ml RNase in PBS/BSA for 30 min, and then stained with 20 nM Sytox (Molecular Probes) for 10 min for nuclear staining. Gametes were extensively washed, placed in slow fade (Molecular Probes) equilibration media for approximately 1 min and then mounted on slides in slow fade mounting media. Images were obtained on a Zeiss 410 Axiovert 100 microsystems LSM confocal microscope as described above.

Statistical Analysis

All in vitro assays were repeated at least three or more times. Experimental and control group values were reported as means±standard error of mean. Groups were compared using the matched-pairs t-test assuming equal variances and differences were reported at $P<0.05$ as the level of significance (Bowers, D. Medical Statistics from Scratch. John Wiley & Sons; West Sussex, U K, 2002, pp. 129-132).

Results

Mouse SLLP1 is the True Orthologue of hSLLP1 and Shares Similar Characteristics to c Lysozymes The complete amino acid sequence of mSLLP1 was deduced (predicted mol. wt. 25 kDa, pI—6.2). The N terminus of mSLLP1 contains a predicted transmembrane domain followed immediately by a potential protease cleavage site between alanine 93 and lysine 94 linkage. Comparison of the full-length hSLLP1 and mSLLP1 sequences using the Accelrys Gap (Seq/Web version 2) algorithm found that mSLLP1 is 64.2% similar and 58.8% identical to the hSLLP1. The mSLLP1 processed form, starting after the protease cleavage site (128 amino acids), shares 82.8% similarity and 75.8% identity to that of hSLLP1. The deduced mSLLP1 sequence contains three putative myristoylation sites (G2, G41 and G142), potential phosphorylation sites for casein kinase II (S97) and protein kinase C (S66, S90, S152, and S153) and a signature sequence for the alpha-lactalbumin/lysozyme C family. The predicted molecular weight (14.6 kDa) and pI (5.2) of mature mSLLP1 are identical to hSLLP1.

In addition, a Blast search of the NCBI GenBank database and a multiple sequence alignment of selected mature c lysozymes revealed that mature mSLLP1 is 46%, 48% and 50% identical to mouse, human and chicken lysozymes, respectively. Forty-one residues in mSLLP1 are identical to the three conventional lysozymes. Among the 20 invariant residues of c lysozymes (Prager, E. M., and Jolles, P., Animal lysozymes c and g: an overview. In: Jolles, P. (Ed.), Lysozymes: Model Enzymes in Biochemistry and Biology. Birkhauser Verlag, Basel, 1996, pp. 9-31), 16 were found to be conserved in mSLLP1. Interestingly, the essential catalytic residues (E35 and D52) of chicken lysozyme were replaced with T35 and N52 in mSLLP1 as well as hSLLP1 (Prager, E. M., and Jolles, P., Animal lysozymes c and g: an overview. In: Jolles, P. (Ed.), Lysozymes: Model Enzymes in Biochemistry and Biology. Birkhauser Verlag, Basel, 1996, pp. 9-31). Among the six potential substrate-binding residues of c lysozymes, five were conserved in both mSLLP1 and hSLLP1 (Kumagai, I., Sunada, F., Takeda, S., and Miura, K., 1992. Redesign of the substrate-binding site of hen egg white lysozyme based on the molecular evolution of C-type lysozymes. J. Biol. Chem. 267, 4608-4612).

The mouse SLLP1 gene, Spaca3, is a six exon gene located on chromosome 11 at locus B5 where it is flanked by the gene for amiloride-sensitive cation channel 1, Accn1, and an unknown protein belonging to the myosin family. This locus in the mouse is considered syntenic with 17q12 where the human SLLP1 gene, SPACA3, is also flanked by ACCN1 and the myosin gene MYO1D. Furthermore, the intron positions of mature mouse and human SLLP1 precisely match with that for human and mouse lysozymes interrupting codons for Trp, Asp/Ala and Trp, suggesting a possible origin of these genes from a common ancestor.

Expression of mSLLP1 and Specificity of the Antibody

A cDNA sequence encoding the mature mSLLP1 from residue 94 to 221 (beginning after the putative protease cleavage site), and including a six-histidine C terminal tag was expressed in E. coli and a recombinant protein of about 15 kDa was obtained after $Ni^{++}$-affinity purification. To evaluate the relative purity of the recmSLLP1 preparation, an aliquot of the purified protein was separated by 1-D electrophoresis and the gel was silver stained and blotted to probe with anti-his antibody. A prominent band of about 15 kDa and a much fainter putative dimer at about 30 kDa were noted. These results indicated that the recmSLLP1 preparation used for this study was highly purified.

The specificity of the antibody generated in guinea pigs against recmSLLP1 was examined by western blotting against both the recombinant immunogen and mouse sperm proteins. The immune sera recognized the 15 kDa recombinant SLLP1 as well as the putative 30 kDa dimer found in the recombinant preparation, while the preimmune serum as well as the serum from guinea pigs injected with adjuvant alone showed no immunoreactivity with recSLLP1. In mouse sperm extracts the immune serum reacted only with a about 15 kDa band while the serum from guinea pigs injected with adjuvant alone as well as preimmune sera showed no reactivity. These results indicated that a specific immunoreagent had been generated to the recmSLLP1 that gave a single band on sperm protein extracts. Finding only a ~15 kDa form of mSLLP1 in sperm protein extracts demonstrated that full length mSLLP1, predicted to run at ~25 kDa, was not detectable in sperm. Further mSLLP1 dimerization does not occur in sperm although a small amount does occur during E. coli expression. The observations also indicated that E. coli expressed mSLLP1 after affinity purification contained sufficient numbers of immunogenic epitopes to generate antibodies cross reactive with the native mSLLP1.

Mouse SLLP1 is Associated with Sperm Acrosome and Retained after Acrosome Reaction Indirect immunofluorescence of fixed mouse spermatozoa localized mSLLP1 to the anterior acrosome in 70.0% of non-capacitated caudal spermatozoa (Table 1). However, 20.3% of non-capacitated spermatozoa showed an equatorial segment distribution of mSLLP1 and 4.5% possessed no staining (Table 1). Seventy-one percent of acrosome-reacted sperm, determined by the lack of fluorescence in the acrosome by PNA lectin staining, displayed only equatorial segment reactivity with anti-recmSLLP1 serum. However, 13.9% of acrosome-reacted spermatozoa retained an anterior acrosome staining pattern while 9.3% did not stain (Table 1). The disappearance of mSLLP1 staining in the anterior acrosome appeared to correspond with the appearance of staining in the equatorial segment following capacitation and the acrosome reaction.

Proteins from acrosome reacted sperm were analyzed by Western analysis (Table 1 insert) using anti-recmSLLP1 serum. Ionophore treated, acrosome reacted sperm showed a ~14 kD mSLLP1 band with very subtle decrease in migration compared to proteins extracted from capacitated sperm. The slower migration of the ~14 kD band is possibly due to changes in phosphorylation/dephosphorylation of mSLLP1 during the acrosome reaction, a process known to be regulated by protein phosphorylation (Furuya et al, 1992). The presence of mSLLP1 in ionophore treated as well as capacitated sperm confirmed that the observed equatorial immunofluorescent staining is a specific SLLP1 pattern. Importantly, confocal analysis showed retention of mSLLP1 in all capacitated mouse sperm tightly bound to mouse eggs, emphasizing the concept that this protein may be involved in sperm-oolemma binding.

RecmSLLP1 and Anti-recmSLLP1 Serum Inhibit Fertilization of Mouse Cumulus Intact Eggs To determine the role of mSLLP1 during fertilization, both spermatozoa and cumulus intact oocytes were pre-incubated with anti-recmSLLP1 serum or preimmune serum for 45 min prior to insemination. Fertilization was conducted in the presence of the antibody and six hours later the eggs were relocated in 100 µl drops of fertilization medium and incubated overnight. In the groups treated with the immune sera at 1:10 or 1:50 dilutions, the percentage of two cells embryos was significantly ($P \leq 0.05$) reduced (61% and 17% inhibition respectively; Table 2A) from the values observed with respective preimmune serum. However, a significant effect on cumulus intact eggs was not observed at a 1:100 dilution.

Cumulus intact oocytes were also incubated with two concentrations of recmSLLP1, which remained in the culture medium during the fertilization process. Treatment of the cumulus-oocyte complexes with 200 µg/ml recmSLLP1 significantly reduced the fertilization rate from 45% in the control group to 12% in the recmSLLP1 treated group (73% inhibition, $P \leq 0.05$), whereas no significant difference was observed on the percentage of fertilization between the control group and the group treated with 50 µg/ml recombinant protein, although a reduction was noted (Table 2B). Taken together, these results suggested that mSLLP1 plays a role in fertilization.

Mouse SLLP1 has a Role in Sperm-Egg Binding

Inhibition of fertilization by recmSLLP1 protein as well as antibodies to recmSLLP1 using cumulus-egg complexes prompted a dose-ranging study of the effect of antibody to SLLP1 and recmSLLP1 on gamete binding and fusion to determine the stage in the fertilization cascade at which mSLLP1 exerted its effects. Therefore, we tested whether anti-recmSLLP1 serum and recmSLLP1 protein would block capacitated mouse sperm-egg binding, fusion, or both to zona-free mouse eggs. Statistically significant inhibition of binding but not fusion was observed when both gametes were co-incubated in the presence of 1:10 and 1:50 dilutions of anti-recmSLLP1 immune sera compared to preimmune sera, whereas the 1:100 dilutions were not significantly different.

The most striking effect was observed when zona-free mouse eggs were incubated with different concentrations of recmSLLP1 (0.1-200 µg/ml) and then inseminated with untreated capacitated mouse spermatozoa. The incubation of oocytes with recmSLLP1 produced a concentration-dependent decrease in the number of spermatozoa bound to or fused to the egg, with a significant effect observed at as low as 0.1 µg/ml and 100% inhibition of both binding and fusion at 200 µg/ml (12.5 µM). Zona-free mouse oocytes incubated in the absence of recmSLLP1 (buffer only) was used as control. Importantly, no difference was observed in the percentages of motile spermatozoa compared to the control suggesting that anti-recmSLLP1 or recmSLLP1 protein did not affect sperm motility but oolemma binding and subsequent fusion. Taken together, these results support the participation of mSLLP1 in the binding event at the mouse egg surface prior to fertilization.

Mouse SLLP1 has Complementary Binding Sites on Unfertilized and Fertilized Oocytes To study the possible localization of mSLLP1-binding sites on the egg surface, unfertilized oocytes along with in vitro fertilized oocytes at the pronuclear stage, were incubated with purified recombinant mSLLP1 for 45 min, washed, and then exposed to anti-recmSLLP1. Unfertilized oocytes exhibited fluorescent labeling within the perivitelline space and over much of the oocyte surface. However, an area devoid of fluorescence was consistently detected. Hoechst staining revealed that this negative area was always associated with the area of the oocyte plasma membrane overlying the metaphase plate. Thus, mSLLP1-binding sites were restricted to the fusogenic region of the egg, consistent with a role for mSLLP1 interaction in sperm-egg binding. Interestingly, oocytes, with or without zona pellucida, that had been fertilized in vitro and treated with recmSLLP1, exhibited intense, patchy immunofluorescent domains over the entire egg surface, indicating that SLLP1 binding sites remain associated with egg surface domains after fertilization. Controls included oocytes not exposed to recmSLLP1 and then exposed to anti-recmSLLP1, oocytes incubated with recmSLLP1 and then exposed to preimmune sera, and oocytes incubated with recePAD (an egg cytoplasmic protein; Wright et al., 2003, ePAD, an oocyte and early embryo-abundant peptidylarginine deiminase-like protein that localizes to egg cytoplasmic sheets. Dev. Biol. 256, 73-88) and then incubated with the respective specific antibody. None of these three controls showed egg surface fluorescence.

Confocal analyses were then employed to refine the localization of mSLLP1 binding sites in the egg after treatment with recombinant SLLP1. Optical sections of zona intact unfertilized oocytes showed that mSLLP1-binding sites were localized predominantly to the perivitelline space.

In contrast, fluorescence was virtually undetected in the perivitelline space of fertilized eggs while an intense signal for SLLP1 was evident on the oolemma in distinct patches. A weak fluorescent labeling was also observed on zona pellucidae of both unfertilized and fertilized eggs.

C Lysozymes do not Block Gamete Binding or Fusion to the Mouse Egg

Mouse and human SLLP1 are lysozyme-like proteins that share several characteristics of the c lysozyme family. Mouse SLLP1 is 48% identical to human and 50% identical to chicken lysozyme, 46% identical to conventional mouse lysozyme, while human SLLP1 is 52% identical to human lysozyme and 48% identical to chicken lysozyme. To determine whether conventional c lysozymes have an inhibitory effect similar to SLLP1 on sperm-egg binding and fusion, human and chicken lysozyme were incubated with mouse oocytes at concentrations shown previously to exert maximal effects for SLLP1s. Although 50 μg of mouse SLLP1 and 25 μg of human SLLP1 maximally inhibited sperm-egg binding and fusion, a similar effect was not observed even at 50 or 100 μg/ml of the conventional c lysozymes. Similarly, mouse oocytes did not show any fluorescence when incubated with human or chicken c lysozymes and their respective antibodies, indicating a lack of oolemmal receptors for these c lysozymes.

Table 1: Incidence of SLLP1 staining patterns in populations of acrosome intact and acrosome reacted mouse spermatozoa. In acrosome intact sperm, defined by positive PNA staining, mSLLP1 localized mainly to the anterior acrosome (70.0%), secondarily to the equatorial segment (20.3%), whereas 4.5% of the cells displayed no staining. In capacitated and ionophore-induced acrosome reacted sperm this pattern was reversed, mSLLP1 was localized to the anterior acrosome in only 13.9% of spermatozoa, whereas mSLLP1 localized to the equatorial region in 70.9% of the cells. The percentage of acrosome reacted (AR) sperm in the population is addressed in the last column.

TABLE 1

| Group Treatment/PNA staining | Staining in anterior acrosome (%) | Staining in equatorial segment (%) | No staining (%) | # of sperm counted | AR sperm (%) |
|---|---|---|---|---|---|
| Non-capacitated/ acrosome intact PNA(+) | 70.0 | 20.3 | 4.5 | 177 | 5.2 |
| Capacitated/ acrosome reacted PNA(−) | 13.9 | 70.9 | 9.3 | 172 | 94.1 |

Table 2 (comprising Tables 2A and 2B): Effect of SLLP1 anti-serum and recmSLLP1 on mouse in vitro fertilization using cumulus intact oocytes. In all cases, the sera or the recombinant proteins were present during fertilization. Two cells embryos were scored as fertilized after 24 h. (*) P≤0.05. (A) Decomplemented preimmune (PI) or anti-rec-mSLLP1 immune (I) sera were added to both gametes 45 min prior to insemination. Statistically significant inhibition was seen at 1:10 and 1:50 dilutions. (B) RecmSLLP1 was added to the oocytes 45 min prior to insemination with untreated capacitated mouse spermatozoa. Significant inhibition was noted at 200 μg/ml of mSLLP1. Control oocytes were pre-incubated with PBS containing no recmSLLP1.

TABLE 2A

| Treatment | # of experiments | total # of eggs | # of 2 cells embryo | # of non fertilized eggs | % Fertilization |
|---|---|---|---|---|---|
| PI 1:00 | 3 | 20 | 15 | 5 | 75 |
| I 1:100 | 3 | 20 | 14 | 6 | 70 |
| PI 1:50 | 3 | 38 | 27 | 11 | 71 |
| I 1:50 | 3 | 46 | 27 | 19 | 59* |
| PI 1:10 | 6 | 64 | 43 | 21 | 67 |
| I 1:10 | 6 | 80 | 21 | 59 | 26* |

TABLE 2B

| Treatment | # of experiments | total # of eggs | # of 2 cells embryo | # of non fertilized eggs | % Fertilization |
|---|---|---|---|---|---|
| Control | 3 | 20 | 11 | 9 | 55 |
| recmSLLP1 50 μg/ml | 3 | 52 | 25 | 27 | 48 |
| Control | 3 | 29 | 13 | 16 | 45 |
| recmSLLP1 200 μg/ml | 3 | 64 | 8 | 56 | 12* |

Additionally, it can be seen that recombinant mouse SLLP1 can essentially completely inhibit sperm-egg binding, as measured by number of sperm bound/egg, as well as sperm-egg fusion, relative to the controls, including comparison to a recombinant egg protein, ePAD.

Sperm Protein SLLP2: Role in Sperm Binding with Egg and Use to Identify Egg Receptors for Sperm.

Human SLLP1 and SLLP2 nucleic acids and proteins were previously identified and sequenced by the inventors (see U.S. patent application Ser. No. 10/181,611, filed Jul. 18, 2002, the entirety of which is incorporated herein by reference). These proteins were further characterized, and other members of the family were identified by the present inventors (see U.S. patent application Ser. No. 10/542,038 filed Jul. 13, 2005, the entirety of which is incorporated herein by reference). Both SLLP proteins are sperm specific in their expression.

A schematic comparison of human and mouse SLLP1 and 2 is provided. Additionally, the human SLLP2 cDNA and deduced amino acid sequences were determined and are provided. The precursor SLLP2 is about 18 kDA, with a pI of 5.9 and the processed form is 15.7 kDA and the pI is 5.9.

Human SLLP1 and SLLP2 each contain a signal peptide. The initial SLLP1 polypeptide is synthesized as a 215 amino acid polypeptide having a MW of 23.4 kDa and a pI of 8.0. The mature SLLP1 peptide is 128 amino acids and has a MW of about 14.6 kDa and pI of 5.0. The initial SLLP2 polypeptide is synthesized as a 159 amino acid polypeptide having a MW of 17.9 kDa and a pI of 5.9. The mature SLLP2 peptide is 138 amino acids and has a MW of about 15.7 kDa and pI of 5.9.

Human SLLP1 and SLLP2 have 48.8% sequence identity between one another and have 52% and 44% amino-acid sequence identity with the one known mature human lysozyme C, respectively, and 44% and 43% amino-acid sequence identity with the predicted lysozyme homologue on chromosome 17q11.2. SLLP1 is most closely related to human lysozyme (52% sequence identity), whereas SLLP2 is most closely related to chicken lysozyme (51% sequence identity).

The gene encoding SLLP1 is located on Chromosome 17 and is 6012 bp in length. The SLLP1 gene contains 5 exons (109, 309, 159, 79 and 164 bp, respectively) and 4 introns (3436, 1125, 443 and 188 bp, respectively). The gene encoding SLLP2 is located on Chromosome Xp11.1 and is 1950 bp in length. The SLLP2 gene contains 4 exons (169, 159, 79 and 181 bp, respectively) and 3 introns (428, 830, and 104 bp, respectively). Interestingly, exons 3 and 4 of SLLP1 have a sequence identity with exons 2 and 3 of SLLP2 greater than the overall sequence identity between the two complete proteins (i.e. greater than 48.8%) and exons 3 and 4 of SLLP1 are identical in size to exons 2 and 3 of SLLP2, respectively.

```
Mature Mouse SLLP2 cDNA Sequence (SEQ ID NO: 15):
AAGATTTATGAACGCTGTGAGCTGGCAAAGAAGCTGGAGGAGGCTGGCCT

CGATGGCTTCAAAGGCTATACTGTTGGAGACTGGCTGTGTGTGGCACACT

ATGAGAGTGGCTTTGACACCTCTTTTGTGGACCACAATCCAGATGGCAGC

AGTGAATATGGCATTTTCCAGCTGAACTCTGCCTGGTGGTGTAACAATGG

CATCACACCCACTCAGAACCTCTGCAACATCGATTGTAATGACCTGCTCA

ACCGCCATATTCTGGATGATATCATATGTGCCAAGAGGGTTGCATCCTCA

CATAAGAGTATGAAGGCCTGGGATTCCTGGACCCAGCACTGTGCCGGTCA

TGATTTATCAGAATGGCTAAAGGGGTGTTCTGTGCGTCTGAAAACTGACT

CAAGCTATAATAACTGG

Mature Mouse SLLP2 amino acid Sequence (SEQ ID NO:
16):
KIYERCELAKKLEEAGLDGFKGYTVGDWLCVAHYESGFDTSFVDHNPDGS

SEYGIFQLNSAWWCNNGITPTQNLCNIDCNDLLNRHILDDIICAKRVASS

HKSMKAWDSWTQHCAGHDLSEWLKGCSVRLKTDSSYNNW

Human SLLP2 cDNA sequence (SEQ ID NO: 17):
CTGGGAGGGCTTACAGGTGCCATAATGAAGGCCTGGGGCACTGTGGTAGT

GACCTTGGCCACGCTGATGGTTGTCACTGTGGATGCCAAGATCTATGAAC

GCTGCGAGCTGGCGGCAAGACTGGAGAGAGCAGGGCTGAACGGCTACAAG

GGCTACGGCGTTGGAGACTGGCTGTGCATGGCTCATTATGAGAGTGGCTT

TGACACCGCCTTCGTGGACCACAATCCTGATGGCAGCAGTGAATATGGCA

TTTTCCAACTGAATTCTGCCTGGTGGTGTGACAATGGCATTACACCCACC

AAGAACCTCTGCCACATGGATTGTCATGACCTGCTCAATCGCCATATTCT

GGATGACATCAGGTGTGCCAAGCAGATTGTGTCCTCACAGAATGGGCTTT

CTGCCTGGACTTCTTGGAGGCTACACTGTTCTGGCCATGATTTATCTGAA

TGGCTCAAGGGGTGTGATATGCATGTGAAAATTGATCCAAAAATTCATCC

ATGACTCAGATTCGAAGAGACAGATTTTATCTTCCTTTCATTTCTTTCTC

TTGTGCATTTAATAAAGGATGGTATCTATAAACAATGC

Human SLLP2 Amino acid sequence (SEQ ID NO: 18):
MKAWGTVVVTLATLMVVTVDAKIYERCELAARLERAGLNGYKGYGVGDWL

CMAHYESGFDTAFVDHNPDGSSEYGIFQLNSAWWCDNGITPTKNLCHMDC

HDLLNRHILDDIRCAKQIVSSQNGLSAWTSWRLHCSGHDLSEWLKGCDMH

VKIDPKIHP
```

Proof of the sperm specificity of expression of SLLP2 is provided, as indicated by northern blot analyses of spleen, thymus, prostate, testis, ovary, small intestine, colon, and leukocytes. See also the grid, where the square labeled F8 represents testis and the square D12 represents the gene as cloned and expressed in bacteria.

Recombinant human SLLP2 ("rechSLLP2") was prepared and expressed in E. coli. Antibodies were prepared against the recombinant SLLP2. It was then shown by immuno-electron microscopy that human SLLP2 protein is localized to the sperm acrosomal region in human sperm. The alignment of human SLLP2 protein with it homologues is shown. Soluble human SLLP2 was also isolated and purified, as was mouse SLLP2.

To analyze the biologic activity of human SLLP2, it was determined whether it would bind to an egg, in this case, a mouse egg. The results of this experiment demonstrate that human SLLP2 can indeed bind with mouse eggs, i.e., cross-species binding.

For comparison to the use of human sperm SLLP2, an experiment was performed to determine if purified mouse SLLP2 would bind to Zona intact mouse eggs. The results demonstrate that the sperm protein mSLLP2 does indeed bind to mouse eggs. The next experiment showed that mouse SLLP2 would bind to Zona-free mouse eggs. Competitive assays were then performed to determine whether the addition of recombinant mouse SLLP2 to a mixture of mouse sperm and mouse eggs could inhibit binding of sperm and eggs. Various amounts of recombinant mouse SLLP2 were added (5, 25, 50, 100, and 200 µg/ml) and the number of sperm bound per egg was determined. Relative to BSA (200 µg/ml) or PBS controls, the addition of recombinant mouse SLLP2 was able to reduce the amount of binding occurring between sperm and egg.

Next, it was determined whether recombinant mouse SLLP2 could inhibit mouse sperm-egg fusion. In groups treated with recombinant mouse SLLP2 the number of sperm fused per egg was reduced to about 0.1 sperm fused per egg, at concentrations of 100 or 200 µg/ml recombinant mouse SLLP2, relative to BSA and PBS control treatments.

Next, it was determined whether recombinant mouse SLLP2 could actually inhibit or reduce fertilization of mouse eggs with mouse sperm. Recombinant mouse SLLP2 at concentrations of 25, 50, 100, and 200 µg/ml was incubated with sperm and egg, and compared to BSA and PBS controls as described above. It can be seen that fertilization occurred at a rate of about 75% in the BSA and PBS controls groups. However, the addition of recombinant mouse ("rm") SLLP2 inhibited fertilization in a dose-dependent fashion, with 200 µg/ml rmSLLP2 nearly totally inhibiting fertilization. Also provided are comparisons of human SLLP2 to other mammalian sequences, and well as a comparison indicating the conservation of SLLP2 ortholog in dogs.

Identification and Characterization of a Novel Mouse Egg Specific TolA Protein (MET)

This novel egg protein was screened through the protein-protein interaction assay and it was cloned from cDNA library of mouse ovary. This protein appears to be an important pre-patterning protein in mouse eggs and highly regulated in early embryonic development. MET belongs to a TolA (egg specific) family and has a big alanine rich region, which is a feature of this family.

Screening of Putative Egg Receptors for the Mouse Acrosomal Sperm Protein SLLP1 Using BIACORE®

BIACORE® systems define the characteristics of proteins in terms of their specificity of interaction with other molecules, the rates at which they interact (binding and dissociation), and their affinity (how tightly they bind to another molecule).

The application of BIACORE®'s SPR (Surface plasmon resonance) technology is within the field of proteomics to fish out proteins of interest with subsequent mass spectrometric identification. Purified recombinant SLLP 1 was bound on the sensor chip surface and ligand fishing was done with complete mouse egg lysate (1000 zona free eggs) bound to SLLP1, with subsequent identification by mass spectrometry. A number of proteins were screened with the mass spec data and a novel mouse egg specific TolA-like protein (MET) was selected for further characterization, as it was a novel TolA protein and EST data base was very specific to egg and preimplanted embryos. This gene is localized on mouse chromosome number 9 and belongs to the TolA family. The TolA family consists of several bacterial TolA proteins as well as two eukaryotic proteins of currently unknown function. In bacteria, Tol proteins are involved in the translocation of group A colicins. Colicins are bacterial protein toxins, which are active against *Escherichia coli* and other related species. MET protein is also referred to as a "colicin uptake protein" herein. TolA is anchored to the cytoplasmic membrane by a single membrane spanning segment near the N-terminus, leaving most of the protein exposed to the periplasm.

MET contains a TolA domain and a homologous protein is present in periplasm of *E. coli* and that how it's presence in mouse eggs seems to be important from evolutionary point of view. Bioinformatic analysis showed that MET has four Protein Kinase C phosphorylation sites, six Casein Kinase II phosphorylation sites and one Tyrosine Kinase phosphorylation site.

Cloning and Expression of MET

A complete cDNA encoding 440 amino acids was amplified from cDNA library (Ambion) of mouse ovary and cloned in pET expression vector to express this protein as a fusion protein in *E. coli* (BL21) cells. The mRNA was found to be 1621 bases long. A splice variant of 416 amino acids was found. All the clones were sequenced to check the correct reading frame and a variant was found coding for the same protein with a 24 amino acid fragment deletion. Alignment of the variant with the normal sequence is provided. The MET nucleic acid (full length/normal and variant) sequences and the protein (full/normal and variant) are as follows:

MET-N Nucleic acid sequence
(SEQ ID NO: 1)
atggcctctctgaagaggtttcagacgctcgtgcccctggatcacaaaca aggtaccttatttgaaattattggagagcccaagttgcccaagtggttcc atgtcgaatgcctggaagatccaaaaagactgtacgtggaacctcggcta ctggaaatcatgtttggtaaggatggagagcacatcccacatcttgaatc tatgttgcacaccctgatacatgtgaacgtgtggggccctgaaaggcgag ctgagatttggatattcggaccgccgcctttccgaagggacgttgaccgg atgctcactgatctggctcactattgccgcatgaaactgatggaaataga ggctctggaggctggagttgagcgtcgtcgtatggcggcccataaggctg ccacccagcctgctcccgtgaaggtccgcgaggctgcccctcggcccgct tccgtgaaggtccctgagacgccacccagcctgctcccgtgaaggtccg cgaggctgcccctcagcccgctccggtgcaggaggtccgcgaggctgccc ctcagcaggcttccgtgcaggaggaggtccgcgaggctgccaccgagcag gctcccgtgcaggaggtccgcgaggctgccaccgagcaggctcccgtgca ggaggtcagcgaggctgccaccgagcaggctcccgtgcaggaggtcaacg aggctgccaccgagcaggcttccgtgcaggcggtccgcgaggctgccacc cggccggctcccgggaaggtccgcaaggcggccacccagccggctccggt gcaggtttgccaggaggccacccagttggctcccgtgaaggtccgcgagg cggccacccagccggcttccgggaaggtccgcgaggcggccacccagttg gctcctgtgaaggtccgcaaggcagccacccagttggctcctgtgaaggt ccacgaggcggccacccagccggctccggggaaggtcagcgatgctgcca cgcagtcggcttcggtgcaggttcgtgaggctgccacgcagctgtctccc gtggaggccactgatactagccagttggctcaggtgaaggctgatgaagc ctttgcccagcacacttcaggggaggcccaccaggttgccaatgggcagt ctcccattgaagtctgtgagactgccaccgggcagcattctctagatgtc tctaggccttgtcccagaagtgtcctgaggttttttgagtgggagaccca gagttgtttggatggcagctatgtcatagttcagcctccaagggatgcct gggaatcatttatcatatta MET-V Nucleic acid sequence
(SEQ ID NO: 3)
atggcctctctgaagaggtttcagacgctcgtgcccctggatcacaaaca aggtaccttatttgaaattattggagagcccaagttgcccaagtggttcc atgtcgaatgcctggaagatccaaaaagactgtacgtggaacctcggcta ctggaaatcatgtttggtaaggatggagagcacatcccacatcttgaatc tatgttgcacaccctgatacatgtgaacgtgtggggccctgaaaggcgag ctgagatttggatattcggaccgccgcctttccgaagggacgttgaccgg atgctcactgatctggctcactattgccgcatgaaactgatggaaataga ggctctggaggctggagttgagcgtcgtcgtatggcggcccataaggctg ccacccagcctgctcccgtgaaggtccgcgaggctgcccctcagcccgct ccggtgcaggaggtccgcgaggctgcccctcagcaggcttccgtgcagga ggaggtccgcgaggctgccaccgagcaggctcccgtgcaggaggtccgcg aggctgccaccgagcaggctcccgtgcaggaggtcagcgaggctgccacc gagcaggctcccgtgcaggaggtcaacgaggctgccaccgagcaggcttc cgtgcaggcggtccgcgaggctgccaccggccggctcccgggaaggtcc gcaaggcggccacccagccggctccggtgcaggtttgccaggaggccacc cagttggctcccgtgaaggtccgcgaggcggccacccagccggcttccgg gaaggtccgcgaggcggccacccagttggctcctgtgaaggtccgcaagg cagccacccagttggctcctgtgaaggtccacgaggcggccacccagccg gctccggggaaggtcagcgatgctgccacgcagtcggcttcggtgcaggt tcgtgaggctgccacgcagctgtctcccgtggaggccactgatactagcc agttggctcaggtgaaggctgatgaagcctttgcccagcacacttcaggg gaggcccaccaggttgccaatgggcagtctcccattgaagtctgtgagac tgccaccgggcagcattctctagatgtctctaggccttgtcccagaagt gtcctgaggttttttgagtgggagacccagagttgtttggatggcagctat gtcatagttcagcctccaagggatgcctgggaatcatttatcatatta MET-N Amino Acid Sequence

```
                                                 (SEQ ID NO: 2)
M A S L K R F Q T L V P L D H K Q G T L F E I I G
E P K L P K W F H V E C L E D P K R L Y V E P R L
L E I M F G K D G E H I P H L E S M L H T L I H V
N V W G P E R R A E I W I F G P P P F R R D V D R
M L T D L A H Y C R M K L M E I E A L E A G V E R
R R M A A H K A A T Q P A P V K V R E A A P R P A
S V K V P E T A T Q P A P V K V R E A A P Q P A P
V Q E V R E A A P Q Q A S V Q E E V R E A A T E Q
A P V Q E V R E A A T E Q A P V Q E V S E A A T E
Q A P V Q E V N E A A T E Q A S V Q A V R E A A T
R P A P G K V R K A A T Q P A P V Q V C Q E A T Q
L A P V K V R E A A T Q P A S G K V R E A A T Q L
A P V K V R K A A T Q L A P V K V H E A A T Q P A
P G K V S D A A T Q S A S V Q V R E A A T Q L S P
V E A T D T S Q L A Q V K A D E A F A Q H T S G E
A H Q V A N G Q S P I E V C E T A T G Q H S L D V
S R A L S Q K C P E V F E W E T Q S C L D G S Y V
I V Q P P R D A W E S F I I L

MET-V Amino Acid sequence
                                                 (SEQ ID NO: 4)
M A S L K R F Q T L V P L D H K Q G T L F E I I G
E P K L P K W F H V E C L E D P K R L Y V E P R L
L E I M F G K D G E H I P H L E S M L H T L I H V
N V W G P E R R A E I W I F G P P P F R R D V D R
M L T D L A H Y C R M K L M E I E A L E A G V E R
R R M A A H K A A T Q P A P V K V R E A A P Q P A
P V Q E V R E A A P Q Q A S V Q E E V R E A A T E
Q A P V Q E V R E A A T E Q A P V Q E V S E A A T
E Q A P V Q E V N E A A T E Q A S V Q A V R E A A
T R P A P G K V R K A A T Q P A P V Q V C Q E A T
Q L A P V K V R E A A T Q P A S G K V R E A A T Q
L A P V K V R K A A T Q L A P V K V H E A A T Q P
A P G K V S D A A T Q S A S V Q V R E A A T Q L S
P V E A T D T S Q L A Q V K A D E A F A Q H T S G
E A H Q V A N G Q S P I E V C E T A T G Q H S L D
V S R A L S Q K C P E V F E W E T Q S C L D G S Y
V I V Q P P R D A W E S F I I L
```

Both MET protein sequences were expressed with the pET vector after transformation of bacterial cells with plasmids encoding for fusion proteins, and then induced with 1 mM IPTG (isopropyl-1-thio-β-D-galactopyranoside). The predicted size of the full length protein was 48.4 kD, and the predicted size of the variant with the 24 amino acid deletion was 45.76 kD. Both the expressed and induced proteins were found running comparatively higher on SDS-PAGE than predicted molecular weights, which could be due to post-translational changes in the bacterial cells.

MET was found to accumulate in inclusion bodies. Therefore, bacterial cell lysate was used to purify MET with a Nickel-column, as His-tag of fusion protein bound to Nickel ions. After purification of MET appeared to be a pure single band on SDS-PAGE. The alanine rich TolA-like domain in MET has been highlighted.

Immuno Characterization of MET in Mouse Eggs

Complete purified MET protein was used to raise antibodies in Guinea pigs.

Preimmune screening of these Guinea pigs was done with egg lysate from 100 mouse eggs. Immunization was done in three animals with a primary dose of 150 μg of purified protein, and two more booster doses of 150 μg in three weeks interval. Antibody titer was checked and it was found that 50 ng of purified protein was enough to get good signal, even at 50,000 dilution. At the same time, two animals were used for adjuvant control—which were negative and did not give any signal with purified recombinant MET.

These antibodies were used to characterize the native form of MET in mouse eggs. Western analysis was done with 100 Zona Intact eggs, using the above antibodies. One strong signal appeared at its predicted size of 48.4 kD, but at the same time one more faint band appeared as it was in bacterial recombinant of around 65 kD, which proves that the post translational changes are different in bacterial recombinant MET and in it's native form in the mouse eggs.

Localization of Zinc MET in Mouse Eggs

Expression of MET was found to be localized in mouse ovary sections, and to be very much egg specific protein, without cross-reacting with cumulus cells. Some permeable fixed eggs were also checked for MET localization and it was observed that MET is abundantly present in the egg cytoplasm. Blastocysts were also checked for MET localization. It was found that MET is expressed in the early blastocyst, but that expression is reduced in the late blastocyst. Such segregation to specific blastomeres may be related to pre-patterning.

An experiment was designed to examine MET's role during early embryo development and its localization was studied in all the developmental stages of in-vitro fertilized eggs through the blastocyst stage. It was found that MET is more abundant at the stage of germinal vesicle and gradually reduced after fertilization, but localization seemed to be very specific at the two cell and four cell stages, and apparently appears to be involved in prepatterning and polarity of embryo. However, in the late blastocyst stage it remained only in the peripheral cells, which can be a marker for trophectoderm cells.

Protein-Protein Interaction of MET and SLLP1 (Far-Western Analysis) MET was discovered from mouse eggs as an interactive partner of Sperm acrosomal protein SLLP1, therefore a farwestern analysis was designed to prove the evidence of their binding. To that end, 7 μg of recombinant MET was loaded on 12% SDS-PAGE and transferred to nitrocellulose. The membrane was overlaid (OL) with recombinant SLLP1 (2 μg/ml) and probed with anti-SLLP1 monoclonal antibody and secondary antibody. A strong signal was observed with purified MET, providing further proof that MET binds with SLLP1, and is perhaps an SLLP receptor.

Summary

A full length MET protein and one splice variant were cloned and purified. This protein is a mammalian egg specific TolA protein, and by EST database was shown only in fertilized and unfertilized eggs. According to the known characteristics of the TolA family, MET has a TolA domain of 241 amino acid residues which is highly Alanine rich.

It is shown herein that MET is abundant in egg cytoplasm, particularly in cortex. It may segregate to subsets of blastomeres, indicating that MET may provide evidence of pre-patterning and polarity in the egg. MET's localization with specific expression patterns at different developmental stages of egg and embryo proved that it is a very stage specific protein and may be related to pluripotency of the embryonic cells, and later is related to pre-patterning of embryos. Met transcripts and protein are exclusively oocyte and are preimplanted embryo specific, offers a selective window of targeting as an excellent target for contraceptive vaccinogen.

ZEP, a Novel Egg Protein

The following experiments disclose a novel egg surface receptor (called ZEP below) which interacts with an intra-acrosomal protein, SLLP1. This novel egg receptor for SLLP was screened and identified through a protein-protein interaction assay and was cloned from a mouse ovary cDNA library. This protein appears to be important in sperm binding as well as in early embryonic development (see below). It belongs to a metalloprotease (egg specific) family and has a specific Zinc binding signature. Because it appears to be a Zinc Endopeptidase, it is called ZEP herein.

Further Screening of Putative Egg Receptors which Bind to the Intra Acrosomal Sperm Protein SLLP1 Using BIACORE®

BIACORE® systems can be used to define the characteristics of proteins in terms of their specificity of interaction with other molecules, the rates at which they interact (binding and dissociation), and their affinity (how tightly they bind to another molecule).

BIACORE®'s SPR (Surface plasmon resonance) technology was used to fish out proteins of interest. Purified recombinant SLLP 1 was bound on the sensor chip surface and ligand fishing was done with complete mouse egg lysate (1000 zona free eggs) bound to SLLP1, with subsequent identification by mass spectrometry. Proteins were screened with the mass spectrometry data and ZEP was selected for further characterization as it was a novel metalloprotease and EST data base was very specific to egg and preimplanted embryos.

The gene was localized to mouse chromosome number 2 and belongs to the Astacin family. These proteases require zinc for catalysis and members of this family have an amino terminal propeptide which is cleaved to give the active protease domain.

ZEP showed homology with hatching enzyme EHE7 of Japanese eel *Anguilla japonica*, therefore it was hypothesized that this protein may be performing a similar function in mouse embryo development. Bioinformatic analysis showed that it has 2 glycosylation sites, phosphorylation sites, and myristylation sites; suggestive of a membrane protein. This protein has a typical zinc-binding region signature and that is how it becomes a zinc-metallopeptidase. Transmembrane topology also predicted a strong transmembrane domain at N-terminal of the protein.

Cloning and Expression of Zinc Endopeptidase (ZEP)

A complete cDNA encoding a 414 amino acid peptide was amplified from cDNA library (Ambion) of mouse ovary and cloned in pET expression vector to express this protein as a fusion protein in *E. coli* (BL21) cells. All the clones were sequenced to check the correct reading frame and two more variants were found coding for the same protein, one with 34 amino acid deletion and another variant with 34 amino acid deletion and 9 amino acid insertion. Alignment of all the variants (normal and two variants) of Zinc Endopeptidase is given. The mRNA is 2377 nucleotides long.

All the splice variants were expressed with a pET vector after the transformation of bacterial cells with the plasmids encoding for fusion proteins, and were then induced with 1 mM IPTG (isopropyl-1-thio-β-D-galactopyranoside). Predicted sizes of normal (N) protein was 45.5 kD, variant-1 (V1) with 34 amino acid deletion and 9 amino acid insertion was 43.12 kD and variant-2 (V2) with 34 amino acid deletion was 41.8 kD. All the expressed and induced proteins were in an SDS-PAGE analysis with their expected size.

This protein was found to accumulate in inclusion bodies. Therefore, bacterial cell lysate was used to purify this protein with Nickel-column, as His-tag of fusion protein bound to Nickel ions. After purification of ZEP protein, it was observed that there was an autolytic cleavage and two bands were detected by SDS-PAGE, including a new lower molecular weight band of about 25 kD. N-terminal sequencing was done on this lower band and the cleavage site was found after 204 amino acids. It is not yet clear how this protein is cleaved at this particular site, but the sequence data explain the transmembrane domain, zinc-binding signature and the cleavage site in the amino acid sequence of ZEP. Additionally, an analysis of the ZEP amino acid sequence further suggested a transmembrane structure (as indicated graphically—not shown: TMpred output suggested a transmembrane topology with the preferred model comprising the N-terminus outside with one strong transmembrane helices, and a total score: 755 o-i 122-152 (31)).

The nucleic acid and amino acid sequences of the normal (N) ZEP and the two variants (V1 and V2) disclosed herein are as follows:

```
ZEP-N Nucleic acid sequence
                                       (SEQ ID NO: 5)
atgggagcaccctcagcatccagatgttctggagtctgcagtaccagtgt tccagaaggcttcactcctgagggaagcccggtatttcaggacaaggaca tccccgcaattaaccaagggctcatctcagaggagacccagaaagcagc ttcctggtagaaggggacattatccggccaagcccttccgattgttgtc agtgaccaataataaatggcccaagggcgttggtggctttgtggagatcc ccttcctgctttccagaaagtatgatgaactcagccgccgggtcattatg gatgcctttgctgagtttgaacgtttcacatgcatccggtttgttgccta ccatggtcagagagactttgtttccattcttcctatggcggggtgtttct ctggtgtgggacgcagtggagggatgcaggtggtgtccttggcacccact tgtctccggaagggccgaggcattgtcctacatgagctcatgcacgtact tggcttctggcatgagcattcacgggcagatcgggaccgctacatccaag tcaactggaacgagatcctcccgggctttgaaatcaacttcatcaagtca cggagtaccaatatgttagttccctatgactactcatctgtgatgcatta tgggagatttgccttcagctggcgtgggcagcccaccatcataccactct ggacctccagtgttcacattggccagcgatggaacctgagtacctcagat atcacccgggtctgcaggctgtataactgcagccggagtgtccctgactc ccacgggagagggtttgaggcccagagtgatggaagcagcctcaccctg cctctatatcacgtctacaaagacttctcgaggcactgtcagaggaatct
``` ggaagctctgcccctagtggctccaggactggaggccagagtattgccgg
gcttggtaacagccagcaaggatgggagcatcctcctcagagcacattca
gtgtgggagccttggcaagaccacctcagatgctagccgatgcttcaaaa
tcggggcctggagcaggtgcagacagcttgtctctagagcagttccagct
agcccaggcccccactgtacctcttgctctatttccagaagccagagaca
agccagcacctatccaagatgcctttgagaggctagctccacttccagga
ggctgtgcacctggaagtcacattagagaggtgcccagagac ZEP-V1 Nucleic acid sequence (SEQ ID NO: 7)

atgggagcaccctcagcatccagatgttctggagtctgcagtaccagtgt
tccagaaggcttcactcctgagggaagcccggtatttcaggacaaggaca
tccccgcaattaaccaagggctcatctcagaggagaccccagaaagcagc
ttcctggtagaaggggacattatccggccaggggtcagccacggtgtgtc
tttcccagatgaactcagccgccgggtcattatggatgcctttgctgagt
ttgaacgtttcacatgcatccggtttgttgcctaccatggtcagagagac
tttgtttccattcttcctatggcggggtgtttctctggtgtgggacgcag
tggagggatgcaggtggtgtccttggcacccacttgtctccggaagggcc
gaggcattgtcctacatgagctcatgcacgtacttggcttctggcatgag
cattcacgggcagatcgggaccgctacatccaagtcaactggaacgagat
cctcccgggctttgaaatcaacttcatcaagtcacggagtaccaatatgt
tagttccctatgactactcatctgtgatgcattatgggagatttgccttc
agctggcgtgggcagcccaccatcataccactctggacctccagtgttca
cattggccagcgatggaacctgagtacctcagatatcacccgggtctgca
ggctgtataactgcagccggagtgtccctgactcccacgggagagggttt
gaggcccagagtgatggaagcagcctcacccctgcctctatatcacgtct
acaaagacttctcgaggcactgtcagaggaatctggaagctctgcccta
gtggctccaggactggaggccagagtattgccgggcttggtaacagccag
caaggatgggagcatcctcctcagagcacattcagtgtgggagccttggc
aagaccacctcagatgctagccgatgatcaaaatcggggcctggagcagg
tgcagacagcttgtctctagagcagttccagctagcccaggcccccactg
tacctcttgctctatttccagaagccagagacaagccagcacctatccaa
gatgcctttgagaggctagctccacttccaggaggctgtgcacctggaag
tcacattagagaggtgcccagagac ZEP-V2 Nucleic acid sequence (SEQ ID NO: 9)

atgggagcaccctcagcatccagatgttctggagtctgcagtaccagtgt
tccagaaggcttcactcctgagggaagcccggtatttcaggacaaggaca
tccccgcaattaaccaagggctcatctcagaggagaccccagaaagcagc
ttcctgctttccagaaagtatgatgaactcagccgccgggtcattatgga
tgcctttgctgagtttgaacgtttcacatgcatccggtttgttgcctacc
atggtcagagagactttgtttccattcttcctatggcggggtgtttctct
ggtgtgggacgcagtggagggatgcaggtggtgtccttggcacccacttg tctccggaagggccgaggcattgtcctacatgagctcatgcacgtacttg
gcttctggcatgagcattcacgggcagatcgggaccgctacatccaagtc
aactggaacgagatcctcccgggctttgaaatcaacttcatcaagtcacg
gagtaccaatatgttagttccctatgactactcatctgtgatgcattatg
ggagatttgccttcagctggcgtgggcagcccaccatcataccactctgg
acctccagtgttcacattggccagcgatggaacctgagtacctcagatat
cacccgggtctgcaggctgtataactgcagccggagtgtccctgactccc
acgggagagggtttgaggcccagagtgatggaagcagcctcacccctgcc
tctatatcacgtctacaaagacttctcgaggcactgtcagaggaatctgg
aagctctgcccctagtggctccaggactggaggccagagtattgccgggc
ttggtaacagccagcaaggatgggagcatcctcctcagagcacattcagt
gtgggagccttggcaagaccacctcagatgctagccgatgcttcaaaatc
ggggcctggagcaggtgcagacagcttgtctctagagcagttccagctag
cccaggcccccactgtacctcttgctctatttccagaagccagagacaag
ccagcacctatccaagatgcctttgagaggctagctccacttccaggagg
ctgtgcacctggaagtcacattagagaggtgcccagagac ZEP-N Amino acid sequence (SEQ ID NO: 6)

M G A P S A S R C S G V C S T S V P E G F T P E G
S P V F Q D K D I P A I N Q G L I S E E T P E S S
F L V E G D I I R P S P F R L L S V T N N K W P K
G V G G F V E I P F L L S R K Y D E L S R R V I M
D A F A E F E R F T C I R F V A Y H G Q R D F V S
I L P M A G C F S G V G R S G G M Q V V S L A P T
C L R K G R G I V L H E L M H V L G F W H E H S R
A D R D R Y I Q V N W N E I L P G F E I N F I K S
R S T N M L V P Y D Y S S V M H Y G R F A F S W R
G Q P T I I P L W T S S V H I G Q R W N L S T S D
I T R V C R L Y N C S R S V P D S H G R G F E A Q
S D G S S L T P A S I S R L Q R L L E A L S E E S
G S S A P S G S R T G G Q S I A G L G N S Q Q G W
E H P P Q S T F S V G A L A R P P Q M L A D A S K
S G P G A G A D S L S L E Q F Q L A Q A P T V P L
A L F P E A R D K P A P I Q D A F E R L A P L P G
G C A P G S H I R E V P R D

ZEP-V1 Amino acid sequence (SEQ ID NO: 8)

M G A P S A S R C S G V C S T S V P E G F T P E G
S P V F Q D K D I P A I N Q G L I S E E T P E S S
F L V E G D I I R P G V S H G V S F P D E L S R R
V I M D A F A E F E R F T C I R F V A Y H G Q R D
F V S I L P M A G C F S G V G R S G G M Q V V S L

-continued

```
A P T C L R K G R G I V L H E L M H V L G F W H E

H S R A D R D R Y I Q V N W N E I L P G F E I N F

I K S R S T N M L V P Y D Y S S V M H Y G R F A F

S W R G Q P T I I P L W T S S V H I G Q R W N L S

T S D I T R V C R L Y N C S R S V P D S H G R G F

E A Q S D G S S L T P A S I S R L Q R L L E A L S

E E S G S S A P S G S R T G G Q S I A G L G N S Q

Q G W E H P P Q S T F S V G A L A R P P Q M L A D

A S K P G P G A G A D S L S L E Q F Q L A Q A P T

V P L A L F P E A R D K P A P I Q D A F E R L A P

L P G G C A P G S H I R E V P R D

ZEP-V2 Amino acid sequence
                                        (SEQ ID NO: 10)
M G A P S A S R C S G V C S T S V P E G F T P E G

S P V F Q D K D I P A I N Q G L I S E E T P E S S

F L L S R K Y D E L S R R V I M D A F A E F E R F

T C I R F V A Y H G Q R D F V S I L P M A G C F S

G V G R S G G M Q V V S L A P T C L R K G R G I V

L H E L M H V L G F W H E H S R A D R D R Y I Q V

N W N E I L P G F E I N F I K S R S T N M L V P Y

D Y S S V M H Y G R F A F S W R G Q P T I I P L W

T S S V H I G Q R W N L S T S D I T R V C R L Y N

C S R S V P D S H G R G F E A Q S D G S S L T P A

S I S R L Q R L L E A L S E E S G S S A P S G S R

T G G Q S I A G L G N S Q Q G W E H P P Q S T F S

V G A L A R P P Q M L A D A S K S G P G A G A D S

L S L E Q F Q L A Q A P T V P L A L F P E A R D K

P A P I Q D A F E R L A P L P G G C A P G S H I R

E V P R D
```

Immuno Characterization of Zinc Endopeptidase (ZEP) in Mouse Eggs

Purified protein was used to raise antibodies in Guinea pigs. Preimmune screening of these Guinea pigs was done with egg lysate of 100 mouse eggs. Immunization was done in three animals with primary dose of 150 μg of purified protein and two more booster doses of 150 μg in three weeks interval. Antibody titer was checked and it was found that 50 ng of purified protein was enough to get good signal even at 50,000 dilution. Concurrently, two animals were used for adjuvant control, which proved to be negative and did not give any signal with purified recombinant ZEP.

The antibodies obtained as described were used to characterize the native form of this protein in mouse eggs. Western analysis was done with 150 zona intact and 150 zona free eggs, using the above antibodies as an immune sera screening assay. A signal was found at about 45.5 kD, in both the zona intact and zona free eggs. However, two more bands, which migrated at about 50 kD and 32 kD, were also observed. It is possible that this protein exists in different forms in the eggs, or different spliced variants may be coding for different sizes of similar proteins.

Localization of Zinc Endopeptidase (ZEP) in Mouse Eggs

It was found that ZEP is egg specific and does not cross react with cumulus cells. Immunolocalization of zinc-peptidase in ovary sections is localized, and is very much egg specific, including secondary and tertiary follicles. It was further observed that ZEP is localized on the egg surface in the microvillar region. Some blastocysts were also checked for the ZEP localization. ZEP is located on the egg surface in the microvillar region. Also found was a faint signal in the form of patches. To determine ZEP's developmental regulation, its localization was checked in all the developmental stages of in-vitro fertilized eggs through the blastocyst stage and it was found that ZEP is more abundant at the stage of germinal vesicle and gradually reduced after fertilization. In the blastocyst stage it remained in only some of the peripheral cells.

Protein-Protein Interaction of ZEP and SLLP1

ZEP was picked up from mouse eggs as an interactive partner of the sperm acrosomal protein SLLP1. Therefore, to verify the interaction of ZEP and SLLP1 in the native form of the eggs; co-localization was assayed on the egg surface. Mouse eggs were incubated with 10 μg/ml of recombinant SLLP1 for an hour and then with ZEP and SLLP1 antibodies simultaneously for another hour. A secondary antibody of ZEP was cy3 conjugated and a secondary antibody of SLLP1 was FITC conjugated. To compare localization, images were captured separately and merged after that. The ZEP signal was present only in the microvillar region, whereas the major signal for SLLP1 was located in microvillar region and spread little bit in the perivitelline space. The data demonstrate that the two proteins are binding with one another, because their signal is completely merged.

To further confirm binding, farwestern analyses were performed to further demonstrate that SLLP1 binds with ZEP. To that end, 7.0 μg of recombinant ZEP was loaded onto a 12% SDS gel, subjected to PAGE, and transferred to a nitrocellulose membrane. The membrane was overlaid (OL) with recombinant SLLP1 (2.0 μg/ml) and probed with anti-SLLP1 monoclonal antibody and secondary antibody. A signal was observed with the upper band of ZEP, but not with the lower band. These data suggest that the N-terminal of ZEP has the SLLP1 binding capability, and further suggest why it does not bind with the C-terminal band when the N-terminal is truncated.

Summary

The present invention discloses a full length ZEP and two splice variants. This protein is a mammalian egg specific Zinc Peptidase. In summary, ZEP is localized at the egg membrane at different developmental stage. Co-localization with SLLP1 at the egg membrane further demonstrates that it binds with Sperm Acrosomal protein SLLP1. Because of the sperm binding capability of ZEP, and its stage specific expression, this protein seems to be important for fertilization and an excellent target for contraceptive vaccinogen.

The invention claimed is:

1. A method of identifying a compound which is an inhibitor of SAS1R, said method comprising:
   (a) adding a test compound to a test sample comprising native SAS1R, wherein said test compound is an antibody that binds to amino acids selected from the group consisting of 26-50, 51-75, 76-100, 101-125, 126-150, 151-175 and 176-200 of SAS1R Variant 2 (SEQ ID NO:6); selected from the group consisting of 26-50, 51-75, 76-100, 101-125, 136-150, 151-175 and 176-200 of SAS1R Variant I (SEQ ID NO: 19); or selected from the group consisting of 26-50, 51-75, 76-100, 100-125, 126-150, 151-175 and 176-200 of SAS1R Variant I (SEQ ID NO:23);
   (b) analyzing the level of SAS1R activity or expression in said test sample with the level of SAS1R activity or expression in an otherwise identical sample comprising SAS1R not subjected to a test compound;
   (c) wherein a lower level of SAS1R activity or expression in said test sample subjected to a test compound compared with the level of SAS1R activity or expression in said otherwise identical sample is an indication that said test compound is an inhibitor of SAS1R; and
   (d) thereby identifying a compound which is an inhibitor of SAS1R.

2. The method of claim 1, wherein said SAS1R activity is protease activity.

3. The method of claim 1, wherein said SAS1R activity is interaction with a SLLP protein.

4. The method of claim 1, wherein said antibody is selected from the group consisting of a polyclonal antibody, a monoclonal antibody, a chimeric antibody, and a synthetic antibody.

* * * * *

SEQUENCE LISTING

<160> NUMBER OF SEQ ID NOS: 29

<210> SEQ ID NO 1
<211> LENGTH: 1320
<212> TYPE: DNA
<213> ORGANISM: Mus musculus

<400> SEQUENCE: 1

| | | | | | |
|---|---|---|---|---|---|
| atggcctctc | tgaagaggtt | tcagacgctc | gtgcccctgg | atcacaaaca | aggtacctta | 60 |
| tttgaaatta | ttggagagcc | caagttgccc | aagtggttcc | atgtcgaatg | cctggaagat | 120 |
| ccaaaaagac | tgtacgtgga | acctcggcta | ctggaaatca | tgtttggtaa | ggatggagag | 180 |
| cacatcccac | atcttgaatc | tatgttgcac | accctgatac | atgtgaacgt | gtggggccct | 240 |
| gaaaggcgag | ctgagatttg | gatattcgga | ccgccgcctt | tccgaaggga | cgttgaccgg | 300 |
| atgctcactg | atctggctca | ctattgccgc | atgaaactga | tggaaataga | ggctctggag | 360 |
| gctggagttg | agcgtcgtcg | tatggcggcc | cataaggctg | ccacccagcc | tgctcccgtg | 420 |
| aaggtccgcg | aggctgcccc | tcggcccgct | tccgtgaagg | tccctgagac | ggccacccag | 480 |
| cctgctcccg | tgaaggtccg | cgaggctgcc | cctcagcccg | ctccggtgca | ggaggtccgc | 540 |
| gaggctgccc | ctcagcaggc | ttccgtgcag | gaggaggtcc | gcgaggctgc | caccgagcag | 600 |
| gctcccgtgc | aggaggtccg | cgaggctgcc | accgagcagg | ctcccgtgca | ggaggtcagc | 660 |
| gaggctgcca | ccgagcaggc | tcccgtgcag | gaggtcaacg | aggctgccac | cgagcaggct | 720 |
| tccgtgcagg | cggtccgcga | ggctgccacc | cggccggctc | ccgggaaggt | ccgcaaggcg | 780 |
| gccacccagc | cggctccggt | gcaggtttgc | caggaggcca | cccagttggc | tcccgtgaag | 840 |
| gtccgcgagg | cggccacccca | gccggcttcc | gggaaggtcc | gcgaggcggc | cacccagttg | 900 |
| gctcctgtga | aggtccgcaa | ggcagccacc | cagttggctc | ctgtgaaggt | ccacgaggcg | 960 |
| gccacccagc | cggctccggg | gaaggtcagc | gatgctgcca | cgcagtcggc | ttcggtgcag | 1020 |
| gttcgtgagg | ctgccacgca | gctgtctccc | gtggaggcca | ctgatactag | ccagttggct | 1080 |
| caggtgaagg | ctgatgaagc | ctttgcccag | cacacttcag | ggaggcccca | ccaggttgcc | 1140 |
| aatgggcagt | ctcccattga | agtctgtgag | actgccaccg | ggcagcattc | tctagatgtc | 1200 |
| tctagggcct | tgtcccagaa | gtgtcctgag | gttttttgagt | gggagaccca | gagttgtttg | 1260 |
| gatggcagct | atgtcatagt | tcagcctcca | agggatgcct | gggaatcatt | tatcatatta | 1320 |

<210> SEQ ID NO 2
<211> LENGTH: 440
<212> TYPE: PRT
<213> ORGANISM: Mus musculus

<400> SEQUENCE: 2

Met Ala Ser Leu Lys Arg Phe Gln Thr Leu Val Pro Leu Asp His Lys
 1               5                  10                  15

Gln Gly Thr Leu Phe Glu Ile Ile Gly Glu Pro Lys Leu Pro Lys Trp
             20                  25                  30

Phe His Val Glu Cys Leu Glu Asp Pro Lys Arg Leu Tyr Val Glu Pro
         35                  40                  45

Arg Leu Leu Glu Ile Met Phe Gly Lys Asp Gly Glu His Ile Pro His
     50                  55                  60

Leu Glu Ser Met Leu His Thr Leu Ile His Val Asn Val Trp Gly Pro
 65                  70                  75                  80

Glu Arg Arg Ala Glu Ile Trp Ile Phe Gly Pro Pro Pro Phe Arg Arg
                 85                  90                  95

```
Asp Val Asp Arg Met Leu Thr Asp Leu Ala His Tyr Cys Arg Met Lys
                100                 105                 110

Leu Met Glu Ile Glu Ala Leu Glu Ala Gly Val Glu Arg Arg Met
        115                 120                 125

Ala Ala His Lys Ala Ala Thr Gln Pro Ala Pro Val Lys Val Arg Glu
130                 135                 140

Ala Ala Pro Arg Pro Ala Ser Val Lys Val Pro Glu Thr Ala Thr Gln
145                 150                 155                 160

Pro Ala Pro Val Lys Val Arg Glu Ala Ala Pro Gln Pro Ala Pro Val
                165                 170                 175

Gln Glu Val Arg Glu Ala Ala Pro Gln Gln Ala Ser Val Gln Glu Glu
                180                 185                 190

Val Arg Glu Ala Ala Thr Glu Gln Ala Pro Val Gln Glu Val Arg Glu
            195                 200                 205

Ala Ala Thr Glu Gln Ala Pro Val Gln Glu Val Ser Glu Ala Ala Thr
        210                 215                 220

Glu Gln Ala Pro Val Gln Glu Val Asn Glu Ala Ala Thr Glu Gln Ala
225                 230                 235                 240

Ser Val Gln Ala Val Arg Glu Ala Ala Thr Arg Pro Ala Pro Gly Lys
                245                 250                 255

Val Arg Lys Ala Ala Thr Gln Pro Ala Pro Val Gln Val Cys Gln Glu
                260                 265                 270

Ala Thr Gln Leu Ala Pro Val Lys Val Arg Glu Ala Ala Thr Gln Pro
            275                 280                 285

Ala Ser Gly Lys Val Arg Glu Ala Ala Thr Gln Leu Ala Pro Val Lys
        290                 295                 300

Val Arg Lys Ala Ala Thr Gln Leu Ala Pro Val Lys Val His Glu Ala
305                 310                 315                 320

Ala Thr Gln Pro Ala Pro Gly Lys Val Ser Asp Ala Ala Thr Gln Ser
                325                 330                 335

Ala Ser Val Gln Val Arg Glu Ala Ala Thr Gln Leu Ser Pro Val Glu
                340                 345                 350

Ala Thr Asp Thr Ser Gln Leu Ala Gln Val Lys Ala Asp Glu Ala Phe
            355                 360                 365

Ala Gln His Thr Ser Gly Glu Ala His Gln Val Ala Asn Gly Gln Ser
        370                 375                 380

Pro Ile Glu Val Cys Glu Thr Ala Thr Gly Gln His Ser Leu Asp Val
385                 390                 395                 400

Ser Arg Ala Leu Ser Gln Lys Cys Pro Glu Val Phe Glu Trp Glu Thr
                405                 410                 415

Gln Ser Cys Leu Asp Gly Ser Tyr Val Ile Val Gln Pro Pro Arg Asp
                420                 425                 430

Ala Trp Glu Ser Phe Ile Ile Leu
        435                 440

<210> SEQ ID NO 3
<211> LENGTH: 1248
<212> TYPE: DNA
<213> ORGANISM: Mus musculus

<400> SEQUENCE: 3
atggcctctc tgaagaggtt tcagacgctc gtgcccctgg atcacaaaca aggtacctta        60
tttgaaatta ttggagagcc caagttgccc aagtggttcc atgtcgaatg cctggaagat      120
```

```
ccaaaaagac tgtacgtgga acctcggcta ctggaaatca tgtttggtaa ggatggagag      180
cacatcccac atcttgaatc tatgttgcac accctgatac atgtgaacgt gtggggccct      240
gaaaggcgag ctgagatttg gatattcgga ccgccgcctt ccgaaggga cgttgaccgg       300
atgctcactg atctggctca ctattgccgc atgaaactga tggaaataga ggctctggag      360
gctggagttg agcgtcgtcg tatggcggcc cataaggctg ccacccagcc tgctcccgtg      420
aaggtccgcg aggctgcccc tcagcccgct ccggtgcagg aggtccgcga ggctgcccct      480
cagcaggctt ccgtgcagga ggaggtccgc gaggctgcca ccgagcaggc tcccgtgcag      540
gaggtccgcg aggctgccac cgagcaggct cccgtgcagg aggtcagcga ggctgccacc      600
gagcaggctc ccgtgcagga ggtcaacgag gctgccaccg agcaggcttc cgtgcaggcg      660
gtccgcgagg ctgccacccg gccggctccc gggaaggtcc gcaaggcggc cacccagccg      720
gctccggtgc aggtttgcca ggaggccacc cagttggctc ccgtgaaggt ccgcgaggcg      780
gccacccagc cggcttccgg gaaggtccgc gaggcggcca cccagttggc tcctgtgaag      840
gtccgcaagg cagccaccca gttggctcct gtgaaggtcc acgaggcggc cacccagccg      900
gctccgggga aggtcagcga tgctgccacg cagtcggctt cggtgcaggt tcgtgaggct      960
gccacgcagc tgtctcccgt ggaggccact gatactagcc agttggctca ggtgaaggct     1020
gatgaagcct ttgcccagca cacttcaggg gaggcccacc aggttgccaa tgggcagtct     1080
cccattgaag tctgtgagac tgccaccggg cagcattctc tagatgtctc tagggccttg     1140
tcccagaagt gtcctgaggt ttttgagtgg gagacccaga gttgtttgga tggcagctat     1200
gtcatagttc agcctccaag ggatgcctgg gaatcattta tcatatta                  1248
```

<210> SEQ ID NO 4
<211> LENGTH: 416
<212> TYPE: PRT
<213> ORGANISM: Mus musculus

<400> SEQUENCE: 4

Met Ala Ser Leu Lys Arg Phe Gln Thr Leu Val Pro Leu Asp His Lys
 1               5                   10                  15

Gln Gly Thr Leu Phe Glu Ile Ile Gly Glu Pro Lys Leu Pro Lys Trp
             20                  25                  30

Phe His Val Glu Cys Leu Glu Asp Pro Lys Arg Leu Tyr Val Glu Pro
         35                  40                  45

Arg Leu Leu Glu Ile Met Phe Gly Lys Asp Gly Glu His Ile Pro His
     50                  55                  60

Leu Glu Ser Met Leu His Thr Leu Ile His Val Asn Val Trp Gly Pro
 65                  70                  75                  80

Glu Arg Arg Ala Glu Ile Trp Ile Phe Gly Pro Pro Phe Arg Arg
                 85                  90                  95

Asp Val Asp Arg Met Leu Thr Asp Leu Ala His Tyr Cys Arg Met Lys
            100                 105                 110

Leu Met Glu Ile Glu Ala Leu Glu Ala Gly Val Glu Arg Arg Arg Met
        115                 120                 125

Ala Ala His Lys Ala Ala Thr Gln Pro Ala Pro Val Lys Val Arg Glu
    130                 135                 140

Ala Ala Pro Gln Pro Ala Pro Val Gln Glu Val Arg Glu Ala Ala Pro
145                 150                 155                 160

Gln Gln Ala Ser Val Gln Glu Glu Val Arg Glu Ala Ala Thr Glu Gln
                165                 170                 175

```
Ala Pro Val Gln Glu Val Arg Glu Ala Ala Thr Glu Gln Ala Pro Val
            180                 185                 190
Gln Glu Val Ser Glu Ala Ala Thr Glu Gln Ala Pro Val Gln Glu Val
        195                 200                 205
Asn Glu Ala Ala Thr Glu Gln Ala Ser Val Gln Ala Val Arg Glu Ala
    210                 215                 220
Ala Thr Arg Pro Ala Pro Gly Lys Val Arg Lys Ala Ala Thr Gln Pro
225                 230                 235                 240
Ala Pro Val Gln Val Cys Gln Glu Ala Thr Gln Leu Ala Pro Val Lys
                245                 250                 255
Val Arg Glu Ala Ala Thr Gln Pro Ala Ser Gly Lys Val Arg Glu Ala
            260                 265                 270
Ala Thr Gln Leu Ala Pro Val Lys Val Arg Lys Ala Ala Thr Gln Leu
        275                 280                 285
Ala Pro Val Lys Val His Glu Ala Thr Gln Pro Ala Pro Gly Lys
    290                 295                 300
Val Ser Asp Ala Ala Thr Gln Ser Ala Ser Val Gln Val Arg Glu Ala
305                 310                 315                 320
Ala Thr Gln Leu Ser Pro Val Glu Ala Thr Asp Thr Ser Gln Leu Ala
                325                 330                 335
Gln Val Lys Ala Asp Glu Ala Phe Ala Gln His Thr Ser Gly Glu Ala
            340                 345                 350
His Gln Val Ala Asn Gly Gln Ser Pro Ile Glu Val Cys Glu Thr Ala
        355                 360                 365
Thr Gly Gln His Ser Leu Asp Val Ser Arg Ala Leu Ser Gln Lys Cys
    370                 375                 380
Pro Glu Val Phe Glu Trp Glu Thr Gln Ser Cys Leu Asp Gly Ser Tyr
385                 390                 395                 400
Val Ile Val Gln Pro Pro Arg Asp Ala Trp Glu Ser Phe Ile Ile Leu
                405                 410                 415

<210> SEQ ID NO 5
<211> LENGTH: 1242
<212> TYPE: DNA
<213> ORGANISM: Mus musculus

<400> SEQUENCE: 5
atgggagcac cctcagcatc cagatgttct ggagtctgca gtaccagtgt tccagaaggc      60
ttcactcctg agggaagccc ggtatttcag gacaaggaca tccccgcaat taaccaaggg     120
ctcatctcag aggagacccc agaaagcagc ttcctggtag aaggggacat tatccggcca     180
agccctttcc gattgttgtc agtgaccaat aataaatggc ccaagggcgt ggtggctttt     240
gtggagatcc ccttcctgct ttccagaaag tatgatgaac tcagccgccg ggtcattatg     300
gatgcctttg ctgagtttga acgtttcaca tgcatccggt tgttgcctac ccatggtcag     360
agagactttg tttccattct tcctatggcg gggtgtttct ctggtgtggg acgcagtgga     420
gggatgcagg tggtgtcctt ggcacccact tgtctccgga agggccgagg cattgtccta     480
catgagctca tgcacgtact tggcttctgg catgagcatt cacgggcaga tcgggaccgc     540
tacatccaag tcaactggaa cgagatcctc ccgggctttg aaatcaactt catcaagtca     600
cggagtacca atatgttagt tccctatgac tactcatctg tgatgcatta tgggagattt     660
gccttcagct ggcgtgggca gcccaccatc ataccactct ggacctccag tgttcacatt     720
ggccagcgat ggaacctgag tacctcagat atcacccggg tctgcaggct gtataactgc     780
```

```
agccggagtg tccctgactc ccacgggaga gggtttgagg cccagagtga tggaagcagc    840
ctcacccctg cctctatatc acgtctacaa agacttctcg aggcactgtc agaggaatct    900
ggaagctctg cccctagtgg ctccaggact ggaggccaga gtattgccgg gcttggtaac    960
agccagcaag gatgggagca tcctcctcag agcacattca gtgtgggagc cttggcaaga   1020
ccacctcaga tgctagccga tgcttcaaaa tcggggcctg gagcaggtgc agacagcttg   1080
tctctagagc agttccagct agcccaggcc cccactgtac ctcttgctct atttccagaa   1140
gccagagaca agccagcacc tatccaagat gcctttgaga ggctagctcc acttccagga   1200
ggctgtgcac ctggaagtca cattagagag gtgcccagag ac                     1242
```

<210> SEQ ID NO 6
<211> LENGTH: 414
<212> TYPE: PRT
<213> ORGANISM: Mus musculus

<400> SEQUENCE: 6

```
Met Gly Ala Pro Ser Ala Ser Arg Cys Ser Gly Val Cys Ser Thr Ser
 1               5                  10                  15

Val Pro Glu Gly Phe Thr Pro Glu Gly Ser Pro Val Phe Gln Asp Lys
            20                  25                  30

Asp Ile Pro Ala Ile Asn Gln Gly Leu Ile Ser Glu Glu Thr Pro Glu
        35                  40                  45

Ser Ser Phe Leu Val Glu Gly Asp Ile Ile Arg Pro Ser Pro Phe Arg
    50                  55                  60

Leu Leu Ser Val Thr Asn Asn Lys Trp Pro Lys Gly Val Gly Gly Phe
65                  70                  75                  80

Val Glu Ile Pro Phe Leu Leu Ser Arg Lys Tyr Asp Glu Leu Ser Arg
                85                  90                  95

Arg Val Ile Met Asp Ala Phe Ala Glu Phe Glu Arg Phe Thr Cys Ile
            100                 105                 110

Arg Phe Val Ala Tyr His Gly Gln Arg Asp Phe Val Ser Ile Leu Pro
        115                 120                 125

Met Ala Gly Cys Phe Ser Gly Val Gly Arg Ser Gly Gly Met Gln Val
    130                 135                 140

Val Ser Leu Ala Pro Thr Cys Leu Arg Lys Gly Arg Gly Ile Val Leu
145                 150                 155                 160

His Glu Leu Met His Val Leu Gly Phe Trp His Glu His Ser Arg Ala
                165                 170                 175

Asp Arg Asp Arg Tyr Ile Gln Val Asn Trp Asn Glu Ile Leu Pro Gly
            180                 185                 190

Phe Glu Ile Asn Phe Ile Lys Ser Arg Ser Thr Asn Met Leu Val Pro
        195                 200                 205

Tyr Asp Tyr Ser Ser Val Met His Tyr Gly Arg Phe Ala Phe Ser Trp
    210                 215                 220

Arg Gly Gln Pro Thr Ile Ile Pro Leu Trp Thr Ser Val His Ile
225                 230                 235                 240

Gly Gln Arg Trp Asn Leu Ser Thr Ser Asp Ile Thr Arg Val Cys Arg
                245                 250                 255

Leu Tyr Asn Cys Ser Arg Ser Val Pro Asp Ser His Gly Arg Gly Phe
            260                 265                 270

Glu Ala Gln Ser Asp Gly Ser Ser Leu Thr Pro Ala Ser Ile Ser Arg
        275                 280                 285

Leu Gln Arg Leu Leu Glu Ala Leu Ser Glu Glu Ser Gly Ser Ser Ala
```

|     |     |     |     | 290 |     |     |     |     | 295 |     |     |     |     | 300 |

Pro Ser Gly Ser Arg Thr Gly Gly Gln Ser Ile Ala Gly Leu Gly Asn
305                 310                 315                 320

Ser Gln Gln Gly Trp Glu His Pro Pro Gln Ser Thr Phe Ser Val Gly
                325                 330                 335

Ala Leu Ala Arg Pro Pro Gln Met Leu Ala Asp Ala Ser Lys Ser Gly
            340                 345                 350

Pro Gly Ala Gly Ala Asp Ser Leu Ser Leu Glu Gln Phe Gln Leu Ala
        355                 360                 365

Gln Ala Pro Thr Val Pro Leu Ala Leu Phe Pro Glu Ala Arg Asp Lys
    370                 375                 380

Pro Ala Pro Ile Gln Asp Ala Phe Glu Arg Leu Ala Pro Leu Pro Gly
385                 390                 395                 400

Gly Cys Ala Pro Gly Ser His Ile Arg Glu Val Pro Arg Asp
                405                 410

<210> SEQ ID NO 7
<211> LENGTH: 1176
<212> TYPE: DNA
<213> ORGANISM: Mus musculus

<400> SEQUENCE: 7

| atgggagcac cctcagcatc cagatgttct ggagtctgca gtaccagtgt tccagaaggc | 60 |
| ttcactcctg agggaagccc ggtatttcag gacaaggaca tccccgcaat taaccaaggg | 120 |
| ctcatctcag aggagacccc agaaagcagc ttcctggtag aagggggacat tatccggcca | 180 |
| ggggtcagcc acggtgtgtc tttcccagat gaactcagcc gccgggtcat tatggatgcc | 240 |
| tttgctgagt ttgaacgttt cacatgcatc cggtttgttg cctaccatgg tcagagagac | 300 |
| tttgtttcca ttcttcctat ggcggggtgt ttctctggtg tgggacgcag tggagggatg | 360 |
| caggtggtgt ccttggcacc cacttgtctc cggaagggcc gaggcattgt cctacatgag | 420 |
| ctcatgcacg tacttggctt ctggcatgag cattcacggg cagatcggga ccgctacatc | 480 |
| caagtcaact ggaacgagat cctcccgggc tttgaaatca acttcatcaa gtcacggagt | 540 |
| accaatatgt tagttcccta tgactactca tctgtgatgc attatgggag atttgccttc | 600 |
| agctggcgtg gcagcccac catcatacca ctctggacct ccagtgttca cattggccag | 660 |
| cgatggaacc tgagtacctc agatatcacc cgggtctgca ggctgtataa ctgcagccgg | 720 |
| agtgtccctg actccacgg gagagggttt gaggcccaga gtgatggaag cagcctcacc | 780 |
| cctgcctcta tcacgtctct acaaagactt ctcgaggcac tgtcagagga atctggaagc | 840 |
| tctgccccta gtggctccag gactggaggc cagagtattg ccgggcttgg taacagccag | 900 |
| caaggatggg agcatcctcc tcagagcaca ttcagtgtgg agccttggc aagaccacct | 960 |
| cagatgctag ccgatgcttc aaaatcgggg cctggagcag gtgcagacag cttgtctcta | 1020 |
| gagcagttcc agctagccca ggcccccact gtacctcttg ctctatttcc agaagccaga | 1080 |
| gacaagccag cacctatcca agatgccttt gagaggctag ctccacttcc aggaggctgt | 1140 |
| gcacctggaa gtcacattag agaggtgccc agagac | 1176 |

<210> SEQ ID NO 8
<211> LENGTH: 392
<212> TYPE: PRT
<213> ORGANISM: Mus musculus

<400> SEQUENCE: 8

```
Met Gly Ala Pro Ser Ala Ser Arg Cys Ser Gly Val Cys Ser Thr Ser
  1               5                  10                  15

Val Pro Glu Gly Phe Thr Pro Glu Gly Ser Pro Val Phe Gln Asp Lys
             20                  25                  30

Asp Ile Pro Ala Ile Asn Gln Gly Leu Ile Ser Glu Glu Thr Pro Glu
         35                  40                  45

Ser Ser Phe Leu Val Glu Gly Asp Ile Ile Arg Pro Gly Val Ser His
 50                  55                  60

Gly Val Ser Phe Pro Asp Glu Leu Ser Arg Arg Val Ile Met Asp Ala
 65                  70                  75                  80

Phe Ala Glu Phe Glu Arg Phe Thr Cys Ile Arg Phe Val Ala Tyr His
                 85                  90                  95

Gly Gln Arg Asp Phe Val Ser Ile Leu Pro Met Ala Gly Cys Phe Ser
            100                 105                 110

Gly Val Gly Arg Ser Gly Gly Met Gln Val Val Ser Leu Ala Pro Thr
            115                 120                 125

Cys Leu Arg Lys Gly Arg Gly Ile Val Leu His Glu Leu Met His Val
            130                 135                 140

Leu Gly Phe Trp His Glu His Ser Arg Ala Asp Arg Asp Arg Tyr Ile
145                 150                 155                 160

Gln Val Asn Trp Asn Glu Ile Leu Pro Gly Phe Glu Ile Asn Phe Ile
                165                 170                 175

Lys Ser Arg Ser Thr Asn Met Leu Val Pro Tyr Asp Tyr Ser Ser Val
            180                 185                 190

Met His Tyr Gly Arg Phe Ala Phe Ser Trp Arg Gly Gln Pro Thr Ile
            195                 200                 205

Ile Pro Leu Trp Thr Ser Ser Val His Ile Gly Gln Arg Trp Asn Leu
            210                 215                 220

Ser Thr Ser Asp Ile Thr Arg Val Cys Arg Leu Tyr Asn Cys Ser Arg
225                 230                 235                 240

Ser Val Pro Asp Ser His Gly Arg Gly Phe Glu Ala Gln Ser Asp Gly
                245                 250                 255

Ser Ser Leu Thr Pro Ala Ser Ile Ser Arg Leu Gln Arg Leu Leu Glu
            260                 265                 270

Ala Leu Ser Glu Glu Ser Gly Ser Ala Pro Ser Gly Ser Arg Thr
            275                 280                 285

Gly Gly Gln Ser Ile Ala Gly Leu Gly Asn Ser Gln Gln Gly Trp Glu
            290                 295                 300

His Pro Pro Gln Ser Thr Phe Ser Val Gly Ala Leu Ala Arg Pro Pro
305                 310                 315                 320

Gln Met Leu Ala Asp Ala Ser Lys Pro Gly Pro Gly Ala Gly Ala Asp
                325                 330                 335

Ser Leu Ser Leu Glu Gln Phe Gln Leu Ala Gln Ala Pro Thr Val Pro
            340                 345                 350

Leu Ala Leu Phe Pro Glu Ala Arg Asp Lys Pro Ala Pro Ile Gln Asp
            355                 360                 365

Ala Phe Glu Arg Leu Ala Pro Leu Pro Gly Gly Cys Ala Pro Gly Ser
            370                 375                 380

His Ile Arg Glu Val Pro Arg Asp
385                 390

<210> SEQ ID NO 9
<211> LENGTH: 1140
<212> TYPE: DNA
```

<213> ORGANISM: Mus musculus

<400> SEQUENCE: 9

```
atgggagcac cctcagcatc cagatgttct ggagtctgca gtaccagtgt tccagaaggc      60
ttcactcctg agggaagccc ggtatttcag gacaaggaca tccccgcaat taaccaaggg     120
ctcatctcag aggagacccc agaaagcagc ttcctgcttt ccagaaagta tgatgaactc     180
agccgccggg tcattatgga tgcctttgct gagtttgaac gtttcacatg catccggttt     240
gttgcctacc atggtcagag agactttgtt tccattcttc ctatggcggg tgtttctct      300
ggtgtgggac gcagtggagg gatgcaggtg gtgtccttgg cacccacttg tctccggaag     360
ggccgaggca ttgtcctaca tgagctcatg cacgtacttg gcttctggca tgagcattca     420
cgggcagatc gggaccgcta catccaagtc aactggaacg agatcctccc gggctttgaa     480
atcaacttca tcaagtcacg gagtaccaat atgttagttc cctatgacta ctcatctgtg     540
atgcattatg ggagatttgc cttcagctgg cgtgggcagc ccaccatcat accactctgg     600
acctccagtg ttcacattgg ccagcgatgg aacctgagta cctcagatat cacccgggtc     660
tgcaggctgt ataactgcag ccggagtgtc cctgactccc acgggagagg gtttgaggcc     720
cagagtgatg gaagcagcct caccccctgcc tctatatcac gtctacaaag acttctcgag     780
gcactgtcag aggaatctgg aagctctgcc cctagtggct ccaggactgg aggccagagt     840
attgccgggc ttggtaacag ccagcaagga tgggagcatc tcctcagag cacattcagt      900
gtgggagcct tggcaagacc acctcagatg ctagccgatg cttcaaaatc ggggcctgga     960
gcaggtgcag acagcttgtc tctagagcag ttccagctag cccaggcccc cactgtacct    1020
cttgctctat ttccagaagc cagagacaag ccagcaccta tccaagatgc ctttgagagg    1080
ctagctccac ttccaggagg ctgtgcacct ggaagtcaca ttagagaggt gcccagagac    1140
```

<210> SEQ ID NO 10
<211> LENGTH: 380
<212> TYPE: PRT
<213> ORGANISM: Mus musculus

<400> SEQUENCE: 10

```
Met Gly Ala Pro Ser Ala Ser Arg Cys Ser Gly Val Cys Ser Thr Ser
 1               5                  10                  15

Val Pro Glu Gly Phe Thr Pro Glu Gly Ser Pro Val Phe Gln Asp Lys
            20                  25                  30

Asp Ile Pro Ala Ile Asn Gln Gly Leu Ile Ser Glu Glu Thr Pro Glu
        35                  40                  45

Ser Ser Phe Leu Leu Ser Arg Lys Tyr Asp Glu Leu Ser Arg Arg Val
    50                  55                  60

Ile Met Asp Ala Phe Ala Glu Phe Glu Arg Phe Thr Cys Ile Arg Phe
65                  70                  75                  80

Val Ala Tyr His Gly Gln Arg Asp Phe Val Ser Ile Leu Pro Met Ala
                85                  90                  95

Gly Cys Phe Ser Gly Val Gly Arg Ser Gly Gly Met Gln Val Val Ser
            100                 105                 110

Leu Ala Pro Thr Cys Leu Arg Lys Gly Arg Gly Ile Val Leu His Glu
        115                 120                 125

Leu Met His Val Leu Gly Phe Trp His Glu His Ser Arg Ala Asp Arg
    130                 135                 140

Asp Arg Tyr Ile Gln Val Asn Trp Asn Glu Ile Leu Pro Gly Phe Glu
145                 150                 155                 160
```

Ile Asn Phe Ile Lys Ser Arg Ser Thr Asn Met Leu Val Pro Tyr Asp
              165                 170                 175

Tyr Ser Ser Val Met His Tyr Gly Arg Phe Ala Phe Ser Trp Arg Gly
          180                 185                 190

Gln Pro Thr Ile Ile Pro Leu Trp Thr Ser Ser Val His Ile Gly Gln
      195                 200                 205

Arg Trp Asn Leu Ser Thr Ser Asp Ile Thr Arg Val Cys Arg Leu Tyr
  210                 215                 220

Asn Cys Ser Arg Ser Val Pro Asp Ser His Gly Arg Gly Phe Glu Ala
225                 230                 235                 240

Gln Ser Asp Gly Ser Ser Leu Thr Pro Ala Ser Ile Ser Arg Leu Gln
              245                 250                 255

Arg Leu Leu Glu Ala Leu Ser Glu Glu Ser Gly Ser Ser Ala Pro Ser
          260                 265                 270

Gly Ser Arg Thr Gly Gly Gln Ser Ile Ala Gly Leu Gly Asn Ser Gln
      275                 280                 285

Gln Gly Trp Glu His Pro Pro Gln Ser Thr Phe Ser Val Gly Ala Leu
  290                 295                 300

Ala Arg Pro Pro Gln Met Leu Ala Asp Ala Ser Lys Ser Gly Pro Gly
305                 310                 315                 320

Ala Gly Ala Asp Ser Leu Ser Leu Glu Gln Phe Gln Leu Ala Gln Ala
              325                 330                 335

Pro Thr Val Pro Leu Ala Leu Phe Pro Glu Ala Arg Asp Lys Pro Ala
          340                 345                 350

Pro Ile Gln Asp Ala Phe Glu Arg Leu Ala Pro Leu Pro Gly Gly Cys
      355                 360                 365

Ala Pro Gly Ser His Ile Arg Glu Val Pro Arg Asp
  370                 375                 380

<210> SEQ ID NO 11
<211> LENGTH: 384
<212> TYPE: DNA
<213> ORGANISM: Mus musculus

<400> SEQUENCE: 11
aaggtcttca gtcgctgtga gctggccaaa gagatgcatg acttcggtct ggatggctac      60
cggggttata acctggctga ctgggtctgc cttgcttact acacaagtgg cttcaacaca     120
aatgctgtgg atcatgaagc tgatggaagc accaacaatg catcttcca gatcagcagc     180
cggaggtggt gcagaaccct cgcctcgaat ggccccaatc tttgcaggat atactgcact     240
gatttgttga caatgatct caaagattct atcgtctgtg ccatgaagat agttcaagaa     300
cccctgggtc tgggctattg gaagcctgg aggcaccact gccagggcag ggacctcagt     360
gactgggtgg atggctgtga cttc                                            384

<210> SEQ ID NO 12
<211> LENGTH: 128
<212> TYPE: PRT
<213> ORGANISM: Mus musculus

<400> SEQUENCE: 12

Lys Val Phe Ser Arg Cys Glu Leu Ala Lys Glu Met His Asp Phe Gly
  1               5                  10                  15

Leu Asp Gly Tyr Arg Gly Tyr Asn Leu Ala Asp Trp Val Cys Leu Ala
              20                  25                  30

```
Tyr Tyr Thr Ser Gly Phe Asn Thr Asn Ala Val Asp His Glu Ala Asp
         35                  40                  45

Gly Ser Thr Asn Asn Gly Ile Phe Gln Ile Ser Ser Arg Arg Trp Cys
 50                  55                  60

Arg Thr Leu Ala Ser Asn Gly Pro Asn Leu Cys Arg Ile Tyr Cys Thr
 65                  70                  75                  80

Asp Leu Leu Asn Asn Asp Leu Lys Asp Ser Ile Val Cys Ala Met Lys
                 85                  90                  95

Ile Val Gln Glu Pro Leu Gly Leu Gly Tyr Trp Glu Ala Trp Arg His
             100                 105                 110

His Cys Gln Gly Arg Asp Leu Ser Asp Trp Val Asp Gly Cys Asp Phe
         115                 120                 125

<210> SEQ ID NO 13
<211> LENGTH: 820
<212> TYPE: DNA
<213> ORGANISM: Mus musculus

<400> SEQUENCE: 13
gccctggcaa ggttgtgggg gacatcttga gctgaagcag ggttttgagc cactgctgct      60
gctgccattg tcaccatggt ctcagctctg cggggagcac cctgatcag  ggtgcactca     120
agccctgttt cttctccttc tgtgagtgga ccacggaggc tggtgagctg cctgtcatcc     180
caaagctcag ctctgagcca gagtggtggt ggctccacct ctgccgccgg catagaagcc     240
aggagcaggg ctctcagaag gcggtggtgc ccagctggga tcatgttgtt ggccctggtc     300
tgtctgctca gctgcctgct acctccagt gaggccaagc tctacggtcg ttgtgaactg      360
gccagagtgc tacatgactt cgggctggac ggataccggg gatacagcct ggctgactgg     420
gtctgccttg cttatttcac aagcggtttc aacgcagctg cttttggacta cgaggctgat     480
gggagcacca caacgggat cttccagatc aacagccgga ggtggtgcag caacctcacc      540
ccgaacgtcc ccaacgtgtg ccggatgtac tgctcagatt tgttgaatcc taatctcaag     600
gataccgtta tctgtgccat gaagataacc caagagcctc agggtctggg ttactgggag     660
gcctggaggc atcactgcca gggaaaagac ctcactgaat gggtggatgg ctgtgacttc     720
taggatggac ggaaccatgc acagcaggct gggaaatgtg gtttggttcc tgacctaggc     780
ttggaagac aagccagcga ataaaggatg gttgaacgtt                            820

<210> SEQ ID NO 14
<211> LENGTH: 215
<212> TYPE: PRT
<213> ORGANISM: Homo sapiens

<400> SEQUENCE: 14

Met Val Ser Ala Leu Arg Gly Ala Pro Leu Ile Arg Val His Ser Ser
 1               5                  10                  15

Pro Val Ser Ser Pro Ser Val Ser Gly Pro Arg Arg Leu Val Ser Cys
             20                  25                  30

Leu Ser Ser Gln Ser Ser Ala Leu Ser Gln Ser Gly Gly Gly Ser Thr
         35                  40                  45

Ser Ala Ala Gly Ile Glu Ala Arg Ser Arg Ala Leu Arg Arg Arg Trp
 50                  55                  60

Cys Pro Ala Gly Ile Met Leu Leu Ala Leu Val Cys Leu Leu Ser Cys
 65                  70                  75                  80

Leu Leu Pro Ser Ser Glu Ala Lys Leu Tyr Gly Arg Cys Glu Leu Ala
                 85                  90                  95
```

```
Arg Val Leu His Asp Phe Gly Leu Asp Gly Tyr Arg Gly Tyr Ser Leu
            100                 105                 110

Ala Asp Trp Val Cys Leu Ala Tyr Phe Thr Ser Gly Phe Asn Ala Ala
        115                 120                 125

Ala Leu Asp Tyr Glu Ala Asp Gly Ser Thr Asn Asn Gly Ile Phe Gln
    130                 135                 140

Ile Asn Ser Arg Arg Trp Cys Ser Asn Leu Thr Pro Asn Val Pro Asn
145                 150                 155                 160

Val Cys Arg Met Tyr Cys Ser Asp Leu Leu Asn Pro Asn Leu Lys Asp
                165                 170                 175

Thr Val Ile Cys Ala Met Lys Ile Thr Gln Glu Pro Gln Gly Leu Gly
            180                 185                 190

Tyr Trp Glu Ala Trp Arg His His Cys Gln Gly Lys Asp Leu Thr Glu
        195                 200                 205

Trp Val Asp Gly Cys Asp Phe
    210                 215

<210> SEQ ID NO 15
<211> LENGTH: 417
<212> TYPE: DNA
<213> ORGANISM: Mus musculus

<400> SEQUENCE: 15
aagatttatg aacgctgtga gctggcaaag aagctggagg aggctggcct cgatggcttc      60
aaaggctata ctgttggaga ctggctgtgt gtggcacact atgagagtgg ctttgacacc     120
tcttttgtgg accacaatcc agatggcagc agtgaatatg gcattttcca gctgaactct     180
gcctggtggt gtaacaatgg catcacaccc actcagaacc tctgcaacat cgattgtaat     240
gacctgctca accgccatat tctggatgat atcatatgtg ccaagagggt tgcatcctca     300
cataagagta tgaaggcctg ggattcctgg acccagcact gtgccggtca tgatttatca     360
gaatggctaa aggggtgttc tgtgcgtctg aaaactgact caagctataa taactgg       417

<210> SEQ ID NO 16
<211> LENGTH: 139
<212> TYPE: PRT
<213> ORGANISM: Mus musculus

<400> SEQUENCE: 16

Lys Ile Tyr Glu Arg Cys Glu Leu Ala Lys Lys Leu Glu Glu Ala Gly
1               5                   10                  15

Leu Asp Gly Phe Lys Gly Tyr Thr Val Gly Asp Trp Leu Cys Val Ala
            20                  25                  30

His Tyr Glu Ser Gly Phe Asp Thr Ser Phe Val Asp His Asn Pro Asp
        35                  40                  45

Gly Ser Ser Glu Tyr Gly Ile Phe Gln Leu Asn Ser Ala Trp Trp Cys
    50                  55                  60

Asn Asn Gly Ile Thr Pro Thr Gln Asn Leu Cys Asn Ile Asp Cys Asn
65                  70                  75                  80

Asp Leu Leu Asn Arg His Ile Leu Asp Asp Ile Ile Cys Ala Lys Arg
                85                  90                  95

Val Ala Ser Ser His Lys Ser Met Lys Ala Trp Asp Ser Trp Thr Gln
            100                 105                 110

His Cys Ala Gly His Asp Leu Ser Glu Trp Leu Lys Gly Cys Ser Val
        115                 120                 125
```

```
Arg Leu Lys Thr Asp Ser Ser Tyr Asn Asn Trp
    130                 135
```

<210> SEQ ID NO 17
<211> LENGTH: 588
<212> TYPE: DNA
<213> ORGANISM: Homo sapiens

<400> SEQUENCE: 17

```
ctgggagggc ttacaggtgc cataatgaag gcctggggca ctgtggtagt gaccttggcc    60
acgctgatgg ttgtcactgt ggatgccaag atctatgaac gctgcgagct ggcggcaaga   120
ctggagagag cagggctgaa cggctacaag ggctacggcg ttggagactg gctgtgcatg   180
gctcattatg agagtggctt tgacaccgcc ttcgtggacc acaatcctga tggcagcagt   240
gaatatggca ttttccaact gaattctgcc tggtggtgtg acaatggcat tacacccacc   300
aagaacctct gccacatgga ttgtcatgac ctgctcaatc gccatattct ggatgacatc   360
aggtgtgcca agcagattgt gtcctcacag aatgggcttt ctgcctggac ttcttggagg   420
ctacactgtt ctggccatga tttatctgaa tggctcaagg ggtgtgatat gcatgtgaaa   480
attgatccaa aaattcatcc atgactcaga ttcgaagaga cagattttat cttccttca   540 tttctttctc ttgtgcattt aataaaggat ggtatctata acaatgc                 588
```

<210> SEQ ID NO 18
<211> LENGTH: 159
<212> TYPE: PRT
<213> ORGANISM: Homo sapiens

<400> SEQUENCE: 18

```
Met Lys Ala Trp Gly Thr Val Val Thr Leu Ala Thr Leu Met Val
  1               5                  10                  15

Val Thr Val Asp Ala Lys Ile Tyr Glu Arg Cys Glu Leu Ala Ala Arg
             20                  25                  30

Leu Glu Arg Ala Gly Leu Asn Gly Tyr Lys Gly Tyr Gly Val Gly Asp
         35                  40                  45

Trp Leu Cys Met Ala His Tyr Glu Ser Gly Phe Asp Thr Ala Phe Val
 50                  55                  60

Asp His Asn Pro Asp Gly Ser Ser Glu Tyr Gly Ile Phe Gln Leu Asn
 65                  70                  75                  80

Ser Ala Trp Trp Cys Asp Asn Gly Ile Thr Pro Thr Lys Asn Leu Cys
                 85                  90                  95

His Met Asp Cys His Asp Leu Leu Asn Arg His Ile Leu Asp Asp Ile
            100                 105                 110

Arg Cys Ala Lys Gln Ile Val Ser Ser Gln Asn Gly Leu Ser Ala Trp
        115                 120                 125

Thr Ser Trp Arg Leu His Cys Ser Gly His Asp Leu Ser Glu Trp Leu
    130                 135                 140

Lys Gly Cys Asp Met His Val Lys Ile Asp Pro Lys Ile His Pro
145                 150                 155
```

<210> SEQ ID NO 19
<211> LENGTH: 435
<212> TYPE: PRT
<213> ORGANISM: Mus musculus

<400> SEQUENCE: 19

```
Met Gly Ile Met Gly Ser Leu Trp Pro Trp Ile Leu Thr Met Leu Ser
  1               5                  10                  15
```

Leu Leu Gly Leu Ser Met Gly Ala Pro Ser Ala Ser Arg Cys Ser Gly
            20                  25                  30

Val Cys Ser Thr Ser Val Pro Glu Gly Phe Thr Pro Glu Gly Ser Pro
            35                  40                  45

Val Phe Gln Asp Lys Asp Ile Pro Ala Ile Asn Gln Gly Leu Ile Ser
50                  55                  60

Glu Glu Thr Pro Glu Ser Ser Phe Leu Val Glu Gly Asp Ile Ile Arg
65                  70                  75                  80

Pro Ser Pro Phe Arg Leu Leu Ser Val Thr Asn Asn Lys Trp Pro Lys
                85                  90                  95

Gly Val Gly Gly Phe Val Glu Ile Pro Phe Leu Leu Ser Arg Lys Tyr
            100                 105                 110

Asp Glu Leu Ser Arg Arg Val Ile Met Asp Ala Phe Ala Glu Phe Glu
            115                 120                 125

Arg Phe Thr Cys Ile Arg Phe Val Ala Tyr His Gly Gln Arg Asp Phe
            130                 135                 140

Val Ser Ile Leu Pro Met Ala Gly Cys Phe Ser Gly Val Gly Arg Ser
145                 150                 155                 160

Gly Gly Met Gln Val Val Ser Leu Ala Pro Thr Cys Leu Arg Lys Gly
                165                 170                 175

Arg Gly Ile Val Leu His Glu Leu Met His Val Leu Gly Phe Trp His
            180                 185                 190

Glu His Ser Arg Ala Asp Arg Asp Arg Tyr Ile Gln Val Asn Trp Asn
            195                 200                 205

Glu Ile Leu Pro Gly Phe Glu Ile Asn Phe Ile Lys Ser Arg Ser Thr
210                 215                 220

Asn Met Leu Val Pro Tyr Asp Tyr Ser Ser Val Met His Tyr Gly Arg
225                 230                 235                 240

Phe Ala Phe Ser Trp Arg Gly Gln Pro Thr Ile Ile Pro Leu Trp Thr
                245                 250                 255

Ser Ser Val His Ile Gly Gln Arg Trp Asn Leu Ser Thr Ser Asp Ile
            260                 265                 270

Thr Arg Val Cys Arg Leu Tyr Asn Cys Ser Arg Ser Val Pro Asp Ser
            275                 280                 285

His Gly Arg Gly Phe Glu Ala Gln Ser Asp Gly Ser Ser Leu Thr Pro
290                 295                 300

Ala Ser Ile Ser Arg Leu Gln Arg Leu Leu Glu Ala Leu Ser Glu Glu
305                 310                 315                 320

Ser Gly Ser Ser Ala Pro Ser Gly Ser Arg Thr Gly Gly Gln Ser Ile
                325                 330                 335

Ala Gly Leu Gly Asn Ser Gln Gln Gly Trp Glu His Pro Pro Gln Ser
            340                 345                 350

Thr Phe Ser Val Gly Ala Leu Ala Arg Pro Pro Gln Met Leu Ala Asp
            355                 360                 365

Ala Ser Lys Ser Gly Pro Gly Ala Gly Ala Asp Ser Leu Ser Leu Glu
            370                 375                 380

Gln Phe Gln Leu Ala Gln Ala Pro Thr Val Pro Leu Ala Leu Phe Pro
385                 390                 395                 400

Glu Ala Arg Asp Lys Pro Ala Pro Ile Gln Asp Ala Phe Glu Arg Leu
                405                 410                 415

Ala Pro Leu Pro Gly Gly Cys Ala Pro Gly Ser His Ile Arg Glu Val
            420                 425                 430

Pro Arg Asp
        435

<210> SEQ ID NO 20
<211> LENGTH: 401
<212> TYPE: PRT
<213> ORGANISM: Mus musculus

<400> SEQUENCE: 20

Met Gly Ile Met Gly Ser Leu Trp Pro Trp Ile Leu Thr Met Leu Ser
 1               5                   10                  15

Leu Leu Gly Leu Ser Met Gly Ala Pro Ser Ala Ser Arg Cys Ser Gly
            20                  25                  30

Val Cys Ser Thr Ser Val Pro Glu Gly Phe Thr Pro Glu Gly Ser Pro
        35                  40                  45

Val Phe Gln Asp Lys Asp Ile Pro Ala Ile Asn Gln Gly Leu Ile Ser
    50                  55                  60

Glu Glu Thr Pro Glu Ser Ser Phe Leu Leu Ser Arg Lys Tyr Asp Glu
65                  70                  75                  80

Leu Ser Arg Arg Val Ile Met Asp Ala Phe Ala Glu Phe Glu Arg Phe
                85                  90                  95

Thr Cys Ile Arg Phe Val Ala Tyr His Gly Gln Arg Asp Phe Val Ser
            100                 105                 110

Ile Leu Pro Met Ala Gly Cys Phe Ser Gly Val Gly Arg Ser Gly Gly
        115                 120                 125

Met Gln Val Val Ser Leu Ala Pro Thr Cys Leu Arg Lys Gly Arg Gly
    130                 135                 140

Ile Val Leu His Glu Leu Met His Val Leu Gly Phe Trp His Glu His
145                 150                 155                 160

Ser Arg Ala Asp Arg Asp Arg Tyr Ile Gln Val Asn Trp Asn Glu Ile
                165                 170                 175

Leu Pro Gly Phe Glu Ile Asn Phe Ile Lys Ser Arg Ser Thr Asn Met
            180                 185                 190

Leu Val Pro Tyr Asp Tyr Ser Ser Val Met His Tyr Gly Arg Phe Ala
        195                 200                 205

Phe Ser Trp Arg Gly Gln Pro Thr Ile Ile Pro Leu Trp Thr Ser Ser
    210                 215                 220

Val His Ile Gly Gln Arg Trp Asn Leu Ser Thr Ser Asp Ile Thr Arg
225                 230                 235                 240

Val Cys Arg Leu Tyr Asn Cys Ser Arg Ser Val Pro Asp Ser His Gly
                245                 250                 255

Arg Gly Phe Glu Ala Gln Ser Asp Gly Ser Ser Leu Thr Pro Ala Ser
            260                 265                 270

Ile Ser Arg Leu Gln Arg Leu Leu Glu Ala Leu Ser Glu Glu Ser Gly
        275                 280                 285

Ser Ser Ala Pro Ser Gly Ser Arg Thr Gly Gly Gln Ser Ile Ala Gly
    290                 295                 300

Leu Gly Asn Ser Gln Gln Gly Trp Glu His Pro Gln Ser Thr Phe
305                 310                 315                 320

Ser Val Gly Ala Leu Ala Arg Pro Pro Gln Met Leu Ala Asp Ala Ser
                325                 330                 335

Lys Ser Gly Pro Gly Ala Gly Ala Asp Ser Leu Ser Leu Glu Gln Phe
            340                 345                 350

Gln Leu Ala Gln Ala Pro Thr Val Pro Leu Ala Leu Phe Pro Glu Ala
        355                 360                 365

Arg Asp Lys Pro Ala Pro Ile Gln Asp Ala Phe Glu Arg Leu Ala Pro
        370                 375                 380

Leu Pro Gly Gly Cys Ala Pro Gly Ser His Ile Arg Glu Val Pro Arg
385                 390                 395                 400

Asp

<210> SEQ ID NO 21
<211> LENGTH: 413
<212> TYPE: PRT
<213> ORGANISM: Mus musculus

<400> SEQUENCE: 21

Met Gly Ile Met Gly Ser Leu Trp Pro Trp Ile Leu Thr Met Leu Ser
  1               5                  10                  15

Leu Leu Gly Leu Ser Met Gly Ala Pro Ser Ala Ser Arg Cys Ser Gly
             20                  25                  30

Val Cys Ser Thr Ser Val Pro Glu Gly Phe Thr Pro Glu Gly Ser Pro
         35                  40                  45

Val Phe Gln Asp Lys Asp Ile Pro Ala Ile Asn Gln Gly Leu Ile Ser
 50                  55                  60

Glu Glu Thr Pro Glu Ser Ser Phe Leu Val Glu Gly Asp Ile Ile Arg
65                  70                  75                  80

Pro Gly Val Ser His Gly Val Ser Phe Pro Asn Glu Leu Ser Arg Arg
                 85                  90                  95

Val Ile Met Asp Ala Phe Ala Glu Phe Glu Arg Phe Thr Cys Ile Arg
            100                 105                 110

Phe Val Ala Tyr His Gly Gln Arg Asp Phe Val Ser Ile Leu Pro Met
        115                 120                 125

Ala Gly Cys Phe Ser Gly Val Gly Arg Ser Gly Gly Met Gln Val Val
    130                 135                 140

Ser Leu Ala Pro Thr Cys Leu Arg Lys Gly Arg Gly Ile Val Leu His
145                 150                 155                 160

Glu Leu Met His Val Leu Gly Phe Trp His Glu His Ser Arg Ala Asp
                165                 170                 175

Arg Asp Arg Tyr Ile Gln Val Asn Trp Asn Glu Ile Leu Pro Gly Phe
            180                 185                 190

Glu Ile Asn Phe Ile Lys Ser Arg Ser Thr Asn Met Leu Val Pro Tyr
        195                 200                 205

Asp Tyr Ser Ser Val Met His Tyr Gly Arg Phe Ala Phe Ser Trp Arg
    210                 215                 220

Gly Gln Pro Thr Ile Ile Pro Leu Trp Thr Ser Ser Val His Ile Gly
225                 230                 235                 240

Gln Arg Trp Asn Leu Ser Thr Ser Asp Ile Thr Arg Val Cys Arg Leu
                245                 250                 255

Tyr Asn Cys Ser Arg Ser Val Pro Asp Ser His Gly Arg Gly Phe Glu
            260                 265                 270

Ala Gln Ser Asp Gly Ser Ser Leu Thr Pro Ala Ser Ile Ser Arg Leu
        275                 280                 285

Gln Arg Leu Leu Glu Ala Leu Ser Glu Glu Ser Gly Ser Ser Ala Pro
    290                 295                 300

Ser Gly Ser Arg Thr Gly Gly Gln Ser Ile Ala Gly Leu Gly Asn Ser
305                 310                 315                 320

Gln Gln Gly Trp Glu His Pro Pro Gln Ser Thr Phe Ser Val Gly Ala
                325                 330                 335

Leu Ala Arg Pro Pro Gln Met Leu Ala Asp Ala Ser Lys Ser Gly Pro
            340                 345                 350

Gly Ala Gly Ala Asp Ser Leu Ser Leu Glu Gln Phe Gln Leu Ala Gln
        355                 360                 365

Ala Pro Thr Val Pro Leu Ala Leu Phe Pro Glu Ala Arg Asp Lys Pro
370                 375                 380

Ala Pro Ile Gln Asp Ala Phe Glu Arg Leu Ala Pro Leu Pro Gly Gly
385                 390                 395                 400

Cys Ala Pro Gly Ser His Ile Arg Glu Val Pro Arg Asp
                405                 410

<210> SEQ ID NO 22
<211> LENGTH: 1296
<212> TYPE: DNA
<213> ORGANISM: Homo sapiens

<400> SEQUENCE: 22

```
atggagggtg taggggtct  ctggccttgg gtgctgggtc tgctctcctt gccaggtgtg      60
atcctaggag cgccctggc  ctccagctgc gcaggagcct gtggtaccag cttcccagat     120
ggcctcaccc ctgagggaac ccaggcctcc ggggacaagg acattcctgc aattaaccaa     180
gggctcatcc tggaagaaac cccagagagc agcttcctca tcgagggga  catcatccgg     240
ccgagtccct tccgactgct gtcagcaacc agcaacaaat ggcccatggg tggtagtggt     300
gtcgtggagg tccccttcct gctctccagc aagtacgatg agcccagccg ccaggtcatc     360
ctggaggctc ttgcggagtt tgaacgttcc acgtgcatca ggtttgtcac ctatcaggac     420
cagagagact tcatttccat catccccatg tatgggtgct ctcgagtgt  ggggcgcagt     480
ggagggatgc aggtggtctc cctggcgccc acgtgtctcc agaagggccg ggcattgtc     540
cttcatgagc tcatgcatgt gctgggcttc tggcacgagc acacgcgggc cgaccgggac     600
cgctatatcc gtgtcaactg gaacgagatc ctgccaggct tgaaatcaa  cttcatcaag     660
tctcagagca gcaacatgct gacgccctat gactactcct ctgtgatgca ctatgggagg     720
ctcgccttca gccggcgtgg gctgccacc  atcacaccac tttgggcccc cagtgtccac     780
atcggccagc gatggaacct gagtgcctcg gacatcaccc gggtcctcaa actctacggc     840
tgcagcccaa gtggcccag  gccccgtggg agagggtccc atgccacag  cactggtagg     900
agccccgctc cggcctccct atctctgcag cggcttttgg aggcactgtc ggcggaatcc     960
aggagccccg accccagtgg ttccagtgcg ggaggccagc ccgttcctgc agggcctggg    1020
gagagcccac atgggtggga gtcccctgcc ctgaaaaagc tcagtgcaga ggcctcggca    1080
aggcagcctc agaccctagc ttcctcccca agatcaaggc ctggagcagg tgccccggt    1140
gttgctcagg agcagtcctg gctggccgga gtgtccacca gcccacagt  cccatcttca    1200
gaagcaggaa tccagccagt ccctgtccag ggaagcccag ctctgccagg gggctgtgta    1260
cctagaaatc atttcaaggg gatgtccgaa gattaa                              1296
```

<210> SEQ ID NO 23
<211> LENGTH: 431
<212> TYPE: PRT
<213> ORGANISM: Homo sapiens

<400> SEQUENCE: 23

Met Glu Gly Val Gly Gly Leu Trp Pro Trp Val Leu Gly Leu Leu Ser
1               5                   10                  15

```
Leu Pro Gly Val Ile Leu Gly Ala Pro Leu Ala Ser Ser Cys Ala Gly
            20                  25                  30

Ala Cys Gly Thr Ser Phe Pro Asp Gly Leu Thr Pro Glu Gly Thr Gln
            35                  40                  45

Ala Ser Gly Asp Lys Asp Ile Pro Ala Ile Asn Gln Gly Leu Ile Leu
    50                  55                  60

Glu Glu Thr Pro Glu Ser Ser Phe Leu Ile Glu Gly Asp Ile Ile Arg
65                  70                  75                  80

Pro Ser Pro Phe Arg Leu Leu Ser Ala Thr Ser Asn Lys Trp Pro Met
                85                  90                  95

Gly Gly Ser Gly Val Val Glu Val Pro Phe Leu Leu Ser Ser Lys Tyr
            100                 105                 110

Asp Glu Pro Ser Arg Gln Val Ile Leu Glu Ala Leu Ala Glu Phe Glu
            115                 120                 125

Arg Ser Thr Cys Ile Arg Phe Val Thr Tyr Gln Asp Gln Arg Asp Phe
            130                 135                 140

Ile Ser Ile Ile Pro Met Tyr Gly Cys Phe Ser Ser Val Gly Arg Ser
145                 150                 155                 160

Gly Gly Met Gln Val Val Ser Leu Ala Pro Thr Cys Leu Gln Lys Gly
            165                 170                 175

Arg Gly Ile Val Leu His Glu Leu Met His Val Leu Gly Phe Trp His
            180                 185                 190

Glu His Thr Arg Ala Asp Arg Asp Arg Tyr Ile Arg Val Asn Trp Asn
            195                 200                 205

Glu Ile Leu Pro Gly Phe Glu Ile Asn Phe Ile Lys Ser Gln Ser Ser
            210                 215                 220

Asn Met Leu Thr Pro Tyr Asp Tyr Ser Ser Val Met His Tyr Gly Arg
225                 230                 235                 240

Leu Ala Phe Ser Arg Arg Gly Leu Pro Thr Ile Thr Pro Leu Trp Ala
                245                 250                 255

Pro Ser Val His Ile Gly Gln Arg Trp Asn Leu Ser Ala Ser Asp Ile
            260                 265                 270

Thr Arg Val Leu Lys Leu Tyr Gly Cys Ser Pro Ser Gly Pro Arg Pro
            275                 280                 285

Arg Gly Arg Gly Ser His Ala His Ser Thr Gly Arg Ser Pro Ala Pro
            290                 295                 300

Ala Ser Leu Ser Leu Gln Arg Leu Leu Glu Ala Leu Ser Ala Glu Ser
305                 310                 315                 320

Arg Ser Pro Asp Pro Ser Gly Ser Ala Gly Gly Gln Pro Val Pro
                325                 330                 335

Ala Gly Pro Gly Glu Ser Pro His Gly Trp Glu Ser Pro Ala Leu Lys
            340                 345                 350

Lys Leu Ser Ala Glu Ala Ser Ala Arg Gln Pro Gln Thr Leu Ala Ser
            355                 360                 365

Ser Pro Arg Ser Arg Pro Gly Ala Gly Ala Pro Gly Val Ala Gln Glu
            370                 375                 380

Gln Ser Trp Leu Ala Gly Val Ser Thr Lys Pro Thr Val Pro Ser Ser
385                 390                 395                 400

Glu Ala Gly Ile Gln Pro Val Pro Val Gln Gly Ser Pro Ala Leu Pro
                405                 410                 415

Gly Gly Cys Val Pro Arg Asn His Phe Lys Gly Met Ser Glu Asp
            420                 425                 430
```

<210> SEQ ID NO 24
<211> LENGTH: 11
<212> TYPE: PRT
<213> ORGANISM: Mus musculus

<400> SEQUENCE: 24

His Glu Leu Met His Val Leu Gly Phe Trp His
1               5                   10

<210> SEQ ID NO 25
<211> LENGTH: 5
<212> TYPE: PRT
<213> ORGANISM: Mus musculus

<400> SEQUENCE: 25

Ser Val Met His Tyr
1               5

<210> SEQ ID NO 26
<211> LENGTH: 11
<212> TYPE: PRT
<213> ORGANISM: Mus musculus
<220> FEATURE:
<221> NAME/KEY: SITE
<222> LOCATION: 3, 4, 6, 7, 9, 10
<223> OTHER INFORMATION: Xaa = any naturally occurring amino acid
<221> NAME/KEY: VARIANT
<222> LOCATION: (1)...(11)
<223> OTHER INFORMATION: Xaa = Any Amino Acid
<221> NAME/KEY: VARIANT
<222> LOCATION: (1)...(11)
<223> OTHER INFORMATION: Xaa = Any Amino Acid

<400> SEQUENCE: 26

His Glu Xaa Xaa His Xaa Xaa Gly Xaa Xaa His
1               5                   10

<210> SEQ ID NO 27
<211> LENGTH: 5
<212> TYPE: PRT
<213> ORGANISM: Mus musculus
<220> FEATURE:
<221> NAME/KEY: SITE
<222> LOCATION: 2
<223> OTHER INFORMATION: Xaa = any naturally occurring amino acid
<221> NAME/KEY: VARIANT
<222> LOCATION: (1)...(5)
<223> OTHER INFORMATION: Xaa = Any Amino Acid
<221> NAME/KEY: VARIANT
<222> LOCATION: (1)...(5)
<223> OTHER INFORMATION: Xaa = Any Amino Acid

<400> SEQUENCE: 27

Ser Xaa Met His Tyr
1               5

<210> SEQ ID NO 28
<211> LENGTH: 262
<212> TYPE: PRT
<213> ORGANISM: Zebrafish

<400> SEQUENCE: 28

Met Asp Ile Arg Ala Ser Leu Ser Ile Leu Leu Leu Phe Gly Leu Ser
1               5                   10                  15

Gln Ala Ser Pro Leu Arg Glu Phe Glu Ala Val Phe Val Ser Glu Pro
            20                  25                  30

Glu Thr Val Asp Ile Thr Thr Gln Ile Leu Glu Thr Asn Lys Gly Ser
        35                  40                  45

```
Ser Glu Val Leu Phe Glu Gly Asp Val Val Leu Pro Lys Asn Arg Asn
    50                  55                  60

Ala Leu Ile Cys Glu Asp Lys Ser Cys Phe Trp Lys Lys Asn Ala Asn
65                  70                  75                  80

Asn Ile Val Glu Val Pro Tyr Val Val Ser Gly Glu Phe Ser Ile Asn
                    85                  90                  95

Asp Lys Ser Val Ile Ala Asn Ala Ile Ser Ile Phe His Ala Gln Thr
                100                 105                 110

Cys Ile Arg Phe Val Pro Arg Ser Ile Gln Ala Asp Tyr Leu Ser Ile
            115                 120                 125

Glu Asn Lys Asp Gly Cys Tyr Ser Ala Ile Gly Arg Thr Gly Gly Lys
            130                 135                 140

Gln Val Val Ser Leu Asn Arg Lys Gly Cys Val Tyr Ser Gly Ile Ala
145                 150                 155                 160

Gln His Glu Leu Asn His Ala Leu Gly Phe Tyr Asn Glu Gln Ser Arg
                165                 170                 175

Ser Asp Arg Asp Gln Tyr Val Arg Ile Asn Trp Asn Asn Ile Ser Pro
                180                 185                 190

Gly Met Ala Tyr Asn Phe Leu Lys Gln Lys Thr Asn Asn Gln Asn Thr
            195                 200                 205

Pro Tyr Asp Tyr Gly Ser Leu Met His Tyr Gly Lys Thr Ala Phe Ala
            210                 215                 220

Ile Gln Pro Gly Leu Glu Thr Ile Thr Pro Ile Pro Asp Glu Asn Val
225                 230                 235                 240

Gln Ile Gly Gln Arg Gln Gly Leu Ser Lys Ile Asp Ile Leu Gly Ile
                245                 250                 255

Asn Lys Leu Tyr Gly Cys
                260

<210> SEQ ID NO 29
<211> LENGTH: 315
<212> TYPE: PRT
<213> ORGANISM: Nematode

<400> SEQUENCE: 29

Met Met Thr Ile Gln Arg Tyr Ser Leu Val Phe Cys Ala Ile Phe Ala
1               5                   10                  15

Thr Cys Trp Thr Ala Ser Val Val Asn Asn Lys Gln Val Ile Asp Thr
                20                  25                  30

Ser Val Pro Gln Thr Glu Thr Thr Leu Asn Asp Ala Asp Phe His Ser
            35                  40                  45

Asp Leu His Gln Arg Tyr Asp Leu Gln Thr Leu Gly Ile Lys Val Lys
        50                  55                  60

Asp Asp Pro Thr Ile Gly Asn Tyr Ser Glu Gly Asp Ile Leu Leu Glu
65                  70                  75                  80

Ser Pro Lys Lys Phe Val Glu Glu Asn Lys Leu Gly Arg Asn Ala
                85                  90                  95

Ile Lys Gln Ile Tyr Arg Arg Trp Pro Asn Asn Glu Ile Pro Tyr Thr
            100                 105                 110

Leu Ser Ser Gln Tyr Gly Ser Tyr Ala Arg Ser Val Ile Ala Asn Ala
            115                 120                 125

Met Asn Glu Tyr His Thr Lys Thr Cys Val Lys Phe Val Ala Arg Asp
            130                 135                 140

Pro Ser Lys His His Asp Tyr Leu Trp Ile His Pro Asp Glu Gly Cys
```

```
                  145                 150                 155                 160
          Tyr Ser Leu Val Gly Lys Thr Gly Gly Lys Gln Pro Val Ser Leu Asp
                          165                 170                 175

Ser Gly Cys Ile Gln Val Gly Thr Ile Val His Glu Leu Met His Ala
                          180                 185                 190

Val Gly Phe Phe His Glu Gln Ser Arg Gln Asp Arg Asp Ser Tyr Ile
                          195                 200                 205

Asp Val Val Trp Gln Asn Val Met Asn Gly Ala Asp Asp Gln Phe Glu
                      210                 215                 220

Lys Tyr Asn Leu Asn Val Ile Ser His Leu Asp Glu Pro Tyr Asp Tyr
          225                 230                 235                 240

Ala Ser Ile Met His Tyr Gly Pro Tyr Ala Phe Ser Gly Ser Gly Lys
                          245                 250                 255

Lys Thr Leu Val Pro Lys Lys Ser Gly Ser Glu Arg Met Gly Gln Arg
                          260                 265                 270

Val Lys Phe Ser Asp Ile Asp Val Arg Lys Ile Asn Lys Leu Tyr Asn
                          275                 280                 285

Cys Pro Gly Val Ser Gly Asn Asn Asn Asn Asn Asn Asn Asn Gln Ile
                      290                 295                 300

Asn Ser Asn Ser Ile Val Asn His Pro Gln Val
          305                 310                 315
```